US012723079B2

(12) United States Patent
Amirina et al.

(10) Patent No.: US 12,723,079 B2
(45) Date of Patent: Sep. 1, 2026

(54) ANTI-PD-1 ANTIBODIES

(71) Applicant: PD-1 Acquisition Group, LLC, Gulf Breeze, FL (US)

(72) Inventors: Najmia Amirina, Cambridge, MA (US); Hareesh Chamarthi, Allston, MA (US); Maria Isabel Chiu, Newton Centre, MA (US); Daniel Doty, Arlington, MA (US); Bin Feng, Newton, MA (US); Aleksander Jonca, Boston, MA (US); Thomas McQuade, Cambridge, MA (US); Anhco Nguyen, Needham, MA (US); Sheila Ranganath, Arlington, MA (US); Hans Albert Felix Scheuplein, Arlington, MA (US); Vikki A. Spaulding, Acton, MA (US); Lei Wang, Braintree, MA (US); Jennifer Watkins-Yoon, Brighton, MA (US); Sri Sahitya Vadde, Ashland, MA (US)

(73) Assignee: PD-I Acquisition Group, LLC, New York, NY (US)

( * ) Notice: Subject to any disclaimer, the term of this patent is extended or adjusted under 35 U.S.C. 154(b) by 675 days.

(21) Appl. No.: 18/193,189

(22) Filed: Mar. 30, 2023

(65) Prior Publication Data

US 2023/0265189 A1 Aug. 24, 2023

Related U.S. Application Data

(60) Division of application No. 16/728,653, filed on Dec. 27, 2019, now Pat. No. 11,639,385, which is a continuation of application No. 15/152,192, filed on May 11, 2016, now Pat. No. 10,544,217, which is a division of application No. 14/975,769, filed on Dec. 19, 2015, now Pat. No. 10,239,942.

(60) Provisional application No. 62/261,118, filed on Nov. 30, 2015, provisional application No. 62/251,082, filed on Nov. 4, 2015, provisional application No. 62/220,199, filed on Sep. 17, 2015, provisional application No. 62/095,675, filed on Dec. 22, 2014.

(51) Int. Cl.

| | |
|---|---|
| ***C07K 16/28*** | (2006.01) |
| ***A61K 39/395*** | (2006.01) |
| ***A61K 49/00*** | (2006.01) |
| ***A61P 35/00*** | (2006.01) |
| *A61K 39/00* | (2006.01) |

(52) U.S. Cl.

CPC ...... *C07K 16/2803* (2013.01); *A61K 49/0058* (2013.01); *C07K 16/2818* (2013.01); *A61K 2039/505* (2013.01); *A61K 2039/507* (2013.01); *A61K 2039/54* (2013.01); *A61K 2039/545* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/567* (2013.01); *C07K 2317/73* (2013.01); *C07K 2317/75* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 8,735,553 | B1 | 5/2014 | Li et al. | |
| 10,239,942 | B2 | 3/2019 | Amirina et al. | |
| 10,544,217 | B2 | 1/2020 | Amirina et al. | |
| 11,639,385 | B2 * | 5/2023 | Amirina ............. | A61K 49/0058 424/9.1 |
| 2016/0251436 | A1 | 9/2016 | Amirina et al. | |
| 2016/0319019 | A1 | 11/2016 | Amirina et al. | |
| 2020/0190187 | A1 | 6/2020 | Amirina et al. | |

FOREIGN PATENT DOCUMENTS

| | | | |
|---|---|---|---|
| AU | 2014201367 | A1 | 4/2014 |
| EP | 3026062 | A1 | 6/2016 |
| WO | WO 2006/121168 | A1 | 11/2006 |
| WO | WO 2008/156712 | A1 | 12/2008 |
| WO | 2010/036959 | A2 | 4/2010 |
| WO | WO 2014/206107 | A1 | 12/2014 |
| WO | WO 2015/127407 | A1 | 8/2015 |
| WO | WO 2016/106159 | | 6/2016 |

OTHER PUBLICATIONS

Abdiche, Y.N. et al., "Assessing kinetic and epitopic diversity across orthogonal monoclonal antibody generation platforms," mAbs, vol. 8; No. 2; 264-277 (2016).

Agata, Y. et al., "Expression of the PD-1 Antigen on the Surface of Simulated Mouse T and B Lymphocytes," International Immunology, vol. 8; No. 5; 765-772 (1996).

Boyd, S. D. et al., "Deep sequencing and human antibody repertoire analysis," Current Opinion in Immunology, vol. 40; 103-109 (2016).

Conroy, P.J. et al., "Antibodies: From novel repertoires to defining and refining the structure of biologically important targets," Methods; vol. 116; 12-22 (2017).

Damschroder, M.M. et al., "Analysis of human and primate CD2 molecules by protein sequence and epitope mapping with anti-human CD2 antibodies," Molecular Immunology, vol. 41; 985-1000 (2004).

Ferrara, F. et al., "Recombinant renewable polyclonal antibodies," mAbs, vol. 7; 32-41 (2015).

(Continued)

*Primary Examiner* — Ilia I Ouspenski

(74) *Attorney, Agent, or Firm* — Hamilton, Brook, Smith & Reynold, P.C.

(57) ABSTRACT

Antibodies that bind to programmed cell death protein 1 (PD-1), compositions comprising such antibodies, and methods of making and using such antibodies are disclosed.

14 Claims, 27 Drawing Sheets

Specification includes a Sequence Listing.

(56) References Cited

OTHER PUBLICATIONS

Khan, L. et al., "Cross-neutralizing anti-HIV-1 human single chain variable fragments(scFvs) against CD4 binding site and N332 glycan identified from a recombinant phage library," Scientific Reports, vol. 7; 45163; 12 pages (2017).

Konitzer, J.D. et al., "Generation of a highly diverse panel of antagonistic chicken monoclonal antibodies against the GIP receptor," mAbs; vol. 9; No. 3; 536-549 (2017).

Lee, J.L. et al., "Molecular-level analysis of the serum antibody repertoire in young adults before and after seasonal influenze vaccination," Nature Medicine; vol. 22; 1456-1464 (2016).

Parola, C. et al., "Integrating high-throughout screening and sequencing for monoclonal antibody discovery and engineering," Immunology, vol. 153; 31-41 (2018).

Sheehan, J. and Marasco, W.A., "Phage and Yeast Display," Microbiology Spectrum, vol. 3; No. 1; 17 pages (2015).

Van Regenmortel, M.H.V., "Development of a Preventive HIV Vaccine Requires Solving Inverse Problems Which is Unattainable by Rational Vaccine Design," Frontiers in Immunology, vol. 8; 11 pages, (2018).

Zhou, T. et al., "Structural Repertoire of HIV-1-Neutralizing Antibodies Targeting the CD4 Supersite in 14 Donors," Cell; 161; 1280-1292 (2015).

Final Office Action for U.S. Appl. No. 15/152,192, mailed Jul. 9, 2019.

Final Office Action for U.S. Appl. No. 16/728,653, mailed Nov. 3, 2022.

International Preliminary Report on Patentability for International Application No. PCT/US2015/066954, entitled: Anti-PD-1 Antibodies, mailed Jul. 6, 2017.

Invitation to Pay Additional Fees with Partial Search Report for PCT/US2015/066954, entitled: "Anti-PD-1 Antibodies," mailed Apr. 4, 2016.

Non-Final Office Action for U.S. Appl. No. 14/975,769, mailed Jul. 18, 2018.

Non-Final Office Action for U.S. Appl. No. 15/152,192, mailed Oct. 17, 2018.

Non-Final Office Action for U.S. Appl. No. 15/152,192, mailed Feb. 14, 2019.

Non-Final Office Action for U.S. Appl. No. 16/728,653, mailed Jul. 26, 2022.

Notice of Allowance for U.S. Appl. No. 14/975,769, mailed Nov. 15, 2018.

Notice of Allowance for U.S. Appl. No. 15/152,192, mailed Sep. 9, 2019.

Notice of Allowance for U.S. Appl. No. 16/728,653, mailed Dec. 19, 2022.

Transmittal of the International Search Report and the Written Opinion for International Application No. PCT/US2015/066954, entitled: "Anti-PD-1 Antibodies," mailed May 30, 2016.

Boyd, S.D. and Crowe, Jr., J.E., "Deep sequencing and human antibody repertoire analysis," Current Opinion in Immunology, vol. 40; 103-109 (2016).

Davies, J. and Riechmann, L., "Affinity improvement of single antibody VH domains: residues in all three hypervariable regions affect antigen binding," Immunotechnology, vol. 2; 169-179 (1996).

Khan, L. et al., "Cross-neutralizing anti-HIV-1 human single chain variable fragments(scFvs) against CD4 binding site and N332 glycan identified from a recombinant phage library," Sci. Rep.; vol. 7; 45163; 12 pages (2017).

Parola, C. et al., "Integrating high-throughput screening and sequencing for monoclonal antibody discovery and engineering," Immunology, vol. 153; 31-41 (2018).

Sheehan, J. and Marasco, W.A., "Phage and Yeast Display," Microbiol. Spectr., vol. 3; No. 1; 17 pages (2015).

Vaughan, T.J. et al., "Human antibodies with sub-nanomolar affinities isolated from a large non-immunized phage display library," Nature Biotechnology, vol. 14; 309-314 (1996).

* cited by examiner

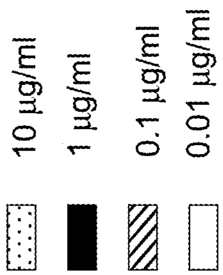
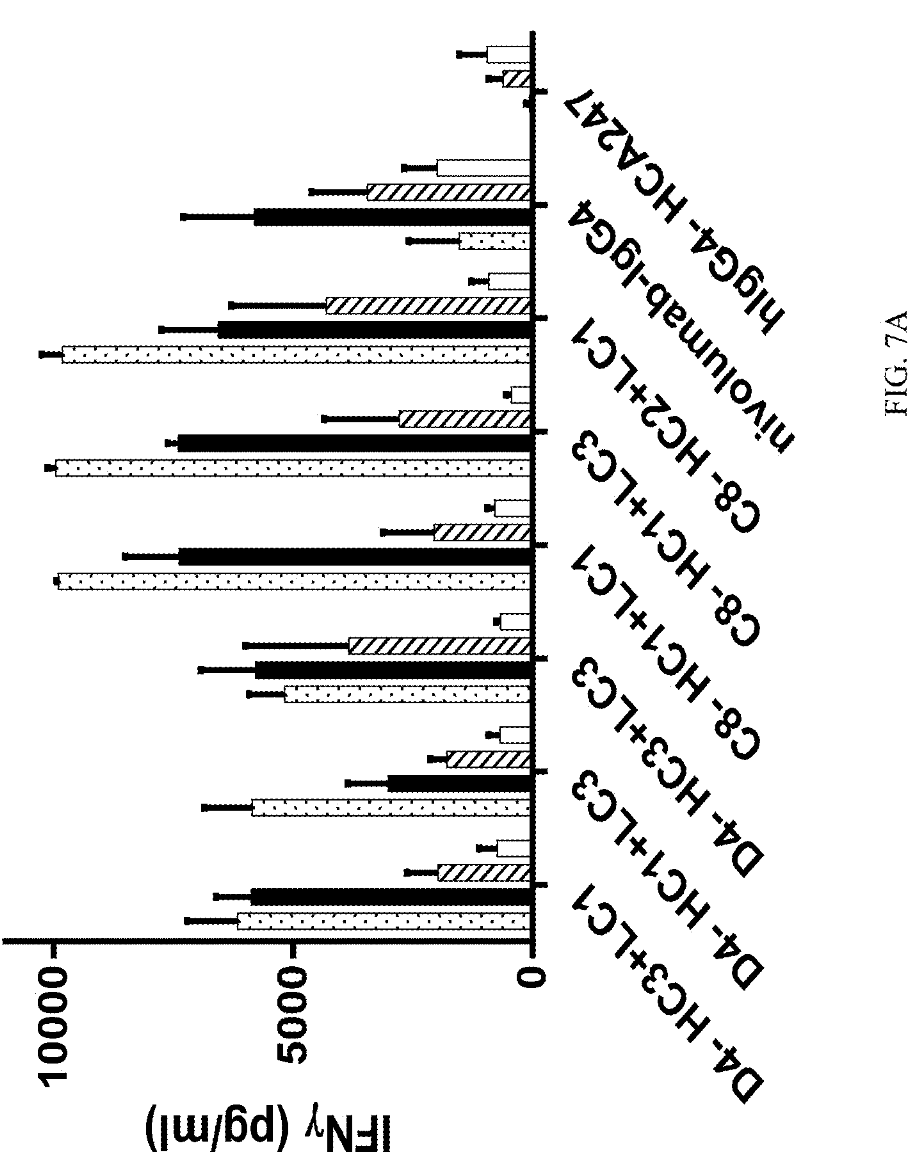
FIG. 7A

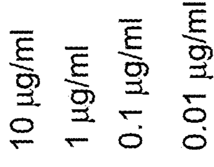
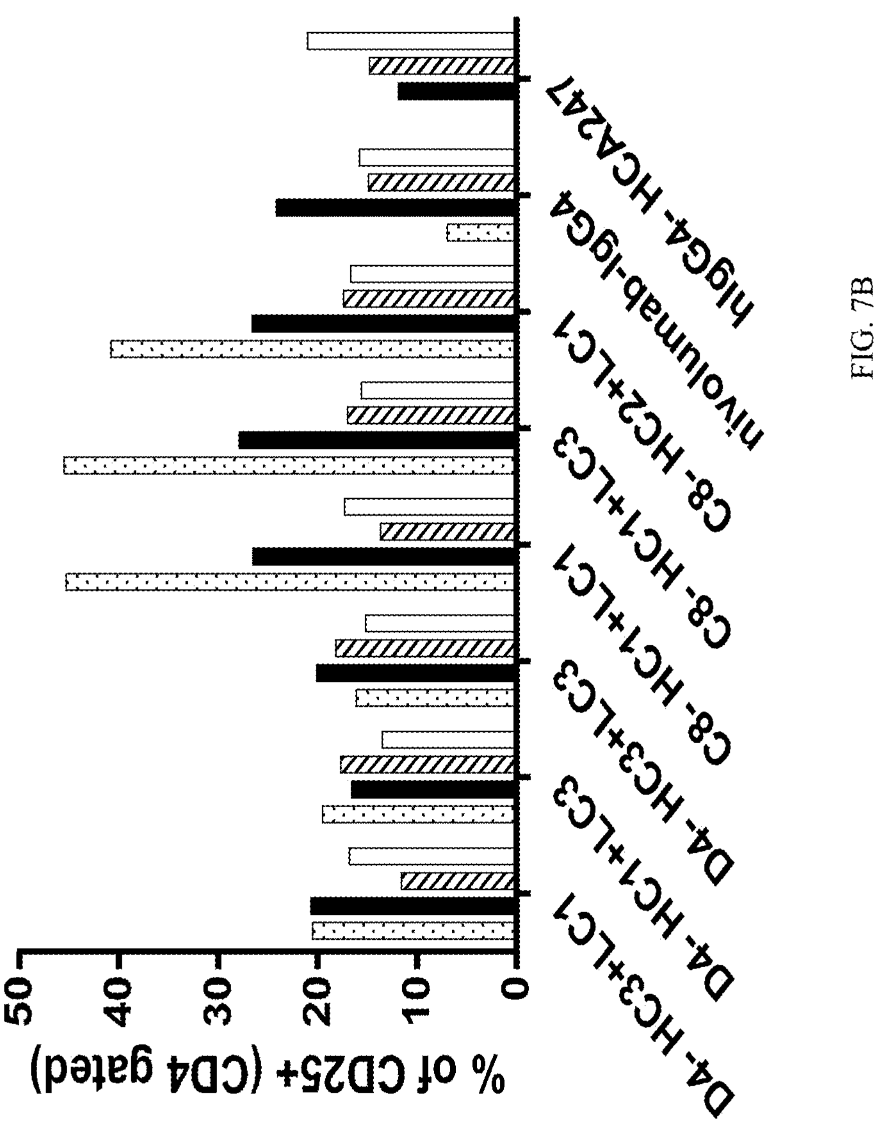
FIG. 7B

246A10

PDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQT (SEQ ID NO: 97)

244C8

PDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQT (SEQ ID NO: 97)

388D4

PDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQT (SEQ ID NO: 97)

413D2

PDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQT (SEQ ID NO: 97)

413E1

PDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQT (SEQ ID NO: 97)

FIG. 8

Heavy Chain

```
                        10        20        30        40        50        60
                ....|....|....|....|....|....|....|....|....|....|....|....|
100388_D4_VH3   EVQLQESGAELVRPGASVTLSCKASGYTFTDYEMHWVKQTPVHGLEWIGVIDPGTGGTAY
100388_D4_HC1   ....VQ....VKK.....KV.................R.A.GQ....M.I..........
100388_D4_HC2   ....VQ....VKK.....KV.................R.A.GQ....M.I..........
100388_D4_HC3   ....VQ....VKK.....KV.................R.A.GQR...M............

                        70        80        90       100       110       120
                ....|....|....|....|....|....|....|....|....|....|....|....|
100388_D4_VH3   NQKFKVKALLTADKSSNTAYMELRSLTSEDSAVYYCTSEKFGSNYYFDYWGQGTTLTVSS
100388_D4_HC1   ....QGRVTM.....TS.V....S..R...T.......................LV....
100388_D4_HC2   ....QGRVTM.....T..V....S..R...T.......................LV....
100388_D4_HC3   ....QGRVTI.....AS......S..R...T.......................LV....
```

Light chain

```
                        10        20        30        40        50        60
                ....|....|....|....|....|....|....|....|....|....|....|....|
100389_D4_VK5   DIVITQTPLSLPVSLGDQASISCRSSQTIVHSDGNTYLEWYLQKPGQSPKLLIYKVSNRF
100389_D4_LC1   .V.M..S......T..QP.......................Q.R.....R..........
100389_D4_LC2   ...M..S......T..QP.......................Q.R................
100389_D4_LC3   ...M......S..T..QP.......................Q.R...P.R..........

                        70        80        90       100       110
                ....|....|....|....|....|....|....|....|....|....|..
100389_D4_VK5   SGVPDRFSGSGSGTDFTLKISRVEAEDLGVYYCFQGSHVPLTFGAGTKLEIK
100389_D4_LC1   ...........................V................Q.......
100389_D4_LC2   ...........................V................Q.......
100389_D4_LC3   ...........A...............V................Q.......
```

FIG. 10A

Heavy chain

```
                         10        20        30        40        50        60
                 ....|....|....|....|....|....|....|....|....|....|....|....|
100244_C8_VH3    EVQLQESGPELVRPGASVKMSCKASGYTFTSYWMHWVKQRPGQGLEWIGMIDPSNSETSL
100244_C8_HC1    Q...VQ..A.VKK......V.................R.A.......M............
100244_C8_HC2    ....VQ..A.VKK......V.................R.A.......M............
100244_C8_HC3    ....VQ..T.VTK......V.................R.A.......L..........T.

                         70        80        90       100       110       120
                 ....|....|....|....|....|....|....|....|....|....|....|....|
100244_C8_VH3    NQKFKDKATLNVDKSTNTAYMQLSSLTSEDSAVYYCARSRGNYAYEMDYWGQGTSVTVSS
100244_C8_HC1    ....QGRV.MT.......V..E....R...T.......................L.....
100244_C8_HC2    ....QGRV.............E....R...T.......................L.....
100244_C8_HC3    ....QGRV.MT.......V..E.T..R...T.......................L.....
```

Light chain

```
                         10        20        30        40        50        60
                 ....|....|....|....|....|....|....|....|....|....|....|....|
100245_C8_Vk5m1  DIVLTQTPAIMSASPGEKVTLTCSASSSVSSNYLYWYQQRPGSSPKLWIYSTSNLASGVP
100245_C8_LC1    E.....S..TL.L....RA..S.R...............K..QA.R.L......R.T.I.
100245_C8_LC2    ......S..TL.L....RA..S.R...............K..QA.R.L........T.I.
100245_C8_LC3    ......S.GTL.L........S.R...............K..QA.R.V........T.I.

                         70        80        90       100
                 ....|....|....|....|....|....|....|....|....|...
100245_C8_Vk5m1  ARFSGSGSGTSYSLTISSMEAEDAASYFCHQWSSYPPTFGSGTKLEIK
100245_C8_LC1    ..........D.T.....L.P..F.V.Y...........Q........
100245_C8_LC2    ..........D.T.....L.P..F.V.............Q........
100245_C8_LC3    D.........D.T....RL.P..F.V.............Q...V....
```

FIG. 10B 800
600
400
200
0
TNF-α (pg/ml)
388D4-2 (10 ug/mL)
244C8-1 (10 ug/mL)
IgG4 Isotype Control(10 ug/mL)

SEQUENCE LISTING

```
Sequence total quantity: 97
SEQ ID NO: 1            moltype = AA  length = 120
FEATURE                 Location/Qualifiers
source                  1..120
                        mol_type = protein
                        organism = Mus musculus
SEQUENCE: 1
EVQLQESGPE LVRPGASVKM SCKASGYTFT SYWMHWVKQR PGQGLEWIGM IDPSNSETSL  60
NQKFKDKATL NVDKSTNTAY MQLSSLTSED SAVYYCARSR GNYAYEMDYW GQGTSVTVSS  120

SEQ ID NO: 2            moltype = AA  length = 120
FEATURE                 Location/Qualifiers
source                  1..120
                        mol_type = protein
                        organism = Mus musculus
SEQUENCE: 2
EVQLQESGPE LVRPGASVKM SCKASGYTFT SYWMHWVKQR PGQGLEWIGM IDPSNSETSL  60
NQKFKDKATL NVDKSTNTAY MQLSSLTSED SAVYYCARSR GNYAYEMDYW GQGTSVTVSS  120

SEQ ID NO: 3            moltype = AA  length = 120
FEATURE                 Location/Qualifiers
source                  1..120
                        mol_type = protein
                        organism = Mus musculus
SEQUENCE: 3
EVQLQESGPE LVRPGASVKM SCKASGYTFT SYWMHWVKQR PGQGLEWIGM IEPSSSETSL  60
NQKFKDKATL NVDKSSNTAY MQLSSLTSED SAVYYCARSR GNYAYEMDYW GQGTSVTVSS  120

SEQ ID NO: 4            moltype = AA  length = 120
FEATURE                 Location/Qualifiers
source                  1..120
                        mol_type = protein
                        organism = Mus musculus
SEQUENCE: 4
EVQLQESGPE LVRPGASVKM SCKASGYTFT SYWMHWVKQR PGQGLEWIGM IDPYSSETSL  60
NQKFKDKATL NVDKISNTAY MQLSSLTSED SAVYFCARSR GNYAYDMDYW GQGTSVTVSS  120

SEQ ID NO: 5            moltype = AA  length = 120
FEATURE                 Location/Qualifiers
source                  1..120
                        mol_type = protein
                        organism = Mus musculus
SEQUENCE: 5
EVQLQESGPE LVRPGASVKM SCKASGYTFT SYWMHWVKQR PGQGLEWIGM IDPSNSETSL  60
NQKFKDKATL NVDKSSKTAY MQLSSLTSED SAVYYCARSR GNYAYDMDYW GQGTSVTVSS  120

SEQ ID NO: 6            moltype = AA  length = 117
FEATURE                 Location/Qualifiers
source                  1..117
                        mol_type = protein
                        organism = Mus musculus
SEQUENCE: 6
EVQLQESGAE LVMPGASVKM SCKASGYTFT DYWMHWVKQR PGQGLEWIGA IDTSDSYTSY  60
```

```
HQNFKGKATL TEDESSSTAY MQLSSLTSED SAIYYCARRD YGGFGYWGQG TTLTVSS     117

SEQ ID NO: 7            moltype = AA  length = 116
FEATURE                 Location/Qualifiers
source                  1..116
                        mol_type = protein
                        organism = Mus musculus
SEQUENCE: 7
EVQLQESGPE LVKPGASVKI PCKASGYTFT DYNMDWVKKS HGKSLEWIGD IDPNNGGTIY  60
NQKFKGKATL TVDKSSRTAY MELRSLTSED TAVYYCARWR SSMDYWGQGT SVTVSS      116

SEQ ID NO: 8            moltype = AA  length = 116
FEATURE                 Location/Qualifiers
source                  1..116
                        mol_type = protein
                        organism = Mus musculus
SEQUENCE: 8
EVQLQESGPE LVKPGASVKI PCRASGYIFT DYNMDWVKQS HGKSLEWIGD IDPNNGGTIY  60
NQKFKDKTTL TVDKSSRTAY MELRSLTSED TAVYYCARWR SSMDYWGQGT SVTVSS      116

SEQ ID NO: 9            moltype = AA  length = 116
FEATURE                 Location/Qualifiers
source                  1..116
                        mol_type = protein
                        organism = Mus musculus
SEQUENCE: 9
EVQLQESGPE LVKPGASVKI PCKASGYTFT DYNMDWVKQN HGKSLEWIGD IDPNNGDTIY  60
NQKFKGKATL TVDKSSRTAY MELRSLTSED TAVYYCARWR SSMDYWGQGT SVTVSS      116

SEQ ID NO: 10           moltype = AA  length = 116
FEATURE                 Location/Qualifiers
source                  1..116
                        mol_type = protein
                        organism = Mus musculus
SEQUENCE: 10
EVQLQESGPE LVKPGASVKI PCKASGYTFT DYNMDWVKQS HGKSLEWIGD IDPNSGGSIY  60
NQKFKGKATL TVDKSSRTVY MELRSLTSED TAVYYCARWR SSMDYWGQGT SVTVSS      116

SEQ ID NO: 11           moltype = AA  length = 116
FEATURE                 Location/Qualifiers
source                  1..116
                        mol_type = protein
                        organism = Mus musculus
SEQUENCE: 11
EVQLQESGPE LVKPGASVKI TCKASGYTFT DYNMDWVKQS HGKSLEWIGD IDPNNGGTIY  60
NQKFKGKATL TVDKSSNTAY MELRSLASED TAVYYCARWR SSMDYWGQGT SVSVSS      116

SEQ ID NO: 12           moltype = AA  length = 116
FEATURE                 Location/Qualifiers
source                  1..116
                        mol_type = protein
                        organism = Mus musculus
SEQUENCE: 12
EVQLQESGPE LVKPGASVKI PCKASGYTFT DYNMDWVKQS HGKSLEWIGD IDPNNGGTIY  60
NQNFKGKATL TVDKSSSTAY MELRSLTSED TAVYYCARWR SSMDYWGQGT SVTVSS      116

SEQ ID NO: 13           moltype = AA  length = 116
FEATURE                 Location/Qualifiers
source                  1..116
                        mol_type = protein
                        organism = Mus musculus
SEQUENCE: 13
EVQLQESGPE LVKPGASVKI PCKASGYTFT DYNMDWVKQS HGKSLEWIGD IDPNNGGIIY  60
NQKFKGKAAL TVDKSSSTAY MELRSLTSED TAVYYCARWR SSMDYWGQGT SVTVSS      116

SEQ ID NO: 14           moltype = AA  length = 116
FEATURE                 Location/Qualifiers
source                  1..116
                        mol_type = protein
                        organism = Mus musculus
SEQUENCE: 14
EVQLQESGPE LVKPGASVKI PCKASGYTFT DYNMDWVKQS HGKSLEWIGD IDPNNGGIIY  60
NQKFKGKAAL TVDKSSSTAY MELRSLTSED TAVYYCTRWR SSMDYWGQGT SVTVSS      116

SEQ ID NO: 15           moltype = AA  length = 116
FEATURE                 Location/Qualifiers
source                  1..116
                        mol_type = protein
                        organism = Mus musculus
```

-continued

```
SEQUENCE: 15
EVQLQESGPE LVKPGASVKI PCKASGYTFT DYNMDWVKQS HGKSLEWIGD IDPNNGNTIY  60
NQKFKGKATL TVDKSSSTAY MELRSLTSED TAVYYCTKWR SSMDYWGQGT SVTVSS      116

SEQ ID NO: 16          moltype = AA  length = 231
FEATURE                Location/Qualifiers
source                 1..231
                       mol_type = protein
                       organism = Mus musculus
SEQUENCE: 16
EVQLQESGPE LVRPGASVKI PCKASGYTFT DYNMDWVMQS HGKSLEWIGD IDPNNGGTIY  60
NQKFKGKATL TVDKSSSTAY MELRSLTSED TAVYYCTRWR SSMDYWGQGT SVTVSEVQLQ  120
ESGPELVKPG ASVKIPCKAS GYTFTDYNVD WVKQSHGKSL EWIGDIDPNN GGTFYNQKFK  180
GKATLTVDKS SSTAHMELRS LTSEDTAVYY CVRWRSSMDY WGQGTSVTVS S           231

SEQ ID NO: 17          moltype = AA  length = 116
FEATURE                Location/Qualifiers
source                 1..116
                       mol_type = protein
                       organism = Mus musculus
SEQUENCE: 17
EVQLQESGPE LVKPGASVKI PCKASGYTFT DYNMDWVKQS HGKSLEWIGD IDPNTGTTFY  60
NQDFKGKATL TVDKSSSTAY MELRSLTSED TAVYYCARWR SSMDYWGQGT SLTVSS      116

SEQ ID NO: 18          moltype = AA  length = 120
FEATURE                Location/Qualifiers
source                 1..120
                       mol_type = protein
                       organism = Mus musculus
SEQUENCE: 18
EVQLQESGAE LVRPGASVTL SCKASGYTFT DYEMHWVKQT PVHGLEWIGV IDPGTGGTAY  60
NQKFKVKALL TADKSSNTAY MELRSLTSED SAVYYCTSEK FGSNYYFDYW GQGTTLTVSS  120

SEQ ID NO: 19          moltype = AA  length = 120
FEATURE                Location/Qualifiers
source                 1..120
                       mol_type = protein
                       organism = Mus musculus
SEQUENCE: 19
EVQLQESGAE LVRPGASVTL SCKASGYTFT DYEIHWVKQT PVHGLEWIGA IDPETGGTAY  60
NQKFKGKAIL TADKSSSTAY MELRSLTSED SAVYYCTSEK FGSSYYFDYW GQGTTFTVSS  120

SEQ ID NO: 20          moltype = AA  length = 118
FEATURE                Location/Qualifiers
source                 1..118
                       mol_type = protein
                       organism = Mus musculus
SEQUENCE: 20
EVQLQESGPG LVKPSQSLSL TCTVTGYSIT SDYAWNWIRQ FPGNKLEWMG YITYSGSPTY  60
NPSLKSQFSI TRDTSKNQFF LQLNSLTTED TATYYCARGL GGHYFDYWGQ GTTLTVSS    118

SEQ ID NO: 21          moltype = AA  length = 118
FEATURE                Location/Qualifiers
source                 1..118
                       mol_type = protein
                       organism = Mus musculus
SEQUENCE: 21
EVQLQESGPG LVKPSQSLSL TCTVTGYSIT SDYAWNWIRQ FPGNKLEWMG YITYSGSPTY  60
NPSLKSQFSI TRDTSKNQFF LQLNSVTTED TATYYCARGL GGHYFDYWGQ GTTLTVSS    118

SEQ ID NO: 22          moltype = AA  length = 117
FEATURE                Location/Qualifiers
source                 1..117
                       mol_type = protein
                       organism = Mus musculus
SEQUENCE: 22
EVQLQESGPD LVKPSQSLSL TCTVTGYSIT SGYSWHWIRQ FPGNKLEWMG FIHYSGDTNY  60
NPSLKSRFSI TRDTSKNQFF LHLNSVTPED TATYYCASPS RLLFDYWGHG TTLTVSS     117

SEQ ID NO: 23          moltype = AA  length = 113
FEATURE                Location/Qualifiers
source                 1..113
                       mol_type = protein
                       organism = Mus musculus
SEQUENCE: 23
EVQLQESGPG LVAPSQSLSI TCTVSGFSLT NYGVDWVRQS PGKGLEWLGV IWGVGSTNYN  60
SALKSRLSIS KDNSKSQVFL KMNSLQTDDT AMYYCASDGF VYWGQGTLVT VSS         113

SEQ ID NO: 24          moltype = AA  length = 113
```

```
FEATURE                Location/Qualifiers
source                 1..113
                       mol_type = protein
                       organism = Mus musculus
SEQUENCE: 24
EVQLQESGPG LVAPSQSLSI TCTVSGFSLT SYGVDWVRQS PGKGLEWLGV IWGIGSTNYN  60
SALKSRLSIS KDNSKSQVFL KMNSLQSDDT AMYYCASDGF VYWGQGTLVT VSS        113

SEQ ID NO: 25          moltype = AA  length = 114
FEATURE                Location/Qualifiers
source                 1..114
                       mol_type = protein
                       organism = Mus musculus
SEQUENCE: 25
EVQLQESGPS LVQPSQSLSI TCTVSGFSLT SYGVHWVRQS PGKGLEWLGV IWRGGNTDYN  60
AAFMSRLSIT KDNSKSQVFF KMNSLQADDT AIYYCAASMI GGYWGQGTTL TVSS       114

SEQ ID NO: 26          moltype = AA  length = 114
FEATURE                Location/Qualifiers
source                 1..114
                       mol_type = protein
                       organism = Mus musculus
SEQUENCE: 26
EVQLQESGPS LVQPSQSLSI TCTVSGFSLT NYGVHWVRQS PGKGLEWLGV IWRGGNTDYN  60
AAFMSRLSIT KDNSKSQVFF KFHSLQTDDT AIYYCAASMI GGYWGQGTTL TVSS       114

SEQ ID NO: 27          moltype = AA  length = 108
FEATURE                Location/Qualifiers
source                 1..108
                       mol_type = protein
                       organism = Mus musculus
SEQUENCE: 27
DIVLTQTPAI MSASPGEKVT LTCSASSSVS SNYLYWYQQR PGSSPKLWIY STSNLASGVP  60
ARFSGSGSGT SYSLTISSME AEDAASYFCH QWSSYPPTFG SGTKLEIK              108

SEQ ID NO: 28          moltype = AA  length = 108
FEATURE                Location/Qualifiers
source                 1..108
                       mol_type = protein
                       organism = Mus musculus
SEQUENCE: 28
DIVITQTTAI MSASPGEKVT LTCSASSSVS SNYLYWYQQR PGSSPKLWIY STSNLASGVP  60
ARFSGSGSGT SYSLTISSME AEDAASYFCH QWSSYPPTFG SGTKLEIK              108

SEQ ID NO: 29          moltype = AA  length = 108
FEATURE                Location/Qualifiers
source                 1..108
                       mol_type = protein
                       organism = Mus musculus
SEQUENCE: 29
DIVMTQTPAT MSASPGEKVT LTCSASSSVN SNYLYWYQQK PGSSPKVWIY STSNLASGVP  60
ARFSGSGSGT SYSLTISSME AEDAASYFCH QWSSYPPTFG SGTKLELK              108

SEQ ID NO: 30          moltype = AA  length = 108
FEATURE                Location/Qualifiers
source                 1..108
                       mol_type = protein
                       organism = Mus musculus
SEQUENCE: 30
DIVMTQTTAT MSASPGEKVT LTCSASSSVN SNYLYWYQQK PGSSPKVWIY STSNLASGVP  60
ARFSGSGSGT SYSLTISSME AEDAASYFCH QWSSYPPTFG SGTKLELK              108

SEQ ID NO: 31          moltype = AA  length = 108
FEATURE                Location/Qualifiers
source                 1..108
                       mol_type = protein
                       organism = Mus musculus
SEQUENCE: 31
DIVLTQSTAI MSASPGEKVT LTCSASSGVN SNYLYWYQQK PGSSPKLWIY STSNLASGVP  60
ARFSGSGSGT SYSLTISSVE AEDAASYFCH QWSSYPPTFG SGTKLEIK              108

SEQ ID NO: 32          moltype = AA  length = 107
FEATURE                Location/Qualifiers
source                 1..107
                       mol_type = protein
                       organism = Mus musculus
SEQUENCE: 32
DIVLTQTPSS LSASLGDRVT ISCSASQGIS NYLNWYQQKP DGTVKLLIYY TSSLHSGVPS  60
RFSGSGSGTD YSLTISNLEP EDIATYYCQQ YSKLPWTFGG GTKLEIK               107
```

```
SEQ ID NO: 33          moltype = AA  length = 107
FEATURE                Location/Qualifiers
source                 1..107
                       mol_type = protein
                       organism = Mus musculus
SEQUENCE: 33
DIVLTQSPSS LSASLGDRVT ISCSASQGIS NYLNWYQQKP DGTVKLLIYY TSSLHSGVPS  60
RFSGSGSGTD YSLTISNLEP EDIATYYCQQ YSKLPWTFGG GTKLEIK               107

SEQ ID NO: 34          moltype = AA  length = 107
FEATURE                Location/Qualifiers
source                 1..107
                       mol_type = protein
                       organism = Mus musculus
SEQUENCE: 34
DIVITQSPSS LSASLGDRVT ISCSASQGIS NYLNWYQQKP DGTVKLLIYY TSSLHSGVPS  60
RFSGSGSGTD YSLTISNLEP EDIATYYCQQ YSELPWTFGG GTKLEIK               107

SEQ ID NO: 35          moltype = AA  length = 107
FEATURE                Location/Qualifiers
source                 1..107
                       mol_type = protein
                       organism = Mus musculus
SEQUENCE: 35
DIVMTQSPSS LSASLGDRVT ISCSASQGIS NYLNWYQQRP DGTVKLLIYY TSSLHSGVPS  60
RFSGSGSGTD YSLTISNLEP EDIATYYCQQ YSNLPWTFGG GTKLEIK               107

SEQ ID NO: 36          moltype = AA  length = 107
FEATURE                Location/Qualifiers
source                 1..107
                       mol_type = protein
                       organism = Mus musculus
SEQUENCE: 36
DIVMTQSPSS LSASLGDRVT ISCSASQGIS NYLNWYQQKP DGTVKLLIYY TSSLHSGVPS  60
RFSGSGSGTD YSLTISNLEP EDIATYYCQQ YSELPWTFGG GTKLEIK               107

SEQ ID NO: 37          moltype = AA  length = 107
FEATURE                Location/Qualifiers
source                 1..107
                       mol_type = protein
                       organism = Mus musculus
SEQUENCE: 37
DIVMTQSTSS LSASLGDRVT ISCSASQGIS HYLNWYQQKP DGTVKLLIYY TSSLHSGVPS  60
RFSGSGSGTD YSLTIRNLEP EDIATYYCQQ YSELPWTFGG GTKLEIK               107

SEQ ID NO: 38          moltype = AA  length = 107
FEATURE                Location/Qualifiers
source                 1..107
                       mol_type = protein
                       organism = Mus musculus
SEQUENCE: 38
DIVMTQSPSS LSASLGDRVT ISCSASQGIS HYLNWYQQKP DGTVKLLIYY TSSLHSGVPS  60
RFSGSGSGTD YSLTIRNLEP EDIATYYCQQ YSELPWTFGG GTKLEIK               107

SEQ ID NO: 39          moltype = AA  length = 107
FEATURE                Location/Qualifiers
source                 1..107
                       mol_type = protein
                       organism = Mus musculus
SEQUENCE: 39
DIVMTQSPSS LSASLGDRVT ISCSASQDIS SYLNWYQQKP DGTVKLLIYY TSSLHSGVPS  60
RFSGSGSGTD YSLTISNLEP EDIATYYCQQ YSELPWTFGG GTKLEIK               107

SEQ ID NO: 40          moltype = AA  length = 107
FEATURE                Location/Qualifiers
source                 1..107
                       mol_type = protein
                       organism = Mus musculus
SEQUENCE: 40
DIVMTQTPSS LSASLGDRVT ISCSASQGIS YYLNWYQQKP DGTIKLLIYY TLSLHSGVPS  60
RFSGSGSGTD YSLTISNLEP EDIATYYCQQ YSELPWTFGG GTKLEIK               107

SEQ ID NO: 41          moltype = AA  length = 107
FEATURE                Location/Qualifiers
source                 1..107
                       mol_type = protein
                       organism = Mus musculus
SEQUENCE: 41
```

```
DIVMTQTPSS MSASLGDRVT ISCSASQGIS NYLNWYQQKP DGTVKLLIYY TSSLHSGVPS  60
RFSGSGSGTD YSLTISNLEP EDIATYYCQQ YSYLPWTFGG GTKLEIK              107

SEQ ID NO: 42          moltype = AA  length = 107
FEATURE                Location/Qualifiers
source                 1..107
                       mol_type = protein
                       organism = Mus musculus
SEQUENCE: 42
DIVMTQTPSS LSASLGDRVT ISCSASQGIG NYLNWYQQKP DGTVKLLIYY TSNLHSGVPS  60
RFSGRGSGTD YSLTISNLEP EDIATYYCQQ YSNLPWTFGG GTKLEIK              107

SEQ ID NO: 43          moltype = AA  length = 107
FEATURE                Location/Qualifiers
source                 1..107
                       mol_type = protein
                       organism = Mus musculus
SEQUENCE: 43
DIVMTQSPSS LSASLGDRVT ISCSASQGIS NYLNWYQQKP DGTVKLLIYY TSNLHSGVPS  60
RFSGSGSGTD YSLTISDLAP EDIATYYCQQ YSYLPWTFGG GTKLEIK              107

SEQ ID NO: 44          moltype = AA  length = 112
FEATURE                Location/Qualifiers
source                 1..112
                       mol_type = protein
                       organism = Mus musculus
SEQUENCE: 44
DIVITQSPLS LPVGLGDQAS ISCRSSQSLV HSNGNTYLHW YLQKPGQSPK LLIYKVSNRF  60
SGVPDRFSGS GSGTDFTLKI SRVEAEDLGV YFCSQSTHVP YTFGGGTKLE IK        112

SEQ ID NO: 45          moltype = AA  length = 112
FEATURE                Location/Qualifiers
source                 1..112
                       mol_type = protein
                       organism = Mus musculus
SEQUENCE: 45
DIVLTQTPLS LPVSLGDQAS ISCRSSQSIV HSNGNTYLEW YLQKPGQSPK LLIYKVSNRF  60
SGVPDRFSGS GSGTNFTLKI SRVEAEDLGV YYCFQGSHVP LTFGAGTKLE LK        112

SEQ ID NO: 46          moltype = AA  length = 112
FEATURE                Location/Qualifiers
source                 1..112
                       mol_type = protein
                       organism = Mus musculus
SEQUENCE: 46
DIVLTQSPLS LPVSLGDQAS ISCRSSQSIV HSDGNTYLEW YLQKPGQSPK LLIYKVSNRF  60
SGVPDRFSGS GSGTDFTLKI SRVEAEDLGI YYCFQGSHVP LTFGAGTKLE LK        112

SEQ ID NO: 47          moltype = AA  length = 112
FEATURE                Location/Qualifiers
source                 1..112
                       mol_type = protein
                       organism = Mus musculus
SEQUENCE: 47
DIVITQTPLS LPVSLGDQAS ISCRSSQTIV HSDGNTYLEW YLQKPGQSPK LLIYKVSNRF  60
SGVPDRFSGS GSGTDFTLKI SRVEAEDLGV YYCFQGSHVP LTFGAGTKLE IK        112

SEQ ID NO: 48          moltype = AA  length = 112
FEATURE                Location/Qualifiers
source                 1..112
                       mol_type = protein
                       organism = Mus musculus
SEQUENCE: 48
DIVMTQSTLS LPVSLGDQVS ISCRSSQSIV HSDGNTYLEW YLQKPGQSPN LLIYKVSNRF  60
SGVPDRFSGS GSGTDFTLKI SRVEAEDLGV YYCFQGSHVP LTFGAGTKLE LK        112

SEQ ID NO: 49          moltype = AA  length = 112
FEATURE                Location/Qualifiers
source                 1..112
                       mol_type = protein
                       organism = Mus musculus
SEQUENCE: 49
DIVLTQDELS NPVTSGESVS ISCRSSKSLL YKDGKTYLNW FLQRPGQSPQ VLIYFMSTRA  60
SGVSDRFSGS GSGTDFTLEI SRVKAEDVGV YYCQQLVDFP FTFGSGTKLE LK        112

SEQ ID NO: 50          moltype = AA  length = 112
FEATURE                Location/Qualifiers
source                 1..112
                       mol_type = protein
```

```
                          organism = Mus musculus
SEQUENCE: 50
DIVMTQDELY NPVTSGESVS ISCRSSKSLL YKDGKTYLNW FLQRPGQSPQ VLIYFMSTRA  60
SGVSDRFSGS GSGTDFTLEI SRVKAEDVGV YYCQQLVDFP FTFGSGTKLE IK          112

SEQ ID NO: 51             moltype = AA  length = 113
FEATURE                   Location/Qualifiers
source                    1..113
                          mol_type = protein
                          organism = Mus musculus
SEQUENCE: 51
DIVMTQSPSS LTVTAGEKVT MSCKSSQSLL NSGTQKNYLT WYQQKPGQPP KLLIYWASTR  60
ESGVPDRFTG SGSGTDFTLT ISSVQAEDLA VYYCQNDYSY PLTFGAGTKL EIK         113

SEQ ID NO: 52             moltype = AA  length = 107
FEATURE                   Location/Qualifiers
source                    1..107
                          mol_type = protein
                          organism = Mus musculus
SEQUENCE: 52
DIVLTQTTAT LSVTPGDRVS LSCRASQSIS DYLHWYQQKS HESPRLLIKY ASQSISGIPS  60
RFSGSGSGSD FTLTVNSVEP EDVGVYYCQN GHSYPYTFGG GTKLEIK                107

SEQ ID NO: 53             moltype = AA  length = 107
FEATURE                   Location/Qualifiers
source                    1..107
                          mol_type = protein
                          organism = Mus musculus
SEQUENCE: 53
DIVLTQSPDT LSVTPGDRVS LSCRASQSIS DYLHWYQQKS HESPRLLIKY ASQSISGIPS  60
RFSGSGSGSD FTLSINSVEP EDVGVYYCQN GHSYPYTFGG GTKLELK                107

SEQ ID NO: 54             moltype = AA  length = 15
FEATURE                   Location/Qualifiers
REGION                    1..15
                          note = PD-1 peptide sequence
source                    1..15
                          mol_type = protein
                          organism = synthetic construct
SEQUENCE: 54
MQIPQAPWPV VWAVL                                                   15

SEQ ID NO: 55             moltype = AA  length = 15
FEATURE                   Location/Qualifiers
REGION                    1..15
                          note = PD-1 peptide sequence
source                    1..15
                          mol_type = protein
                          organism = synthetic construct
SEQUENCE: 55
APWPVVWAVL QLGWR                                                   15

SEQ ID NO: 56             moltype = AA  length = 15
FEATURE                   Location/Qualifiers
REGION                    1..15
                          note = PD-1 peptide sequence
source                    1..15
                          mol_type = protein
                          organism = synthetic construct
SEQUENCE: 56
VWAVLQLGWR PGWFL                                                   15

SEQ ID NO: 57             moltype = AA  length = 15
FEATURE                   Location/Qualifiers
REGION                    1..15
                          note = PD-1 peptide sequence
source                    1..15
                          mol_type = protein
                          organism = synthetic construct
SEQUENCE: 57
QLGWRPGWFL DSPDR                                                   15

SEQ ID NO: 58             moltype = AA  length = 15
FEATURE                   Location/Qualifiers
REGION                    1..15
                          note = PD-1 peptide sequence
source                    1..15
                          mol_type = protein
                          organism = synthetic construct
```

```
SEQUENCE: 58
PGWFLDSPDR PWNPP                                              15

SEQ ID NO: 59          moltype = AA  length = 15
FEATURE                Location/Qualifiers
REGION                 1..15
                       note = PD-1 peptide sequence
source                 1..15
                       mol_type = protein
                       organism = synthetic construct
SEQUENCE: 59
DSPDRPWNPP TFSPA                                              15

SEQ ID NO: 60          moltype = AA  length = 15
FEATURE                Location/Qualifiers
REGION                 1..15
                       note = PD-1 peptide sequence
source                 1..15
                       mol_type = protein
                       organism = synthetic construct
SEQUENCE: 60
PWNPPTFSPA LLVVT                                              15

SEQ ID NO: 61          moltype = AA  length = 15
FEATURE                Location/Qualifiers
REGION                 1..15
                       note = PD-1 peptide sequence
source                 1..15
                       mol_type = protein
                       organism = synthetic construct
SEQUENCE: 61
TFSPALLVVT EGDNA                                              15

SEQ ID NO: 62          moltype = AA  length = 15
FEATURE                Location/Qualifiers
REGION                 1..15
                       note = PD-1 peptide sequence
source                 1..15
                       mol_type = protein
                       organism = synthetic construct
SEQUENCE: 62
LLVVTEGDNA TFTCS                                              15

SEQ ID NO: 63          moltype = AA  length = 15
FEATURE                Location/Qualifiers
REGION                 1..15
                       note = PD-1 peptide sequence
source                 1..15
                       mol_type = protein
                       organism = synthetic construct
SEQUENCE: 63
EGDNATFTCS FSNTS                                              15

SEQ ID NO: 64          moltype = AA  length = 15
FEATURE                Location/Qualifiers
REGION                 1..15
                       note = PD-1 peptide sequence
source                 1..15
                       mol_type = protein
                       organism = synthetic construct
SEQUENCE: 64
TFTCSFSNTS ESFVL                                              15

SEQ ID NO: 65          moltype = AA  length = 15
FEATURE                Location/Qualifiers
REGION                 1..15
                       note = PD-1 peptide sequence
source                 1..15
                       mol_type = protein
                       organism = synthetic construct
SEQUENCE: 65
FSNTSESFVL NWYRM                                              15

SEQ ID NO: 66          moltype = AA  length = 15
FEATURE                Location/Qualifiers
REGION                 1..15
                       note = PD-1 peptide sequence
source                 1..15
                       mol_type = protein
```

```
                        organism = synthetic construct
SEQUENCE: 66
ESFVLNWYRM SPSNQ                                                     15

SEQ ID NO: 67           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 67
NWYRMSPSNQ TDKLA                                                     15

SEQ ID NO: 68           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 68
SPSNQTDKLA AFPED                                                     15

SEQ ID NO: 69           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 69
TDKLAAFPED RSQPG                                                     15

SEQ ID NO: 70           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 70
AFPEDRSQPG QDCRF                                                     15

SEQ ID NO: 71           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 71
RSQPGQDCRF RVTQL                                                     15

SEQ ID NO: 72           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 72
QDCRFRVTQL PNGRD                                                     15

SEQ ID NO: 73           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 73
RVTQLPNGRD FHMSV                                                     15

SEQ ID NO: 74           moltype = AA  length = 15
FEATURE                 Location/Qualifiers
REGION                  1..15
                        note = PD-1 peptide sequence
source                  1..15
```

```
                        mol_type = protein
                        organism = synthetic construct
SEQUENCE: 74
PNGRDFHMSV VRARR                                                15

SEQ ID NO: 75           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 75
FHMSVVRARR NDSGT                                                15

SEQ ID NO: 76           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 76
VRARRNDSGT YLCGA                                                15

SEQ ID NO: 77           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 77
NDSGTYLCGA ISLAP                                                15

SEQ ID NO: 78           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 78
YLCGAISLAP KAQIK                                                15

SEQ ID NO: 79           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 79
ISLAPKAQIK ESLRA                                                15

SEQ ID NO: 80           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 80
KAQIKESLRA ELRVT                                                15

SEQ ID NO: 81           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 81
ESLRAELRVT ERRAE                                                15

SEQ ID NO: 82           moltype = AA  length = 15
FEATURE                 Location/Qualifiers
REGION                  1..15
                        note = PD-1 peptide sequence
```

```
source                  1..15
                        mol_type = protein
                        organism = synthetic construct
SEQUENCE: 82
ELRVTERRAE VPTAH                                                     15

SEQ ID NO: 83           moltype = AA  length = 15
FEATURE                 Location/Qualifiers
REGION                  1..15
                        note = PD-1 peptide sequence
source                  1..15
                        mol_type = protein
                        organism = synthetic construct
SEQUENCE: 83
ERRAEVPTAH PSPSP                                                     15

SEQ ID NO: 84           moltype = AA  length = 16
FEATURE                 Location/Qualifiers
REGION                  1..16
                        note = PD-1 peptide sequence
source                  1..16
                        mol_type = protein
                        organism = synthetic construct
SEQUENCE: 84
VPTAHPSPSP RPAGQF                                                    16

SEQ ID NO: 85           moltype = AA  length = 120
FEATURE                 Location/Qualifiers
REGION                  1..120
                        note = humanized-heavy chain variable region
source                  1..120
                        mol_type = protein
                        organism = synthetic construct
SEQUENCE: 85
QVQLVQSGAE VKKPGASVKV SCKASGYTFT SYWMHWVRQA PGQGLEWMGM IDPSNSETSL  60
NQKFQGRVTM TVDKSTNTVY MELSSLRSED TAVYYCARSR GNYAYEMDYW GQGTLVTVSS  120

SEQ ID NO: 86           moltype = AA  length = 120
FEATURE                 Location/Qualifiers
REGION                  1..120
                        note = humanized-heavy chain variable region
source                  1..120
                        mol_type = protein
                        organism = synthetic construct
SEQUENCE: 86
EVQLVQSGAE VKKPGASVKV SCKASGYTFT SYWMHWVRQA PGQGLEWMGM IDPSNSETSL  60
NQKFQGRVTL NVDKSTNTAY MELSSLRSED TAVYYCARSR GNYAYEMDYW GQGTLVTVSS  120

SEQ ID NO: 87           moltype = AA  length = 120
FEATURE                 Location/Qualifiers
REGION                  1..120
                        note = humanized-heavy chain variable region
source                  1..120
                        mol_type = protein
                        organism = synthetic construct
SEQUENCE: 87
EVQLVQSGTE VTKPGASVKV SCKASGYTFT SYWMHWVRQA PGQGLEWLGM IDPSNSETTL  60
NQKFQGRVTM TVDKSTNTVY MELTSLRSED TAVYYCARSR GNYAYEMDYW GQGTLVTVSS  120

SEQ ID NO: 88           moltype = AA  length = 120
FEATURE                 Location/Qualifiers
REGION                  1..120
                        note = humanized-heavy chain variable region
source                  1..120
                        mol_type = protein
                        organism = synthetic construct
SEQUENCE: 88
EVQLVQSGAE VKKPGASVKV SCKASGYTFT DYEMHWVRQA PGQGLEWMGI IDPGTGGTAY  60
NQKFQGRVTM TADKSTSTVY MELSSLRSED TAVYYCTSEK FGSNYYFDYW GQGTLVTVSS  120

SEQ ID NO: 89           moltype = AA  length = 120
FEATURE                 Location/Qualifiers
REGION                  1..120
                        note = humanized-heavy chain variable region
source                  1..120
                        mol_type = protein
                        organism = synthetic construct
SEQUENCE: 89
EVQLVQSGAE VKKPGASVKV SCKASGYTFT DYEMHWVRQA PGQGLEWMGI IDPGTGGTAY  60
```

```
NQKFQGRVTM TADKSTNTVY MELSSLRSED TAVYYCTSEK FGSNYYFDYW GQGTLVTVSS  120

SEQ ID NO: 90          moltype = AA  length = 120
FEATURE                Location/Qualifiers
REGION                 1..120
                       note = humanized-heavy chain variable region
source                 1..120
                       mol_type = protein
                       organism = synthetic construct
SEQUENCE: 90
EVQLVQSGAE VKKPGASVKV SCKASGYTFT DYEMHWVRQA PGQRLEWMGV IDPGTGGTAY  60
NQKFQGRVTI TADKSASTAY MELSSLRSED TAVYYCTSEK FGSNYYFDYW GQGTLVTVSS  120

SEQ ID NO: 91          moltype = AA  length = 108
FEATURE                Location/Qualifiers
REGION                 1..108
                       note = humanized-light chain variable region
source                 1..108
                       mol_type = protein
                       organism = synthetic construct
SEQUENCE: 91
EIVLTQSPAT LSLSPGERAT LSCRASSSVS SNYLYWYQQK PGQAPRLLIY STSNRATGIP  60
ARFSGSGSGT DYTLTISSLE PEDFAVYYCH QWSSYPPTFG QGTKLEIK               108

SEQ ID NO: 92          moltype = AA  length = 108
FEATURE                Location/Qualifiers
REGION                 1..108
                       note = humanized-light chain variable region
source                 1..108
                       mol_type = protein
                       organism = synthetic construct
SEQUENCE: 92
DIVLTQSPAT LSLSPGERAT LSCRASSSVS SNYLYWYQQK PGQAPRLLIY STSNLATGIP  60
ARFSGSGSGT DYTLTISSLE PEDFAVYFCH QWSSYPPTFG QGTKLEIK               108

SEQ ID NO: 93          moltype = AA  length = 108
FEATURE                Location/Qualifiers
REGION                 1..108
                       note = humanized-light chain variable region
source                 1..108
                       mol_type = protein
                       organism = synthetic construct
SEQUENCE: 93
DIVLTQSPGT LSLSPGEKVT LSCRASSSVS SNYLYWYQQK PGQAPRLVIY STSNLATGIP  60
DRFSGSGSGT DYTLTISRLE PEDFAVYFCH QWSSYPPTFG QGTKVEIK               108

SEQ ID NO: 94          moltype = AA  length = 112
FEATURE                Location/Qualifiers
REGION                 1..112
                       note = humanized-light chain variable region
source                 1..112
                       mol_type = protein
                       organism = synthetic construct
SEQUENCE: 94
DVVMTQSPLS LPVTLGQPAS ISCRSSQTIV HSDGNTYLEW YQQRPGQSPR LLIYKVSNRF  60
SGVPDRFSGS GSGTDFTLKI SRVEAEDVGV YYCFQGSHVP LTFGQGTKLE IK          112

SEQ ID NO: 95          moltype = AA  length = 112
FEATURE                Location/Qualifiers
REGION                 1..112
                       note = humanized-light chain variable region
source                 1..112
                       mol_type = protein
                       organism = synthetic construct
SEQUENCE: 95
DIVMTQSPLS LPVTLGQPAS ISCRSSQTIV HSDGNTYLEW YQQRPGQSPK LLIYKVSNRF  60
SGVPDRFSGS GSGTDFTLKI SRVEAEDVGV YYCFQGSHVP LTFGQGTKLE IK          112

SEQ ID NO: 96          moltype = AA  length = 112
FEATURE                Location/Qualifiers
REGION                 1..112
                       note = humanized-light chain variable region
source                 1..112
                       mol_type = protein
                       organism = synthetic construct
SEQUENCE: 96
DIVMTQTPLS SPVTLGQPAS ISCRSSQTIV HSDGNTYLEW YQQRPGQPPR LLIYKVSNRF  60
SGVPDRFSGS GAGTDFTLKI SRVEAEDVGV YYCFQGSHVP LTFGQGTKLE IK          112
```

-continued

```
SEQ ID NO: 97          moltype = AA  length = 143
FEATURE                Location/Qualifiers
source                 1..143
                       mol_type = protein
                       organism = Mus musculus
SEQUENCE: 97
PDRPWNPPTF SPALLVVTEG DNATFTCSFS NTSESFVLNW YRMSPSNQTD KLAAFPEDRS  60
QPGQDCRFRV TQLPNGRDFH MSVVRARRND SGTYLCGAIS LAPKAQIKES LRAELRVTER  120
RAEVPTAHPS PSPRPAGQFQ TVV                                          143
```

ANTI-PD-1 ANTIBODIES

RELATED APPLICATIONS

This application is a divisional of U.S. application Ser. No. 16/728,653, filed on Dec. 27, 2019, which is a continuation of U.S. application Ser. No. 15/152,192, filed May 11, 2016, now U.S. Pat. No. 10,544,217, issued Jan. 28, 2020, which is a divisional of U.S. application Ser. No. 14/975,769, filed Dec. 19, 2015, now U.S. Pat. No. 10,239,942, which claims the benefit of U.S. Provisional Application No. 62/095,675, filed on Dec. 22, 2014, U.S. Provisional Application No. 62/220,199, filed on Sep. 17, 2015, U.S. Provisional Application No. 62/251,082, filed on Nov. 4, 2015, and U.S. Provisional Application No. 62/261,118, filed on Nov. 30, 2015. The entire teachings of the above applications are incorporated herein by reference.

INCORPORATION BY REFERENCE OF MATERIAL IN XML

This application incorporates by reference the Sequence Listing contained in the following eXtensible Markup Language (XML) file being submitted concurrently herewith:

a) File name: 50911000025_Sequence_Listing.xml; created Mar. 23, 2023, 108,275 Bytes n size.

BACKGROUND OF THE INVENTION

Modulation of the mammalian adaptive immune response (immunomodulation) is a useful therapeutic approach for various diseases and disorders. One way to achieve such immunomodulation is to intervene at one or more immune checkpoints, e.g., the Programmed Death-1 (PD-1) checkpoint. The natural function of immune checkpoints is to suppress the immune response, as necessary, to prevent immune damage to normal tissue. Depending on the disease or disorder, it may be desirable to upregulate or downregulate the immune response. Tumor cells that display non-self-antigens can evade immune attack by secreting cytokines or ligands that activate immune checkpoints. Therefore, in cancer therapy, it is generally desirable to upregulate the immune response against tumor cells. In contrast, in treatment of autoimmune diseases, it is generally desirable to downregulate the immune response in certain tissues.

"Programmed Death-1" (PD-1) protein (also known as Programmed Cell Death Protein 1 and CD279) is a type I transmembrane receptor that is part of the extended CD28/CTLA4 family of T cell regulators. Ligands for PD-1 include PD-1 Ligand 1 (PD-L1, also known as B7-H1), and PD-1 Ligand 2 (PD-L2, also known as B7-DC).

PD-1 is expressed on various cell types, including T cells, B cells, and macrophages. Experimental data implicate the interactions of PD-1 with its ligands in downregulation of central and peripheral immune responses. Proliferation of T cells is inhibited in the presence of PD-L1. Mice with a disrupted PD-1 gene exhibit an autoimmune phenotype. PD-1 deficiency in the C57BL/6 mice results in chronic progressive lupus-like glomerulonephritis and arthritis (Nishimura et al., *J. Exp. Med.* 101(5):891-98, 2000).

Compounds that modulate PD-1 activity have potential as therapeutic agents for the treatment of various diseases and disorders, including cancer, inflammation, and autoimmune diseases. There is a significant unmet need for immunomodulatory compounds, e.g., antibodies, including PD-1 agonists and PD-1 antagonists.

SUMMARY OF THE INVENTION

The present invention provides antibodies that bind to PD-1. In some embodiments, the invention provides an isolated antibody that binds to PD-1, comprising a heavy chain variable region (HCVR) selected from the group consisting of SEQ ID NOs: 1-26 and/or a light chain variable region (LCVR) selected from the group consisting of SEQ ID NOs: 27-53. The invention also provides an isolated antibody that binds to PD-1 and competitively inhibits the binding of any of the antibodies disclosed herein to PD-1.

In some embodiments, the invention also provides an isolated antibody that binds to PD-1, comprising a HCVR selected from the group consisting of SEQ ID NOs: 85-90 and/or a LCVR selected from the group consisting of SEQ ID NOs: 91-96.

The invention further provides an isolated antibody that binds to PD-1, wherein the antibody binds to a sequence in PD-1 selected from the group consisting of SEQ ID NOs: 54-84.

The antibodies can be used as therapeutic agents. For use as therapeutic agents, the antibodies disclosed herein can be engineered, e.g., humanized, to reduce or eliminate serum sickness or an undesired immune response when administered to a human patient. Also disclosed are methods of treating diseases and disorders in which the PD-1 signaling pathway plays a significant role ("PD-1-mediated diseases and disorders").

The present invention includes the surprising discovery that contacting human T cells with an effective amount of an anti-PD-1 antibody that competitively inhibits binding of PD-L1 or PD-L2 to PD-1 expressed on the surface of T cells, and an effective amount of an anti-PD-1 antibody that does not competitively inhibit binding of PD-L1 or PD-L2 to PD-1 expressed on the surface of the T cells increases T cell effector function to a greater extent than an equivalent amount of either anti-PD-1 antibody alone. In some embodiments, the combination yields an additive effect on T cell effector function. In some embodiments, the combination yields a synergistic effect on T cell effector function.

Accordingly, the present invention provides a method for increasing T cell effector function, comprising contacting a T cell with a combination of: (a) an effective amount of an anti-PD-1 antibody that competitively inhibits binding of PD-L1 or PD-L2 to PD-1 expressed on the surface of the T cell; and (b) an effective amount of an anti-PD-1 antibody that does not competitively inhibit binding of PD-L1 or PD-L2 to PD-1 expressed on the surface of the T cell.

In some embodiments, the present invention also provides a method for increasing T cell effector function, comprising contacting a T cell with an anti-PD-1 antibody that does not competitively inhibit binding of PD-L1 or PD-L2 to PD-1 expressed on the surface of the T cell.

Additionally, the present invention provides a method for increasing lymphocyte secretion of a cytokine selected from the group consisting of IL-6, IL-12, IL-18, TNF-α, IL-1β and GM-CSF in a human patient in need of increased T cell effector function, comprising administering to the patient a therapeutically effective amount of an anti-PD-1 antibody that does not competitively inhibit binding of PD-L1 or PD-L2 to PD-1 expressed on the surface of a T cell.

The present invention provides a method of treating cancer in a mammal, comprising contacting a T cell in a mammal in need thereof with a combination of: (a) an effective amount of an anti-PD-1 antibody that competitively inhibits binding of PD-L1 or PD-L2 to PD-1 expressed on the surface of the T cell; and (b) an effective amount of an anti-PD-1 antibody that does not competitively inhibit binding of PD-L1 or PD-L2 to PD-1 expressed on the surface of the T cell.

The present invention provides a method of producing anti-PD-1 antibodies comprising a HCVR, a LCVR, or a combination thereof. Accordingly, also provided herein is an isolated nucleic acid comprising a nucleotide sequence encoding the HCVR and/or LCVR of the present disclosure, as well as a host cell comprising an isolated nucleic acid of the invention.

The antibodies of the present invention can also be used in diagnostic testing. For example, the invention provides a method of diagnosing a PD-1-mediated disease or disorder, e.g., adaptive immune resistance, in a patient who has cancer.

These and other aspects and advantages of the invention will become apparent upon consideration of the following figures, detailed description and claims. As used herein, "including" means without limitation, and the examples cited are non-limiting.

BRIEF DESCRIPTION OF THE DRAWINGS

The invention can be more completely understood with reference to the following drawings.

FIGS. 7A and 7B summarize the results of mixed lymphocyte reaction assays using anti-PD-1 antibodies and human PBMCs. Humanized versions of clone 388D4 ("D4-HC3+LC1"; "D4-HC1+LC3"; and "D4-HC3+LC3") appear to induce cytokine release (FIG. 7A) and CD25 upregulation (FIG. 7B) similar to nivolumab. Humanized versions of clone 244C8 ("C8-HC1+LC1"; "C8-HC1+LC3"; and "C8-HC2+LC1") appear to induce increased levels of cytokine release (IFNγ) compared with 388D4 or nivolumab (FIG. 7A). T cells incubated with 244C8 also appear to exhibit a higher degree of activation, as inferred from CD25 expression (FIG. 7B).

FIG. 8 indicates regions within the PD-1 amino acid sequence (SEQ ID NO:97) bound by certain antibodies of the present invention (246A10, 244C8, 388D4, 413D2, and 413E1), as determined by peptide mapping. The PD-1 amino acid sequences corresponding to the sequences of inhibitory peptides are underlined.

FIGS. 10A and 10B are amino acid sequence alignments of humanized and mouse antibody sequences. FIG. 10A shows alignments for 100388 D4 VH3 (mouse) with humanized heavy chain variable regions (100388_D4_HC1; 100388_D4_HC2; and 100388_D4_HC3) and 100389_D4_VK5 (mouse) with humanized light chain variable regions (100389_D4_LC1; 100389_D4_LC2; and 100389_D4_LC3). FIG. 10B shows alignments for 100244_C8_VH3 (mouse) with humanized heavy chain variable regions (100244_C8_HC1; 100244_C8_HC2; and 100244_C8_HC3) and 100245_C8_VK5m1 (mouse) with humanized light chain variable regions (100245_C8_LC1; 100245_C8_LC2; and 100245_C8_LC3).

FIG. 11A shows data from FACS analysis of anti-PD-1 antibody EH12.2H7 (positive control); FIG. 11B shows data from FACS analysis of anti-PD-1 antibody mIgG1K (negative control); FIG. 11C shows data from FACS analysis of anti-PD-1 antibody 388D4; FIG. 11D shows data from FACS analysis of anti-PD-1 antibody 244C8.

As shown in FIG. 13, treatment with 244C8-2 alone increased IFNγ 1.77-fold (±0.19 sd), while treatment with 244C8-2 in combination with 388D4-2 increased IFNγ secretion 2.11-fold (±0.21 sd).

(FIG. 15A, IL-6; FIG. 15B, IL-12; FIG. 15C, IL-18; FIG. 15D TNF-α; FIG. 15E, IL-1β; FIG. 15F, GM-CSF)

(FIG. 16A, IL-6; FIG. 16B, IL-12; FIG. 16C, IL-18; FIG. 16D TNF-α; FIG. 16E, IL-1β; FIG. 16F, GM-CSF).

As shown in FIG. 17A, no significant difference in tumor growth inhibition was observed among treatment with antibody 388D4-3, antibody 244C8-2, pembrolizumab, or the combination of antibody 244C8-2 with pembrolizumab. FIG. 17B is a boxplot of tumor volumes for each treatment arm at day 28 (end of study) of the experiment described in FIG. 17A. The tumor volume for each treatment group was significantly smaller than that of the vehicle group. Student T-test p values between each treatment group and vehicle group were: 0.00167 (pembrolizumab), 0.00105 (388D4-3), 0.00277 (244C8-2), and 0.00275 (pembrolizumab+244C8), respectively. FIG. 17C is a histogram showing percentage tumor volume of each treatment group relative to vehicle on day 28 of the experiment described in FIGS. 17A and 17B. The calculated percent tumor growth inhibition (% TGI) for each treatment is shown above each bar.

DETAILED DESCRIPTION OF THE INVENTION

Figure 1:
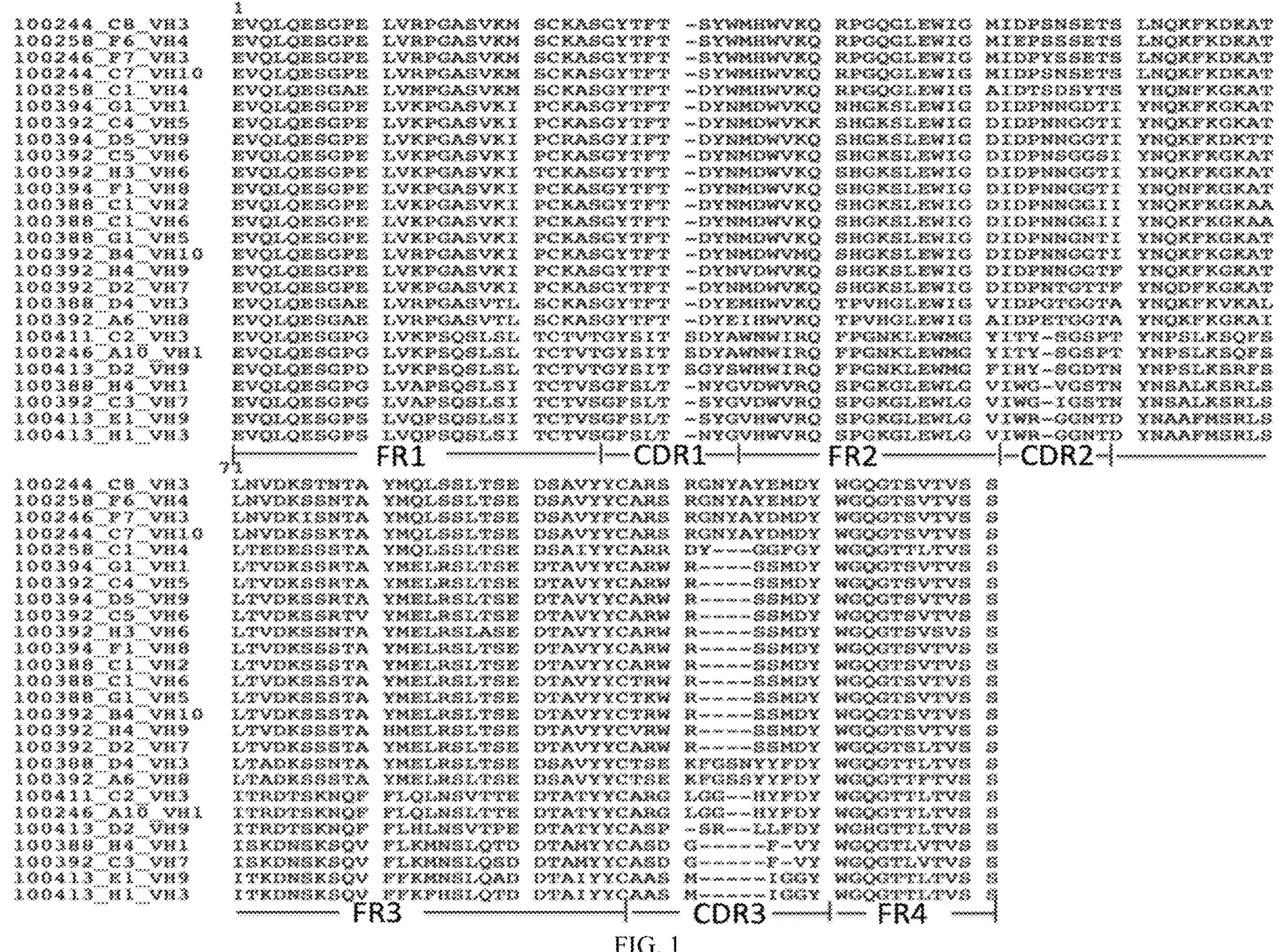
FIG. 1 is an alignment of the sequences of 26 heavy chain variable regions (HCVR) from antibodies that bind to human PD-1. The lower segment of the sequences is a continuation of the upper segment. Framework regions FR1 through FR4 are indicated. Complementarity determining regions CDR1 through CDR3 are also shown.

The anti-PD-1 antibodies disclosed herein are based on the antigen binding sites of certain monoclonal antibodies selected on the basis of binding to human Programmed Death-1 (PD-1) protein (UniProt #Q15116). The antibodies contain immunoglobulin variable region CDR sequences that define binding sites for human PD-1.

By virtue of the PD-1 signal blocking or PD-1 neutralizing activity of certain of these antibodies, they are useful for treating various types of cancer, including inhibiting tumor growth. In some embodiments (e.g., when used as therapeutic agents), the antibodies can be engineered to minimize or eliminate an immune response when administered to a human patient. Various features and aspects of the invention are discussed in more detail below.

As used herein, "isolated antibody" means an antibody that is substantially free of its natural environment. For instance, an isolated antibody or nucleic acid is substantially free of cellular material and other proteins from the cell or tissue source from which it is derived.

As used herein, unless otherwise indicated, "antibody" means an intact antibody or antigen-binding fragment of an antibody, including an intact antibody or antigen-binding fragment that has been modified or engineered, or that is a human antibody. Examples of antibodies that have been modified or engineered are chimeric antibodies, humanized antibodies, multiparatopic antibodies (e.g., biparatopic antibodies), and multispecific antibodies (e.g., bispecific antibodies). Examples of antigen-binding fragments include Fab, Fab', $F(ab')_2$, Fv, single chain antibodies (e.g., scFv), minibodies and diabodies.

The antibodies disclosed herein comprise: (a) an immunoglobulin heavy chain variable region comprising the structure $CDR_{H1}$-$CDR_{H2}$-$CDR_{H3}$, and (b) an immunoglobulin light chain variable region comprising the structure $CDR_{L1}$-$CDR_{L2}$-$CDR_{L3}$, wherein the heavy chain variable region and the light chain variable region together define a single binding site for binding human PD-1 protein.

In some embodiments, the isolated antibody that binds to PD-1 comprises a heavy chain variable region (HCVR) having complementarity determining regions (CDRs) selected from the group consisting of: CDRs 1-3 of SEQ ID NO: 1; CDRs 1-3 of SEQ ID NO: 2; CDRs 1-3 of SEQ ID NO: 3; CDRs 1-3 of SEQ ID NO: 4; CDRs 1-3 of SEQ ID NO: 5; CDRs 1-3 of SEQ ID NO: 6; CDRs 1-3 of SEQ ID NO: 7; CDRs 1-3 of SEQ ID NO: 8; CDRs 1-3 of SEQ ID NO: 9; CDRs 1-3 of SEQ ID NO: 10; CDRs 1-3 of SEQ ID NO: 11; CDRs 1-3 of SEQ ID NO: 12; CDRs 1-3 of SEQ ID NO: 13; CDRs 1-3 of SEQ ID NO: 14; CDRs 1-3 of SEQ ID NO: 15; CDRs 1-3 of SEQ ID NO: 16; CDRs 1-3 of SEQ ID NO: 17; CDRs 1-3 of SEQ ID NO: 18; CDRs 1-3 of SEQ ID NO: 19; CDRs 1-3 of SEQ ID NO: 20; CDRs 1-3 of SEQ ID NO: 21; CDRs 1-3 of SEQ ID NO: 22; CDRs 1-3 of SEQ ID NO: 23; CDRs 1-3 of SEQ ID NO: 24; CDRs 1-3 of SEQ ID NO: 25; and CDRs 1-3 of SEQ ID NO: 26.

In some embodiments, the isolated antibody that binds to PD-1 comprises a HCVR selected from the group consisting of SEQ ID NOs: 1-26.

In some embodiments, the isolated antibody that binds to PD-1 comprises a light chain variable region (LCVR) having CDRs selected from the group consisting of: CDRs 1-3 of SEQ ID NO: 27; CDRs 1-3 of SEQ ID NO: 28; CDRs 1-3 of SEQ ID NO: 29; CDRs 1-3 of SEQ ID NO: 30; CDRs 1-3 of SEQ ID NO: 31; CDRs 1-3 of SEQ ID NO: 32; CDRs 1-3 of SEQ ID NO: 33; CDRs 1-3 of SEQ ID NO: 34; CDRs 1-3 of SEQ ID NO: 35; CDRs 1-3 of SEQ ID NO: 36; CDRs 1-3 of SEQ ID NO: 37; CDRs 1-3 of SEQ ID NO: 38; CDRs 1-3 of SEQ ID NO: 39; CDRs 1-3 of SEQ ID NO: 40; CDRs 1-3 of SEQ ID NO: 41; CDRs 1-3 of SEQ ID NO: 42; CDRs 1-3 of SEQ ID NO: 43; CDRs 1-3 of SEQ ID NO: 44; CDRs 1-3 of SEQ ID NO: 45; CDRs 1-3 of SEQ ID NO: 46; CDRs 1-3 of SEQ ID NO: 47; CDRs 1-3 of SEQ ID NO: 48; CDRs 1-3 of SEQ ID NO: 49; CDRs 1-3 of SEQ ID NO: 50; CDRs 1-3 of SEQ ID NO: 51; CDRs 1-3 of SEQ ID NO: 52; and CDRs 1-3 of SEQ ID NO: 53.

In some embodiments, the isolated antibody that binds to PD-1 comprises a LCVR selected from the group consisting of SEQ ID NOs: 27-53.

In some embodiments, the isolated antibody that binds to PD-1 comprises a HCVR selected from the group consisting of SEQ ID NOs: 1-26 and a LCVR selected from the group consisting of SEQ ID NOs: 27-53. Examples of pairings of HCVR and LCVR are provided throughout the present disclosure, but additional functional pairings are within the scope of the invention.

In some embodiments, the antibody comprises a HCVR having the sequence set forth in SEQ ID NO: 4 and a LCVR having the sequence set forth in SEQ ID NO: 28 (designated as 244C7 in Table 3); a HCVR having the sequence set forth in SEQ ID NO: 4 and a LCVR having the sequence set forth in SEQ ID NO: 27 (244C7m1); a HCVR having the sequence set forth in SEQ ID NO: 1 and a LCVR having the sequence set forth in SEQ ID NO: 28 (244C8); a HCVR having the sequence set forth in SEQ ID NO: 1 and a LCVR having the sequence set forth in SEQ ID NO: 27 (244C8m1); a HCVR having the sequence set forth in SEQ ID NO: 3 and a LCVR having the sequence set forth in SEQ ID NO: 31 (246F7); a HCVR having the sequence set forth in SEQ ID NO: 5 and a LCVR having the sequence set forth in SEQ ID NO: 44 (258C1); a HCVR having the sequence set forth in SEQ ID NO: 2 and a LCVR having the sequence set forth in SEQ ID NO: 30 (258F6); a HCVR having the sequence set forth in SEQ ID NO: 2 and a LCVR having the sequence set forth in SEQ ID NO: 29 (258F6m); a HCVR having the sequence set forth in SEQ ID NO: 6 and a LCVR having the sequence set forth in SEQ ID NO: 34 (392C4); a HCVR having the sequence set forth in SEQ ID NO: 7 and a LCVR having the sequence set forth in SEQ ID NO: 41 (394D5); a HCVR having the sequence set forth in SEQ ID NO: 8 and a LCVR having the sequence set forth in SEQ ID NO: 35 (394G1); a HCVR having the sequence set forth in SEQ ID NO: 12 and a LCVR having the sequence set forth in SEQ ID NO: 39 (388C12A); a HCVR having the sequence set forth in SEQ ID NO: 12 and a LCVR having the sequence set forth in SEQ ID NO: 32 (388C12B); a HCVR having the sequence set forth in SEQ ID NO: 13 and a LCVR having the sequence set forth in SEQ ID NO: 39 (388C16A); a HCVR having the sequence set forth in SEQ ID NO: 13 and a LCVR having the sequence set forth in SEQ ID NO: 32 (388C16B); a HCVR having the sequence set forth in SEQ ID NO: 9 and a LCVR having the sequence set forth in SEQ ID NO: 38 (392C5A); a HCVR having the sequence set forth in SEQ ID NO: 9 and a LCVR having the sequence set forth in SEQ ID NO: 37 (392C5B); a HCVR having the sequence set forth in SEQ ID NO: 17 and a LCVR having the sequence set forth in SEQ ID NO: 40 (392D2); a HCVR having the sequence set forth in SEQ ID NO: 16 and a LCVR having the sequence set forth in SEQ ID NO: 43 (392H4); a HCVR having the sequence set forth in SEQ ID NO: 20 and a LCVR having the sequence set forth in SEQ ID NO: 53 (246A10); a HCVR having the sequence set forth in SEQ ID NO: 18 and a LCVR having the sequence set forth in SEQ ID NO: 47 (388D4); a HCVR having the sequence set forth in SEQ ID NO: 19 and a LCVR having the sequence set forth in SEQ ID NO: 48 (392A6); a HCVR having the sequence set forth in SEQ ID NO: 21 and a LCVR having the sequence set forth in SEQ ID NO: 52 (411C2); a HCVR having the sequence set forth in SEQ ID NO: 22 and a LCVR having the sequence set forth in SEQ ID NO: 51 (413D2); or a HCVR having the sequence set forth in SEQ ID NO: 25 and a LCVR having the sequence set forth in SEQ ID NO: 45 (413E1).

In some embodiments, the antibody comprises a HCVR having the sequence set forth in SEQ ID NO: 20 and a LCVR having the sequence set forth in SEQ ID NO: 53 (246A10); a HCVR having the sequence set forth in SEQ ID NO: 25 and a LCVR having the sequence set forth in SEQ ID NO: 45 (413E1); a HCVR having the sequence set forth in SEQ ID NO: 22 and a LCVR having the sequence set forth in SEQ ID NO: 51 (413D2); a HCVR having the sequence set forth in SEQ ID NO: 18 and a LCVR having the sequence set forth in SEQ ID NO: 47 (388D4); a HCVR having the sequence set forth in SEQ ID NO: 1 and a LCVR having the sequence set forth in SEQ ID NO: 28 (244C8); or a HCVR having the sequence set forth in SEQ ID NO: 9 and a LCVR having the sequence set forth in SEQ ID NO: 38 (392C5A).

In some embodiments, the isolated antibody that binds to PD-1 binds to a sequence in PD-1 selected from the group consisting of SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, and SEQ ID NO: 84.

As used herein, an "antibody that binds to PD-1, comprising" a HCVR or LCVR, means an antibody comprising the HCVR or LCVR, as opposed to a PD-1 protein comprising the HCVR or LCVR.

In some embodiments, the antibody binds specifically to PD-1. This means that the antibody binds to PD-1 protein in a sample, with negligible binding to other proteins present in the sample, under a given set of binding reaction conditions.

Examples of antibody fragments include, a Fab, Fab', $F(ab')_2$, Fv, scFv, dAb, and a diabody.

A "Fab fragment" comprises one light chain and the $C_H1$ and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_{H^2}$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

A "single-chain Fv antibody" (or "scFv antibody") refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) *The Pharmacology Of Monoclonal Antibodies*, vol. 113, Rosenburg and Moore eds. Springer-Verlag, New York, pp. 269-315. See also, PCT Publication No. WO 88/01649 and U.S. Pat. Nos. 4,946,778 and 5,260,203.

A "diabody" is a small antibody fragment with two antigen-binding sites. The fragments comprise a heavy chain variable region (VH) connected to a light chain variable region (VL) in the same polypeptide chain (VH-VL or VL-VH). By using a linker that is too short to allow pairing between the two domains on the same chain, the domains are forced to pair with the complementary domains of another chain and create two antigen-binding sites. Diabodies are described in, e.g., patent documents EP 404,097; WO 93/11161; and Holliger et al. (1993) *Proc. Natl. Acad. Sci. USA* 90: 6444-6448.

A "domain antibody fragment" is an immunologically functional immunoglobulin fragment containing only the variable region of a heavy chain or the variable region of a light chain. In some instances, two or more VH regions are covalently joined with a peptide linker to create a bivalent domain antibody fragment. The two VH regions of a bivalent domain antibody fragment may target the same or different antigens.

In some embodiments, the antibody is modified or engineered. Examples of modified or engineered antibodies include chimeric antibodies, multiparatopic antibodies (e.g., biparatopic antibodies), and multispecific antibodies (e.g., bispecific antibodies).

As used herein, "multiparatopic antibody" means an antibody that comprises at least two single domain antibodies, in which at least one single domain antibody is directed against a first antigenic determinant on an antigen and at least one other single domain antibody is directed against a second antigenic determinant on the same antigen. Thus, for example, a "biparatopic" antibody comprises at least one single domain antibody directed against a first antigenic determinant on an antigen and at least one further single domain antibody directed against a second antigenic determinant on the same antigen.

As used herein, "multispecific antibody" means an antibody that comprises at least two single domain antibodies, in which at least one single domain antibody is directed against a first antigen and at least one other single domain antibody is directed against a second antigen (different from the first antigen). Thus, for example, a "bispecific" antibody is one that comprises at least one single domain antibody directed against a first antigen and at least one further single domain antibody directed against a second antigen, e.g., different from the first antigen.

In some embodiments, the antibodies disclosed herein are monoclonal antibodies, e.g., murine monoclonal antibodies. Methods of producing monoclonal antibodies are known in the art. See, for example, Pluckthun (1994) *The Pharmacology Of Monoclonal Antibodies*, Vol. 113, Rosenburg and Moore eds. Springer-Verlag, New York, pp. 269-315.

In some embodiments, antibodies are modified to reduce immunogenicity. When the antibodies are to be administered to a human, the antibodies can be "humanized" to reduce or eliminate antigenicity in humans. Accordingly, in some embodiments, the antibody comprises a humanized or human framework region (FR).

In some embodiments, the isolated antibody that binds to PD-1 comprises a HCVR selected from the group consisting of SEQ ID NOs: 85-90.

In some embodiments, the isolated antibody that binds to PD-1 comprises a LCVR selected from the group consisting of SEQ ID NOs: 91-96.

In certain embodiments, the isolated antibody that binds to PD-1 comprises a HCVR selected from the group consisting of SEQ ID NOs: 85-90 and a LCVR selected from the group consisting of SEQ ID NOs: 91-96. Examples of pairings of HCVRs and LCVRs are provided throughout the present disclosure, but additional functional pairings are within the scope of the invention.

In some embodiments, the isolated antibody comprises a HCVR having the sequence set forth in SEQ ID NO: 90 and a LCVR having the sequence set forth in SEQ ID NO: 94; a HCVR having the sequence set forth in SEQ ID NO: 88 and a LCVR having the sequence set forth in SEQ ID NO: 96; a HCVR having the sequence set forth in SEQ ID NO: 90 and a LCVR having the sequence set forth in SEQ ID NO: 96; a HCVR having the sequence set forth in SEQ ID NO: 85 and a LCVR having the sequence set forth in SEQ ID NO: 91; a HCVR having the sequence set forth in SEQ ID NO: 85 and a LCVR having the sequence set forth in SEQ ID NO: 93; or a HCVR having the sequence set forth in SEQ ID NO: 86 and a LCVR having the sequence set forth in SEQ ID NO: 91.

Methods for reducing or eliminating the antigenicity of antibodies and antibody fragments are known in the art. In one approach, a nucleic acid encoding a PD-1 antibody disclosed herein is modified, for example, by replacing the mouse constant region with human heavy- and light-chain constant regions (e.g., U.S. Pat. No. 4,816,567; Morrison, et al., 1984, *Proc. Natl. Acad. Sci. USA,* 81:6851) to produce what is commonly referred to as a chimeric antibody.

A humanized antibody generally has one or more amino acid residues from a source that is non-human. The non-human amino acid residues are often referred to as "import" residues, and are typically taken from an "import" variable domain. Humanization can be performed generally following the method of Winter and co-workers (Jones et al., 1986, *Nature* 321:522-525; Riechmann et al., 1988, *Nature,* 332: 323-327; Verhoeyen et al., 1988, *Science* 239:1534-1536), by substituting non-human CDRs or CDR sequences for the corresponding sequences of a human antibody. In practice, humanized antibodies are typically human antibodies in which some CDR residues and possibly some FR residues are substituted by residues from analogous sites in non-human, for example, murine antibodies. Preferably, a humanized antibody has the same or substantially the same affinity for the antigen as the non-human, e.g., mouse antibody from which it was derived.

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of a PD-1 antibody are grafted into human FRs or consensus human FRs. To create consensus human FRs, FRs from several human heavy chain or light chain amino acid sequences are aligned to identify a consensus amino acid sequence. CDR grafting is described in, e.g., U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) *Nature* 321: 522-525; Riechmann et al. (1988) *Nature* 332: 323-327; Verhoeyen et al. (1988) *Science* 239: 1534-1536; and Winter (1998) *FEBS Lett* 430: 92-94.

The choice of human variable domains, both light and heavy, to be used in making the humanized antibodies is important to reduce antigenicity. According to the so-called "best-fit" method, the sequence of the variable domain of a rodent antibody is screened against the entire library of known human variable-domain sequences. The human sequence that is closest to that of the murine is then accepted as the FR for the humanized antibody (Sims et al., 1987, 1 *Immunol.* 151:2296; Chothia et al., 1987, *J Mol. Biol.* 196:901). Another method uses a particular framework derived from the consensus sequence of all human antibodies of a particular subgroup of light or heavy chains. The same framework may be used for several different humanized antibodies (Carter et al., 1992, *Proc. Natl. Acad. Sci. USA* 89:4285; Presta et al., 1993, *J. Immunol.* 151:2623).

It is important for humanized antibodies to retain affinity for the antigen and other desirable biological properties. To achieve this result, humanized antibodies can be designed analyzing parental sequences and various conceptual humanized products using three-dimensional models of the parental and humanized sequences. Three-dimensional immunoglobulin models are commonly available and are familiar to those skilled in the art. Computer programs that illustrate and display probable three-dimensional conformational structures of selected candidate immunoglobulin sequences are available. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Other methods to reduce immunogenicity include "reshaping," "hyperchimerization," and "veneering/resurfacing." See, e.g., Vaswami et al., 1998, *Ann. Allergy & Immunol.* 81:105; Roguska et al., 1996, *Prot. Engineer.* 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves use of a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Humanization of antibodies is routine protein engineering. Nearly all murine antibodies can be humanized by CDR grafting, resulting in the retention of antigen binding. See, e.g., Lo, Benny, K. C., editor, in Antibody Engineering: Methods and Protocols, Vol. 248, Humana Press, New Jersey, 2004.

In some embodiments, the antibodies are antagonists. As used herein, "antagonist" in reference to an anti-PD-1 antibody means an antibody that inhibits the PD-1 signaling pathway in a cell (e.g., an immune cell). An antagonist anti-PD-1 antibody might inhibit the PD-1 signaling pathway by blocking the PD-1/PD-L1 or PD-1/PD-L2 interaction, but does not necessarily do so.

In some embodiments, the antibodies are agonists. As used herein, "agonist" in reference to an anti-PD-1 antibody means an antibody that activates the PD-1 signaling pathway in a cell (e.g., an immune cell). An agonist antibody might influence the PD-1/PD-L1 and/or PD-1/PD-L2 interaction, but does not necessarily do so.

An antibody that binds to PD-1 and competitively inhibits the binding of an antibody that contains one or more sequences disclosed herein is within the scope of the invention. In certain embodiments, the antibody competitively inhibits the binding of the antibody that comprises a HCVR having the sequence set forth in SEQ ID NO: 20 and a LCVR having the sequence set forth in SEQ ID NO: 53 (246A10); a HCVR having the sequence set forth in SEQ ID NO: 25 and a LCVR having the sequence set forth in SEQ ID NO: 45 (413E1); a HCVR having the sequence set forth in SEQ ID NO: 22 and a LCVR having the sequence set forth in SEQ ID NO: 51 (413D2); a HCVR having the sequence set forth in SEQ ID NO: 18 and a LCVR having the sequence set forth in SEQ ID NO: 47 (388D4); a HCVR having the sequence set forth in SEQ ID NO: 1 and a LCVR having the sequence set forth in SEQ ID NO: 28 (244C8). In some embodiments, the antibody also binds to a sequence in PD-1 selected from the group consisting of SEQ ID NOs: 54-84.

Methods for determining whether two or more antibodies compete for binding to the same target are known in the art. For example, a competitive binding, or competition, assay can be used to determine whether one antibody blocks the binding of another antibody to the target. Typically, a competition assay involves the use of purified target antigen (e.g., PD-1) bound to a solid substrate or expressed on cells, an unlabeled test binding molecule (e.g., a test anti-PD-1 antibody), and a labeled reference binding molecule (e.g., an antibody disclosed herein). Competitive inhibition is measured by determining the amount of label bound to the solid substrate or cells in the presence of the test molecule. Usually (but not necessarily) the molecule is present in excess of at least two-fold. A test antibody competes with the reference antibody or ligand (e.g., PD-L1 or PD-L2) for specific binding to the antigen if an excess of one antibody inhibits binding of the other antibody or ligand by at least 50%, as measured in a competition assay.

In an exemplary competition assay, a reference anti-PD-1 antibody (e.g., an antibody disclosed herein) is biotinylated using commercially available reagents. The biotinylated reference antibody is mixed with serial dilutions of the test antibody or unlabeled reference antibody (self-competition control) resulting in a mixture of various molar ratios of test antibody (or unlabeled reference antibody) to labeled reference antibody. The antibody mixture is added to a PD-1 coated-ELISA plate. The plate is then washed, and horseradish peroxidase (HRP)-strepavidin is added to the plate as the detection reagent. The amount of labeled reference antibody bound to the target antigen is detected following addition of a chromogenic substrate (e.g., TMB (3,3',5,5'-tetramethylbenzidine) or ABTS (2,2"-azino-di-(3-ethylbenzthiazoline-6-sulfonate)), which are known in the art. Optical density readings (OD units) are measured using a spectrophotometer. OD units corresponding to zero percent inhibition are determined from wells without any competing antibody. OD units corresponding to 100% inhibition, i.e., the assay background, are determined from wells without any labeled reference antibody or test antibody. Percent inhibition of labeled reference antibody to PD-1 by the test antibody (or the unlabeled reference antibody) at each concentration is calculated as follows: % inhibition=(1−(OD units−100% inhibition)/(0% inhibition−100% inhibition))*100. Persons skilled in the art will appreciate that the competition assay can be performed using various detection systems known in the art.

Antibodies identified by competition assay (e.g., competing antibodies) include antibodies binding to the same epitope, or similar (e.g., overlapping) epitopes, as the reference antibody. In addition, the competition assay can identify antibodies binding to an adjacent epitope sufficiently proximal to the epitope bound by the reference antibody for steric hindrance to occur.

Two antibodies bind to the same epitope if essentially all amino acid mutations in the antigen that reduce or eliminate binding of one antibody to the antigen reduce or eliminate binding of the other. Two antibodies bind to overlapping epitopes if only a subset of the amino acid mutations that reduce or eliminate binding of one antibody to the antigen reduce or eliminate binding of the other.

A competition assay may be conducted in both directions to ensure that the presence of the label does not interfere with or otherwise inhibit binding. For example, in the first direction, the reference antibody is labeled and the test antibody is unlabeled, and in the second direction, the test antibody is labeled and the reference antibody is unlabeled.

In certain embodiments, the present invention provides a method for increasing T cell effector function, comprising contacting a T cell with a combination of: (a) an effective amount of an anti-PD-1 antibody that competitively inhibits binding of PD-L1 or PD-L2 to PD-1 expressed on the surface of the T cell; and (b) an effective amount of an anti-PD-1 antibody that does not competitively inhibit binding of PD-L1 or PD-L2 to PD-1 expressed on the surface of the T cell. In some embodiments, increasing T cell effector function includes, e.g., increased secretion of effector cytokines, as demonstrated herein.

In some embodiments, the T cell is contacted with the combination of antibodies in vivo. For example, in certain embodiments, the T cell is contacted with the combination in a human patient in need of increased T cell effector function.

In some embodiments, the present invention also provides a method for increasing T cell effector function, comprising contacting a T cell with an anti-PD-1 antibody that does not competitively inhibit binding of PD-L1 or PD-L2 to PD-1 expressed on the surface of the T cell. In certain embodiments, the T cell is contacted with an antibody that comprises a heavy chain variable region having complementarity determining regions (CDRs) selected from the group consisting of CDRs 1-3 of SEQ ID NO:85, CDRs 1-3 of SEQ ID NO:86, and CDRs 1-3 of SEQ ID NO:87; and a light chain variable region having CDRs selected from the group consisting of CDRs 1-3 of SEQ ID NO:91, CDRs 1-3 of SEQ ID NO:92, and CDRs 1-3 of SEQ ID NO:93. In some embodiments, the T cell is contacted with an antibody that comprises a heavy chain variable region selected from the group consisting of SEQ ID NOS: 85, 86 and 87 and a light chain variable region selected from the group consisting of SEQ ID NOS: 91, 92 and 93. In certain embodiments, the T cell is contacted with an antibody that is selected from the group consisting of antibody 244C8-1, antibody 244C8-2 and antibody 244C8-3.

In some embodiments, the present invention provides a method for increasing lymphocyte secretion of a cytokine selected from the group consisting of IL-6, IL-12, IL-18, TNF-α, IL-1β and GM-CSF in a human patient in need of increased T cell effector function, comprising administering to the patient a therapeutically effective amount of an anti-PD-1 antibody that does not competitively inhibit binding of PD-L1 or PD-L2 to PD-1 expressed on the surface of a T cell. In certain embodiments, the patient is administered an antibody that comprises a heavy chain variable region having complementarity determining regions (CDRs) selected from the group consisting of CDRs 1-3 of SEQ ID NO:85, CDRs 1-3 of SEQ ID NO:86, and CDRs 1-3 of SEQ ID NO:87; and a light chain variable region having CDRs selected from the group consisting of CDRs 1-3 of SEQ ID NO:91, CDRs 1-3 of SEQ ID NO:92, and CDRs 1-3 of SEQ ID NO:93. In some embodiments, the patient is administered an antibody that comprises a heavy chain variable region selected from the group consisting of SEQ ID NOS: 85, 86 and 87 and a light chain variable region selected from the group consisting of SEQ ID NOS: 91, 92 and 93. In certain embodiments, the patient is administered an antibody that is selected from the group consisting of antibody 244C8-1, antibody 244C8-2 and antibody 244C8-3.

In some embodiments, the present invention also provides a method of treating cancer in a mammal, comprising contacting a T cell in a mammal in need thereof with a combination of: (a) an effective amount of an anti-PD-1 antibody that competitively inhibits binding of PD-L1 or PD-L2 to PD-1 expressed on the surface of the T cell; and (b) an effective amount of an anti-PD-1 antibody that does not competitively inhibit binding of PD-L1 or PD-L2 to PD-1 expressed on the surface of the T cell.

The presently disclosed method of treating cancer with a combination of anti-PD-1 antibodies can be used to treat various cancers. In some embodiments, the cancer is selected from the group consisting of: melanoma, renal cancer, prostate cancer, pancreatic adenocarcinoma, breast cancer, colon cancer, lung cancer, esophageal cancer, squamous cell carcinoma of the head and neck, liver cancer, ovarian cancer, cervical cancer, thyroid cancer, glioblastoma, glioma, leukemia, and lymphoma.

In some embodiments, the anti-PD-1 antibody that competitively inhibits binding of PD-L1 or PD-L2 to PD-1 expressed on the surface of a T cell is selected from the group consisting of: 388D4, nivolumab, pembrolizumab, EH12.2H7 and J105. In some embodiments, the anti-PD-1 antibody that competitively inhibits binding of PD-L1 or PD-L2 to PD-1 expressed on the surface of a T cell is 388D4.

In some embodiments, the anti-PD-1 antibody that does not competitively inhibit binding of PD-L1 or PD-L2 to PD-1 expressed on the surface of a T cell is 244C8. In some embodiments, the anti-PD-1 antibody that does not competitively inhibit binding of PD-L1 or PD-L2 to PD-1 expressed on the surface of the T cell binds to one or more of the following amino acid sequences: SEQ ID NO: 74, SEQ ID NO: 77, SEQ ID NO: 80, SEQ ID NO: 83 and SEQ ID NO: 84. In some embodiments, the anti-PD-1 antibody binds to all of the following amino acid sequences: SEQ ID NO: 74, SEQ ID NO: 77, SEQ ID NO: 80, SEQ ID NO: 83 and SEQ ID NO: 84. In some embodiments, the anti-PD-1 antibody that does not competitively inhibit binding of PD-L1 or PD-L2 to PD-1 expressed on the surface of the T cell binds to a PD-1 epitope bound by 244C8. In some embodiments, the anti-PD-1 antibody that does not competitively inhibit binding of PD-L1 or PD-L2 to PD-1 expressed on the surface of the T cell competes with 244C8 for binding to PD-1.

The presently disclosed method of treating cancer with an anti-PD-1 antibody that competitively inhibits binding of PD-L1 or PD-L2 to PD-1 expressed on the surface of T cells, and an effective amount of an anti-PD-1 antibody that does not competitively inhibit binding of PD-L1 or PD-L2 to PD-1 expressed on the surface of the T cells, increases T cell effector function to a greater extent than an equivalent amount of either anti-PD-1 antibody alone. In some embodiments, the combination yields an additive effect on T cell effector function. In some embodiments, the combination yields a synergistic effect on T cell effector function.

The present invention provides isolated nucleic acids comprising a nucleotide sequence encoding a HCVR and/or a LCVR disclosed herein, or a fragment thereof. A nucleic acid according to the present invention may comprise DNA or RNA, and may be wholly or partially synthetic. For example, DNA molecules encoding an HCVR and/or LCVR disclosed herein can be chemically synthesized. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, nucleotide sequences can be cloned out of hybridomas, for example, by conventional hybridization techniques or polymerase chain reaction (PCR) techniques, using synthetic nucleic acid probes or primers whose sequences are based on sequence information provided herein, or known sequence information regarding genes encoding the heavy and light chains of murine antibodies in hybridoma cells.

Techniques and protocols for engineering and production of nucleic acids are known in the art. See, e.g., *Current Protocols in Molecular Biology*, Second Edition, Ausubel et al. eds., John Wiley & Sons, 1992.

A nucleotide sequence encoding an antibody of the invention can be operably linked to a promoter to effect expression of the antibody in a host cell. The sequence may include at its 5' end a leader sequence to facilitate expression in a host cell and/or secretion of the antibody from a host cell. Suitable leader sequences are known in the art and can be selected by the skilled person, taking account of the host cell.

In some embodiments, the nucleic acid is incorporated into a vector. Suitable vectors containing appropriate regulatory sequences, including promoter sequences, terminator sequences, polyadenylation sequences, enhancer sequences, marker genes and other sequences as appropriate, can be obtained commercially or constructed by persons of skill in the art. For further details see, e.g., *Molecular Cloning: a Laboratory Manual,* 2nd edition, Sambrook et al., 1989, Cold Spring Harbor Laboratory Press. Examples of vectors include plasmids, phages, phagemids, and cosmids, as well as transcription and expression cassettes.

Nucleic acids encoding a HCVR and/or a LCVR disclosed herein can be incorporated (ligated) into expression vectors, which can be introduced into host cells through conventional transfection or transformation techniques. Accordingly, a host cell can be transformed with an expression vector comprising a nucleotide sequence encoding a HCVR and/or a LCVR, or a fragment thereof. Examples of host cells include *E. coli* cells, Chinese hamster ovary (CHO) cells, human embryonic kidney 293 (HEK 293) cells, HeLa cells, baby hamster kidney (BHK) cells, monkey kidney cells (COS), and human hepatocellular carcinoma cells (e.g., Hep G2).

Methods of producing an HCVR and/or LCVR, or a fragment thereof, disclosed herein are within the scope of the invention. In some embodiments, the method comprises: (a) growing a host cell containing an expression vector encoding the HCVR and/or LCVR under conditions so that the host cell expresses the antibody comprising the HCVR and/or LCVR, or a fragment thereof; and (b) isolating the antibody comprising the HCVR and/or LCVR, or a fragment thereof.

Suitable conditions for antibody expression and isolation or purification depend on the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO (Chinese hamster ovary) cells, it is first inserted into an expression vector containing a suitable eukaryotic promoter, a secretion signal, a poly A sequence, and a stop codon. Optionally, the vector or gene construct contains enhancers and introns. This expression vector optionally contains sequences encoding all or part of a constant region, enabling an entire, or a part of, a heavy or light chain to be expressed. The gene construct can be introduced into eukaryotic host cells using conventional techniques. The host cells express VL or VH fragments, VL-VH heterodimers, VH-VL or VL-VH single chain polypeptides, complete heavy or light immunoglobulin chains, or portions thereof, each of which may be attached to a moiety having another function (e.g., cytotoxicity).

In some embodiments, a host cell is transfected with a single vector expressing a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In some embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced, for example, by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as Protein A, Protein G, glutathione-S-transferase (GST), or histidine tags.

The antibodies of the present invention can be produced by growing (culturing) a host cell transfected with, for example: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

In some embodiments, anti-PD-1 antibodies are linked to a different functional molecule or moiety, e.g., a peptide, protein, toxin, radioisotope, or cytostatic agent, for various purposes such as in vivo diagnostic imaging or a diagnostic assay. The antibodies can be linked by chemical cross-linking or by recombinant methods. The antibodies also can be linked to any of various nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337. The antibodies can be chemically modified by covalent conjugation to a polymer, for example, to increase their circulating half-life. Examples of polymers and methods to attach them are described in U.S. Pat. Nos. 4,766,106; 4,179,337; 4,495,285; and 4,609,546.

Pharmaceutical Formulations

In some embodiments, the antibodies are formulated into pharmaceutical compositions suitable for administration to a mammal, e.g., a human patient. The compositions typically comprise one or more antibodies of the present invention and a pharmaceutically acceptable excipient. The term "pharmaceutically acceptable excipient" includes suitable solvents, dispersion media, coatings, antibacterial agents and antifungal agents, isotonic agents, and absorption delaying agents, and the like, that are compatible with pharmaceutical administration. The use of such media and agents for pharmaceutically active substances is known in the art. The compositions also can contain other active compounds providing supplemental, additional, or enhanced therapeutic functions. The pharmaceutical compositions also can be included in a container, pack, or dispenser together with instructions for administration.

A pharmaceutical composition of the invention is formulated to be compatible with its intended route of administration. Methods to accomplish the administration are known in the art. The administration may be, for example, intravenous, intraperitoneal, intramuscular, intracavity, subcutaneous, intradermal, topical, inhalation, transmucosal, rectal or transdermal.

Solutions or suspensions used for intradermal or subcutaneous application typically include one or more of the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose. The pH can be adjusted with acids or bases, as necessary. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. Sterilization can be accomplished, for example, by filtration through sterile filtration membranes. For intravenous administration, suitable carriers include, for example, physiological saline, bacteriostatic water, Cremophor EL (BASF, Parsippany, N.J.) or phosphate buffered saline (PBS). Preferably, the pharmaceutical composition is stable under the conditions of manufacture and storage and is preserved against contamination by microorganisms such as bacteria and fungi. Avoidance of microorganisms can be achieved by inclusion of antibacterial and/or antifungal agents. Examples include: parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. The carrier can be a solvent or dispersion medium containing, for example, water, ethanol, polyol such as glycerol, propylene glycol, liquid polyetheylene glycol, and the like, and suitable mixtures thereof. The proper fluidity can be maintained, for example, by the use of a coating such as lecithin, by the maintenance of the required particle size in the case of dispersion and/or by the use of surfactants. Prolonged absorption of the injectable compositions can be achieved by including in the composition an agent that delays absorption, e.g., aluminum monostearate or gelatin.

Oral compositions generally include an inert diluent or an edible carrier. They can be enclosed in gelatin capsules or compressed into tablets. For oral administration, the antibodies can be combined with excipients and used in the form of tablets, troches, or capsules.

For transmucosal or transdermal administration, penetrants appropriate to the barrier to be permeated can be used in the formulation. Such penetrants are known in the art, and include, for example, detergents, bile salts, and fusidic acid derivatives. Transmucosal administration may be accomplished, for example, through the use of lozenges, nasal sprays, inhalers, or suppositories. For example, in case of antibodies that comprise the Fc portion, compositions may be capable of transmission across mucous membranes in intestine, mouth, or lungs (e.g., via the FcRn receptor-mediated pathway as described in U.S. Pat. No. 6,030,613). For transdermal administration, the active compounds may be formulated into ointments, salves, gels, or creams as generally known in the art. For administration by inhalation, the antibodies may be delivered in the form of an aerosol spray from pressured container or dispenser, which contains a suitable propellant, e.g., a gas such as carbon dioxide, or a nebulizer.

In some embodiments, the presently disclosed antibodies are formulated with carriers that protect the antibody against rapid elimination from the body, such as a controlled release formulation, including implants and microencapsulated delivery systems. Biodegradable, biocompatible polymers can be used. Exemplary polymers include ethylene vinyl acetate, polyanhydrides, polyglycolic acid, collagen, polyorthoesters, and polylactic acid. Methods for preparation of such formulations will be apparent to those skilled in the art. Liposomal suspensions containing the presently disclosed antibodies can also be used as pharmaceutically acceptable carriers. These can be prepared according to methods known in the art. See, e.g., U.S. Pat. No. 4,522,811.

In some embodiments, pharmaceutical compositions contain, in addition to an antibody of the invention, a cytotoxic agent, cytostatic agent, anti-angiogenic agent, a tumor targeted agent, an immune stimulating agent or immune modulating agent, or an antibody conjugated to a cytotoxic, cytostatic, or otherwise toxic agent. The pharmaceutical composition optionally can be employed with other therapeutic modalities such as surgery, chemotherapy, and radiation.

Toxicity and therapeutic efficacy of the composition of the invention can be determined by conventional pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

A therapeutically effective dose of a therapeutic antibody can be estimated initially, e.g., from cell culture assays. Examples of suitable bioassays include DNA replication assays, cytokine release assays, transcription-based assays, PD-1/PD-L1 binding assays, creatine kinase assays, assays based on the differentiation of pre-adipocytes, assays based on glucose uptake in adipocytes, immunological assays other assays as, for example, described in the Examples. The data obtained from the cell culture assays and animal studies can be used in formulating a range of dosage for use in humans. A dose may be formulated in animal models to achieve a circulating plasma concentration range that includes the $IC_{50}$ (i.e., the concentration of the antibody that achieves a half-maximal inhibition of symptoms). Circulating levels in plasma may be measured, for example, by high performance liquid chromatography. The effects of any particular dosage can be monitored by a suitable bioassay. The dosage lies preferably within a range of circulating concentrations with little or no toxicity. The dosage may vary depending upon the dosage form employed and the route of administration.

Generally, a therapeutically effective amount of an antibody or a composition described herein is in the range of 0.1 mg/kg to 100 mg/kg, preferably 0.1 mg/kg to 50 mg/kg. The amount administered will depend on variables such as the type and extent of disease or indication to be treated, the overall health of the patient, the in vivo potency of the antibody, the pharmaceutical formulation, the serum half-life of the antibody, and the route of administration.

Administration frequency can vary, depending on factors such as route of administration, dosage amount, serum half-life of the antibody or fusion protein, and the disease being treated.

Therapeutic Uses

The invention provides methods of treating PD-1-mediated diseases or disorders in a mammal, e.g., a human patient, comprising administering an effective amount of an antibody of the present invention to a mammal in need thereof. In some embodiments, the method is a method of treating cancer. In some embodiments, the method is a method of treating inflammation. In some embodiments, the method is a method of treating an autoimmune disease, e.g., Crohn's disease.

As used herein, "treat", "treating" or "treatment" means inhibiting or relieving a disease or disorder. For example, treatment can include a postponement of development of the symptoms associated with a disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

As used herein, the term "effective amount" means an amount of an anti-PD-1 antibody, that when administered alone or in combination with an additional therapeutic agent to a cell, tissue, or subject, is effective to achieve the desired therapeutic or prophylactic effect under the conditions of administration. For example, an effective amount is one that would be sufficient to enhance or diminish the immune response to bring about effectiveness of a therapy. The effectiveness of a therapy (e.g., activation of a suppressed or deficient immune response, increased cytolytic activity of T cells, increased T cell effector function, alteration of PD-1 activity associated with the negative regulation of T-cell mediated immune response, or reduction in tumor growth) can be determined by suitable methods known in the art.

When used to treat cancer, antibodies of the invention can be used alone or in combination with another therapeutic agent. Examples of other therapeutic agents include other checkpoint inhibitors, immunogenic agents, attenuated cancerous cells, tumor antigens (e.g., recombinant proteins, peptides, and carbohydrate molecules), antigen presenting cells such as dendritic cells pulsed with tumor-derived antigen or nucleic acids, immune stimulating cytokines (e.g., IL-2, IFNa2, GM-CSF), and cells transfected with a gene encoding an immune stimulating cytokine (e.g., GM-CSF); chemotherapy, radiotherapy, and surgery.

In some embodiments, an antibody of the invention is administered to a cancer patient in combination with another checkpoint inhibitor. The other checkpoint inhibitor can be targeted against PD-1 or against a different checkpoint molecule, e.g., TIM3, CEACAM1, TIGIT, LAG3 or VISTA. The other checkpoint inhibitor can be a small molecule or a monoclonal antibody. When the other checkpoint inhibitor is a second PD-1 inhibitor, preferably, the mechanism of action of the second PD-1 inhibitor differs from the mechanism of action of the first PD-1 inhibitor. For example, the two PD-1 inhibitors can be two anti-PD-1 monoclonal antibodies that bind to different epitopes on the PD-1 molecule.

When used to treat cancer, antibodies of the invention can be used alone or in combination with other checkpoint inhibitors, anti-neoplastic agents or immunogenic agents. Examples include attenuated cancerous cells, tumor antigens (including, e.g., recombinant proteins, peptides, and carbohydrate molecules), antigen presenting cells such as dendritic cells pulsed with tumor-derived antigen or nucleic acids, immune stimulating cytokines (e.g., IL-2, IFNa2, GM-CSF), and cells transfected with genes encoding immune stimulating cytokines (e.g., GM-CSF; cancer treatments such as chemotherapy, radiotherapy, and surgery).

In treating certain diseases or disorders, it is desirable to diminish or suppress a patient's immune response, at least in certain tissues of the body. Such diseases and disorders include allergies and various autoimmune diseases. Examples of autoimmune diseases include rheumatoid arthritis, type I diabetes mellitus, multiple sclerosis, inflammatory bowel disease, Crohn's disease, and systemic lupus erythematosis, Hashimoto's thyroiditis, ankylosing spondylitis, and graft-versus-host disease (GVHD). It is also desirable to suppress a patient's immune response to avoid transplant rejection following tissue, skin or organ transplant.

In some embodiments, anti-PD-1 antibodies of the invention are administered with one or more additional therapeutic agents, e.g., a cytotoxic agent, a radiotoxic agent, or an immunosuppressive agent. The antibody can be linked to the agent (as an immunocomplex) or administered separately. In some embodiments, the additional therapeutic agent is an immunomodulatory agent or an anti-cancer agent (e.g., a chemotherapeutic agent). In separate administration, the antibody can be administered before, after or concurrently with the agent or can be co-administered with other known therapies. Combination therapies are known in the art. See, e.g., Hardman, et al. (eds.) (2001) *Goodman and Gilman's The Pharmacological Basis of Therapeutics,* 10th ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Philadelphia, PA.

In some embodiments, an antibody disclosed herein is used as a targeting agent for delivery of a payload, e.g., a toxin, to a cell expressing PD-1. The method includes administering an anti-PD-1 antibody conjugated to a payload moiety. Suitable conjugation methods are known in the art.

Non-Therapeutic Uses

In some embodiments, antibodies of the invention are used for non-therapeutic purposes, such as diagnostic tests and assays. For example, the invention provides a method of diagnosing a PD-1-mediated adaptive immune resistance in a patient who has cancer. The method comprises contacting a tumor microenvironment in the patient with an antibody disclosed herein that has been labeled with a detectable moiety; and detecting expression of PD-1 on immune cells, e.g., CD8+ T cells; B cells; and macrophages, within the tumor microenvironment.

Adaptive immune resistance includes suppression of a host immune response as a result of activation of a PD-1 signaling pathway in immune cells of the host. For example, cancer tissue suppresses a host immune response by upregulation of PD-L1 and its binding to PD-1 on immune cells on T cells (such as CD8+ T cells); B cells; and macrophages.

A diagnostic method utilizing an antibody of the invention to detect PD-1 expression also can comprise an agent for detecting expression of PD-L1 on immune cells within the tumor microenvironment. Such a diagnostic method can be performed in vivo, or on a biopsy sample from a patient, wherein the tumor microenvironment is present in a tumor biopsy.

Modifications of antibodies for diagnostic purposes are well known in the art. For example, antibodies may be modified with a ligand group such as biotin, or a detectable marker group such as a fluorescent group, a radioisotope, or an enzyme. Antibodies of the invention can be labeled using conventional techniques. Suitable detectable labels include: fluorophores, chromophores, radioactive atoms, electron-dense reagents, enzymes, and ligands having specific binding partners. Enzymes typically are detected by their reaction products. For example, horseradish peroxidase can be detected through conversion of tetramethylbenzidine (TMB) to a blue pigment, quantifiable with a spectrophotometer. For detection, suitable binding partners include biotin and avidin or streptavidin, IgG and protein A, and the numerous receptor-ligand couples known in the art. Other permutations and possibilities will be readily apparent to those of ordinary skill in the art.

Antibodies of the invention also can be used to detect the presence of PD-1 in biological samples. The amount of PD-1 detected can be correlated with the expression level of PD-1, which, in turn, is correlated with the activation status of immune cells, e.g., activated T cells, B cells, and monocytes, in the subject.

Detection methods that employ antibodies are known in the art, and include ELISA, radioimmunoassay, immunoblot, Western blot, immunofluorescence, and immunoprecipitation techniques. Antibodies of the invention can be provided in a diagnostic kit that incorporates one or more of these techniques to detect PD-1. Such a kit may contain other components, packaging, instructions, or material to aid in the detection of PD-1 protein.

EXAMPLES

The following Examples are merely illustrative, and are not intended to limit the scope or content of the invention in any way.

Example 1. Identification of PD-1 Antibodies

A. Immunization of Mice with PD-1

Balb/C, C57BL/6 or NZW/B female mice aged 4-8 weeks were immunized in a standard prime/boost regimen employing standard adjuvant mixtures. A soluble extracellular domain of human PD-1 (AA1-167) expressed with a C-terminal polyhistidine sequence (SinoBiological #10377-H08H) was used for immunizations. Cohorts of mice were primed with 50 μg of recombinant PD-1 and (1) complete Freund's adjuvant (Sigma-Aldrich #263810) or (2) alhydrogel (Invivogen). Two to three weeks later, animals in each group were boosted with 50 μg of soluble PD-1 with (1) incomplete Freund's adjuvant (Sigma-Aldrich #263910) or (2) alhydrogel. Serum titres were collected after each antigen boost and assayed by ELISA for reactivity and antibody isotype class switching. The same protein used for immunizations was immobilized onto 96 well assay plates (Nunc MAXISORP) at a concentration of 1 μg/mL. Serial dilutions of the sera from immunized animals were then tested for binding to PD-1.

B. Screening of Antibodies for Binding to Human PD-1

Cells, fresh or thawed from cryopreserved samples, from bone marrow, lymph nodes or the spleen were carried in standard tissue culture medium (LifeTech RPMI with 10% low IgG). Cells were interrogated for antigen-specific B cells, unstimulated or stimulated, using LPS (Invivogen) at a concentration of 20 ng/mL. Cells, unstimulated or stimulated, were then loaded at a stochastic cellular density to favor single cell per well loading onto microwell arrays (MWAs) as described in U.S. Pat. Nos. 7,776,553 and 8,772,049.

A functionalized capture surface, coated with two mixtures of polyclonal anti-mouse IgG antibodies (Jackson Immunoresearch #715-005-150, #115-005-146), was then used to hermetically seal the ordered microwell array. After two hours, the capture surface(s) was removed from the microdevices and processed as described previously (Ogunnyi et al. *Nature Protocols,* 2009). The microarray capture surface, representing a mirror image of the cells in the microwell array, contained the secreted output of the B cells. The antibodies secreted by the B cells in nanowells and captured were then assayed for reactivity against human PD-1, or an unrelated antigen, and also assayed for IgG versus IgM reactivity (JacksonImmunoresearch #115-005-044, #115-005-164).

After the protein microarrays were scanned, putative antibody clones with the desired specificity and antibody isotype class were bioinformatically identified by standard data quality metrics. According to methods previously described (Ogunnyi et al., *Vaccine* 2014), microarray images were analyzed using Molecular Devices GenePix software. Microarray features were analyzed for false positivity, co-variance, and signal-to-noise ratios. Features with the correct attributes, e.g., specific for PD-1 and IgG, were then nominated for cellular retrieval. This automated pick-list was then generated from 4 to 12 microdevices, and cells that had secreted antibodies with desired characteristics were isolated from the microdevices and placed into standard SBS microtitre assay plates for further processing.

C. Isolation of Antibodies that Bind PD-1

Single antibody-producing cells identified from screening were used for single cell molecular biology in order to isolate the genetic sequences encoding antibody heavy and light chains (Tiller et al., *J. Immunol. Methods* 350:183-93 (2009)). The genes encoding the specific antibodies that recognize human PD-1 were retrieved using single cell RT-PCR. Retrieved cells were placed into reverse transcription buffer, and the mRNA from each individual cell was reverse transcribed (LifeTech SuperScript III) into cDNA. After generating these amplicons by standard nested polymerase chain reaction(s) (PCR), these amplicons were subjected to direct sequencing. After analysis by Phred software using a Phred 0.05 cut-off value, sequences were sub-cloned into PCR 2.1 (LifeTech) or other standard vector backbones for further propagation. Phred is software that reads DNA sequencing trace files, calls bases, and assigns a quality value to each called base. See, e.g., Ewing and Green, *Genome Research* 8:186-94 (1998).

These DNA sequences were then bioinformatically filtered for sequence quality and organized into a sequence database for cladistics analysis (distance or parsimony), in order to identify how many unique antibody clades were isolated that recognize PD-1. These analyses identified approximately 20 unique clades (groups) of sequences that recognize human PD-1.

D. Antibody Construction

Complete antibody variable regions comprising a pair of heavy and light chain variable regions (Tables 1 and 2) were reformatted into plasmids with the proper elements for transient ectopic expression in mammalian cell lines, e.g., HEK293 or CHO, using standard molecular biology techniques. For example, the variable heavy (VH) and variable light (VL) cDNA sequences were sub-cloned into the vector backbone pFUSE-CHIg-mG1 (InVivoGen), which contains an IL2 signal sequence, as well as an in-frame murine Fc-domain. A sequence verified consensus sequence for each antibody VH and VL gene was engineered, using PCR primers, with restriction sites. The expression vector of choice and the PCR amplicons were then digested with restriction enzymes and then ligated together for transformation of *E. Coli*. Resulting expression clones were sequence verified.

Figure 2:
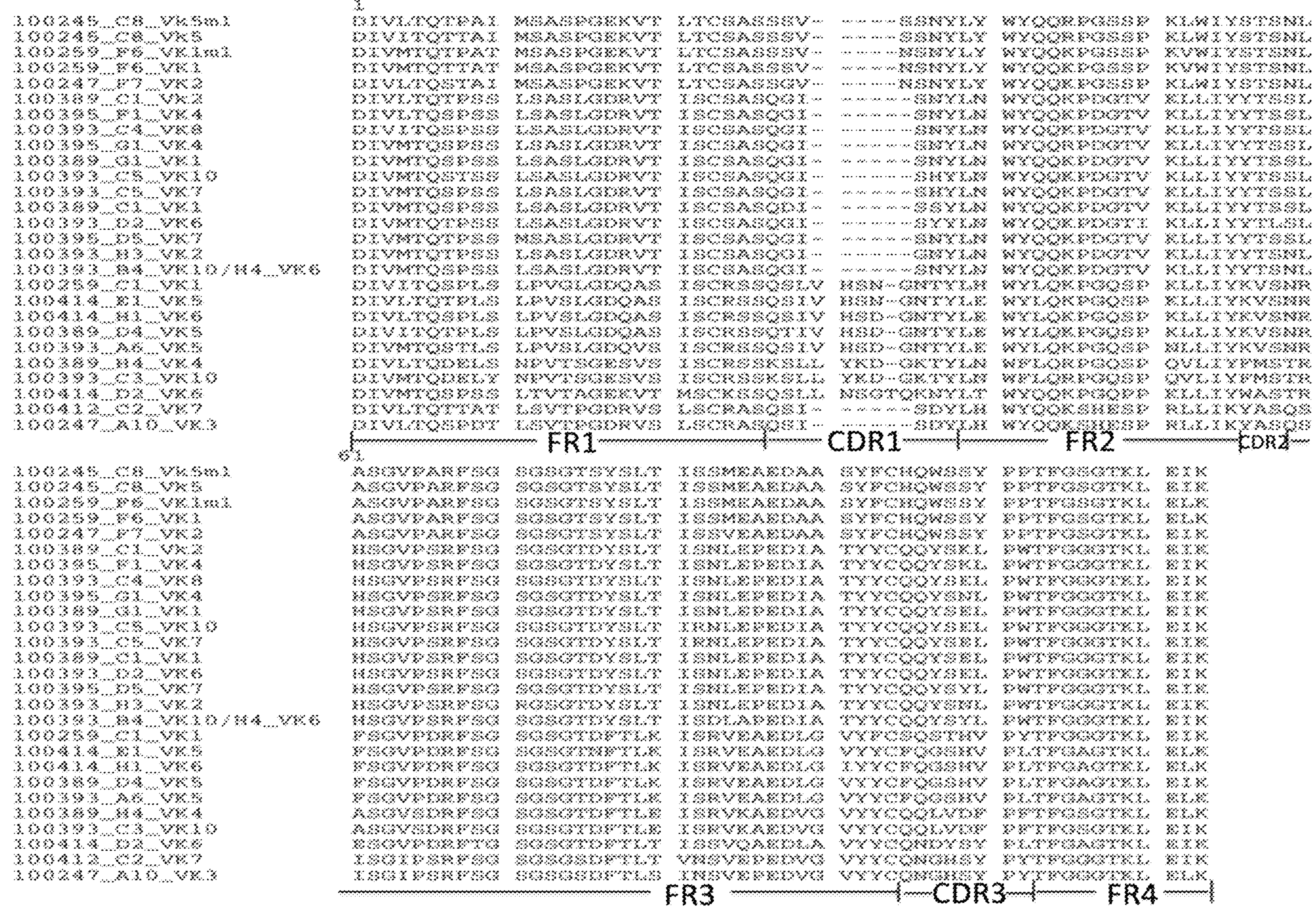
FIG. 2 is an alignment of the sequences of 27 light chain variable regions (LCVR) from antibodies that bind to human PD-1. The lower segment of the sequences is a continuation of the upper segment. Framework regions FR1 through FR4 are indicated. Complementarity determining regions CDR1 through CDR3 are also shown.

The sequences of the individual heavy chain and light chain variable regions are shown in FIG. 1 (HCVR) and FIG. 2 (LCVR). The complementarity determining regions (CDRs) and framework regions (FRs) are indicated. Tables 1 and 2 list each HCVR or LCVR by clone name and corresponding sequence identifier. The corresponding sequences are shown in FIGS. 1 and 2.

TABLE 1

Heavy Chain Variable Region Sequence Designations and Identifiers

| Heavy Chain Variable Region | SEQ ID NO: |
|---|---|
| 100244_C8VH3 | 1 |
| 100258_F6VH4 | 2 |
| 100246_F7VH3 | 3 |
| 100244_C7VH10 | 4 |
| 100258_C1VH4 | 5 |
| 100392_C4VH5 | 6 |
| 100394_D5VH9 | 7 |
| 100394_G1VH1 | 8 |
| 100392_C5VH6 | 9 |
| 100392_H3VH6 | 10 |
| 100394_F1VH8 | 11 |
| 100388_C1VH2 | 12 |
| 100388_C1VH6 | 13 |
| 100388_G1VH5 | 14 |
| 100392_B4VH10 | 15 |
| 100392_H4VH9 | 16 |
| 100392_D2VH7 | 17 |
| 100388_D4VH3 | 18 |
| 100392_A6VH8 | 19 |
| 100246_A10VH1 | 20 |
| 100411_C2VH3 | 21 |
| 100413_D2VH9 | 22 |
| 100388_H4VH1 | 23 |
| 100392_C3VH7 | 24 |
| 100413_E1VH9 | 25 |
| 100413_H1VH3 | 26 |

TABLE 2

| Light Chain Variable Region Sequence Designations and Identifiers | |
|---|---|
| Light Chain Variable Region | SEQ ID NO: |
| 100245_C8VK5ml | 27 |
| 100245_C8VK5 | 28 |
| 100259_F6VK1m1 | 29 |
| 100259_F6VK1 | 30 |
| 100247_F7VK2 | 31 |
| 100389_C1VK2 | 32 |
| 100395_F1VK4 | 33 |
| 100393_C4VK8 | 34 |
| 100395_G1VK4 | 35 |
| 100389_G1VK1 | 36 |
| 100393_C5VK10 | 37 |
| 100393_C5VK7 | 38 |
| 100389_C1VK1 | 39 |
| 100393_D2VK6 | 40 |
| 100395_D5VK7 | 41 |
| 100393_H3VK2 | 42 |
| 100393_B4VK10/H4VK6 | 43 |
| 100259_C1VK1 | 44 |
| 100414_E1VK5 | 45 |
| 100414_H1VK6 | 46 |
| 100389_D4VK5 | 47 |
| 100393_A6VK5 | 48 |
| 100389_H4VK4 | 49 |
| 100393_C3VK10 | 50 |
| 100414_D2VK6 | 51 |
| 100412_C2VK7 | 52 |
| 100247_A10VK3 | 53 |

Example 2. Antibody Characterization

A. Hit Confirmation and Specificity

Supernatants from transiently transfected mammalian cell lines were used to test for immunoglobulin (Ig) expression, antigen specificity, and antigen affinity. These assays were ELISA-based, using reagents that recognize IgG, as well as the soluble ECD of PD-1 as an Fc-fusion protein (SinoBiological "CD279-Fc"). While the screening immunogen was the soluble form of PD-1, the form used for binding confirmation was a fusion protein comprising the ECD of human PD-1 with a human Fc domain. Other immune checkpoint proteins in the same biochemical configurations were used as specificity controls, e.g., CD28, GITR. Proteins were immobilized in wells of a 96 well assay plate (Nunc MAXISORB) and supernatants from transfected HEK293 cells were used to assess binding of reformatted anti-PD-1 antibodies, produced as described above. These experiments enabled determination of binding specificity and affinity.

Figure 3:
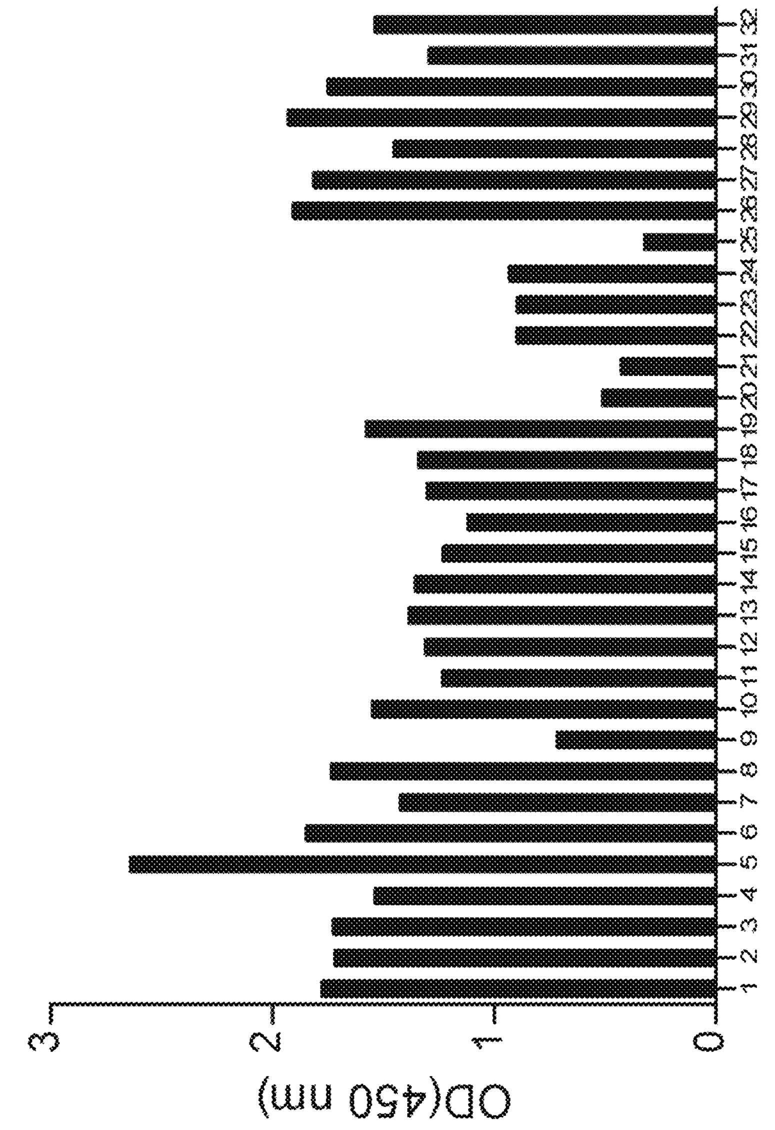
FIG. 3 is a bar graph summarizing data on binding of 32 mouse anti-human-PD-1 antibodies to PD-1-HIS. The specific HCVR and LCVR pairings for the 32 antibodies are indicated in the boxed text. Binding was evaluated by ELISA. Data represent average of two experiments.

FIG. 3 shows an example of an ELISA-based binding assay. Various VH and VK were paired to yield 32 clones (clone pairings shown in box of FIG. 3), which were expressed in HEK293 cells and assayed for binding to PD-1-HIS(tag). The results represent an average of two experiments.

B. Cellular Binding

Recombinant antibodies from cultured supernatants were also used in cell-based binding studies. HEK293 cells were transfected (Qiagen, SuperFect) with expression plasmids encoding the Ig heavy and light chains of anti-PD-1 antibodies. After 3-5 days, recombinant antibodies in the supernatants of transfected cells were harvested. Stable HEK293 cells expressing human PD-1 or primary cells were used for the cell-based binding confirmation studies. Antibodies from cultured supernatants were assessed for binding to cell surface PD-1 using fluorescently labeled anti-mouse IgG (polyclonal) antibody (Jackson Immunoresearch).

Fluorescence microscopy studies revealed that a number of anti-PD-1 antibodies obtained from transfection supernatants bound to PD-1 expressed on the surface of HEK293 cells. Binding of four mouse anti-PD-1 antibodies including, 100244_C7VH10_100245_C8VK5m1 (comprising the HCVR corresponding to SEQ ID NO: 4 and LCVR corresponding to SEQ ID NO: 27), were detected with anti-mouse κ-PE (secondary antibody). Similarly, in a separate study, binding of five mouse anti-PD-1 antibodies including, 100392_C5VH6_100393_C5VK7, comprising the HCVR corresponding to SEQ ID NO: 9 and LCVR corresponding to SEQ ID NO: 38, were detected with anti-mouse IgG1-AF488 (secondary antibody). In both studies, commercially available mouse anti-PD-1 antibody and isotype control mouse IgG1 anti-PD-1 were used as controls. Table 3 summarizes results of tests of binding of various anti-PD-1 antibodies to PD-1 expressed on the surface of HEK293 cells. Strong binding is denoted as "+++", medium binding is denoted as "++", and weak binding is denoted as "+".

TABLE 3

| Summary of PD-1 mAb binding to cell-surface expressed PD-1 | | |
|---|---|---|
| Mouse anti-human PD-1 Abs | Binding to Human PD-1 Expressed on HEK293 Surface | mAb Name |
| 100244_C7VH10_100245_C8VK5 | ++ | 244C7 |
| 100244_C7VH10_100245_C8VK5m1 | ++ | 244C7m1 |
| 100244_C8VH3_100245_C8VK5 | ++ | 244C8 |
| 100244_C8VH3_100245_C8VK5m1 | ++ | 244C8m1 |
| 100246_F7VH3_100247_F7VK2 | ++ | 246F7 |
| 100258_C1VH4_100259_C1VK1 | + | 258C1 |
| 100258_F6VH4_100259_F6VK1 | ++ | 258F6 |
| 100258_F6VH4_100259_F6VK1m1 | ++ | 258F6m |
| 100392_C4VH5_100393_C4VK8 | +++ | 392C4 |
| 100394_D5VH9_100395_D5VK7 | ++ | 394D5 |
| 100394_G1VH1_100395_G1VK4 | ++ | 394G1 |
| 100388_C1VH2_100389_C1VK1 | ++ | 388C12A |
| 100388_C1VH2_100389_C1VK2 | ++ | 388C12B |
| 100388_C1VH6_100389_C1VK1 | ++ | 388C16A |
| 100388_C1VH6_100389_C1VK2 | ++ | 388C16B |
| 100388_G1VH5_100389_G1VK1 | – | 388G1 |
| 100392_B4VH10_100393_B4VK10 | – | 392B4 |
| 100392_C5VH6_100393_C5VK7 | ++ | 392C5A |
| 100392_C5VH6_100393_C5VK10 | ++ | 392C5B |

TABLE 3-continued

Summary of PD-1 mAb binding to cell-surface expressed PD-1

| Mouse anti-human PD-1 Abs | Binding to Human PD-1 Expressed on HEK293 Surface | mAb Name |
|---|---|---|
| 100392_D2VH7_100393_D2VK6 | ++ | 392D2 |
| 100392_H3VH6_100393_H3VK2 | − | 392H3 |
| 100392_H4VH9_100393_H4VK6 | + | 392H4 |
| 100394_F1VH8_100395_F1VK4 | − | 394F1 |
| 100246_A10VH1_100247_A10VK3 | +++ | 246A10 |
| 100388_D4VH3_100389_D4VK5 | +++ | 388D4 |
| 100388_H4VH1_100389_H4VK4 | − | 388H4 |
| 100392_A6VH8_100393_A6VK5 | ++ | 392A6 |
| 100392_C3VH7_100393_C3VK10 | − | 392C3 |
| 100411_C2VH3_100412_C2VK7 | ++ | 411C2 |
| 100413_D2VH9_100414_D2VK6 | ++ | 413D2 |
| 100413_E1VH9_100414_E1VK5 | ++ | 413E1 |
| 100413_H1VH3_100414_H1VK6 | − | 413H1 |
| mouse anti-PD-1 cl. EH12.2H7 (1 μg/mL) | ++ | n/a |
| isotype control mouse IgG1(1 μg/mL) | − | n/a |

C. Cell-Based Activity

Antibodies that recognize PD-1 with high affinity were selected for use in cell-based assays to test for agonist and antagonist activity. Using standard ex vivo activation conditions with primary human cells, selected anti-PD-1 antibodies were used for cell-based assays in microwell array devices, using conditions that have been previously characterized (see, e.g., Varadarajan et al., 2012, *Proc. Nat'l Acad. Sci.* 109:3885-3890) to assess effects of these antibodies on effector cell function.

Peripheral blood mononuclear cells (PBMCs) obtained from de-identified donors via a commercial source were used in these studies. PBMCs were placed into wells of a 96-well assay plate previously coated with plate bound anti-CD3 (OKT3) at a concentration of 1 μg/mL. In addition to TCR-mediated stimulation, cells were treated with PBS (control), soluble recombinant human PD-L1 (shPD-L1) (SinoBiological) at 20 μg/mL, or shPD-L1 with anti-PD-1 antibody (10 μg/mL). Cellular proliferation was assayed by ELISA for IL-2 (R&D Systems, #D2050) in the supernatant of cell cultures, or by direct measurement of secreted IFNγ at the single cell level (Varadarajan, supra) using microwell array devices.

Figure 4:
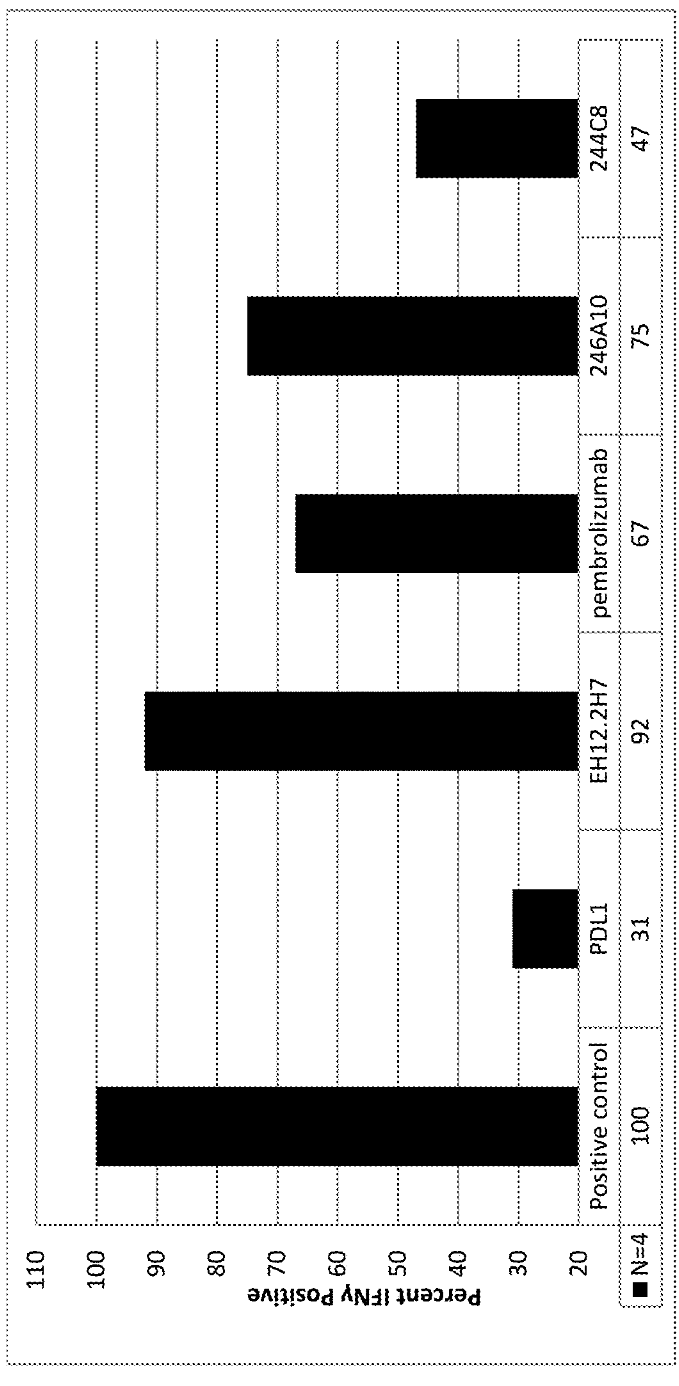
FIG. 4 is a bar graph summarizing results from assays to measure the effectiveness of anti-PD-1 antibodies in relieving PD-L1 dependent inhibition of activation of human peripheral blood mononuclear cells (PBMCs). Treatments of cells were carried out in 96-well plates for 3-5 days. All treatments included plate-bound CD3 and soluble CD28 in PBS. Cells were treated additionally with nothing (positive control); with PD-L1 alone; or with PD-L1 plus an anti-PD-L1 antibody (EH12.2H7, pembrolizumab, 246A10 or 244C8). At the end of the treatment period, cells were transferred to a microwell array for IFNγ determination at the level of individual cells, with sample cell populations in the range of approximately 50-100 cells.

FIG. 4 summarizes results from assays to measure the effectiveness of anti-PD-1 antibodies in relieving PD-L1 dependent inhibition of activation of human peripheral blood mononuclear cells (PBMCs). Treatments of cells were carried out in 96-well plates for 3-5 days. All treatments included plate-bound CD3 and soluble CD28 in conventional media. Cells were treated additionally with nothing (positive control); with PD-L1 alone; or with PD-L1 plus an anti-PD-1 antibody (EH12.2H7 (BioLegend Products, San Diego, CA), j105 (eBioscience, San Diego, CA), pembrolizumab, 246A10 or 244C8). At the end of the treatment period, cells were transferred to a microwell array device for IFNγ determination at the level of individual cells, with sample cell populations in the range of approximately 50-100 cells. The results shown in FIG. 4 illustrate antagonism of PD-1 activity by anti-PD-1 antibodies. These anti-PD-1 antibodies blocked the inhibitory effect of PD-L1, thus decreasing PD-1/PD-L1 (or PD-1/PD-L2) mediated inhibition of cellular immune response.

D. Differential T Cell Activation

Figure 5:
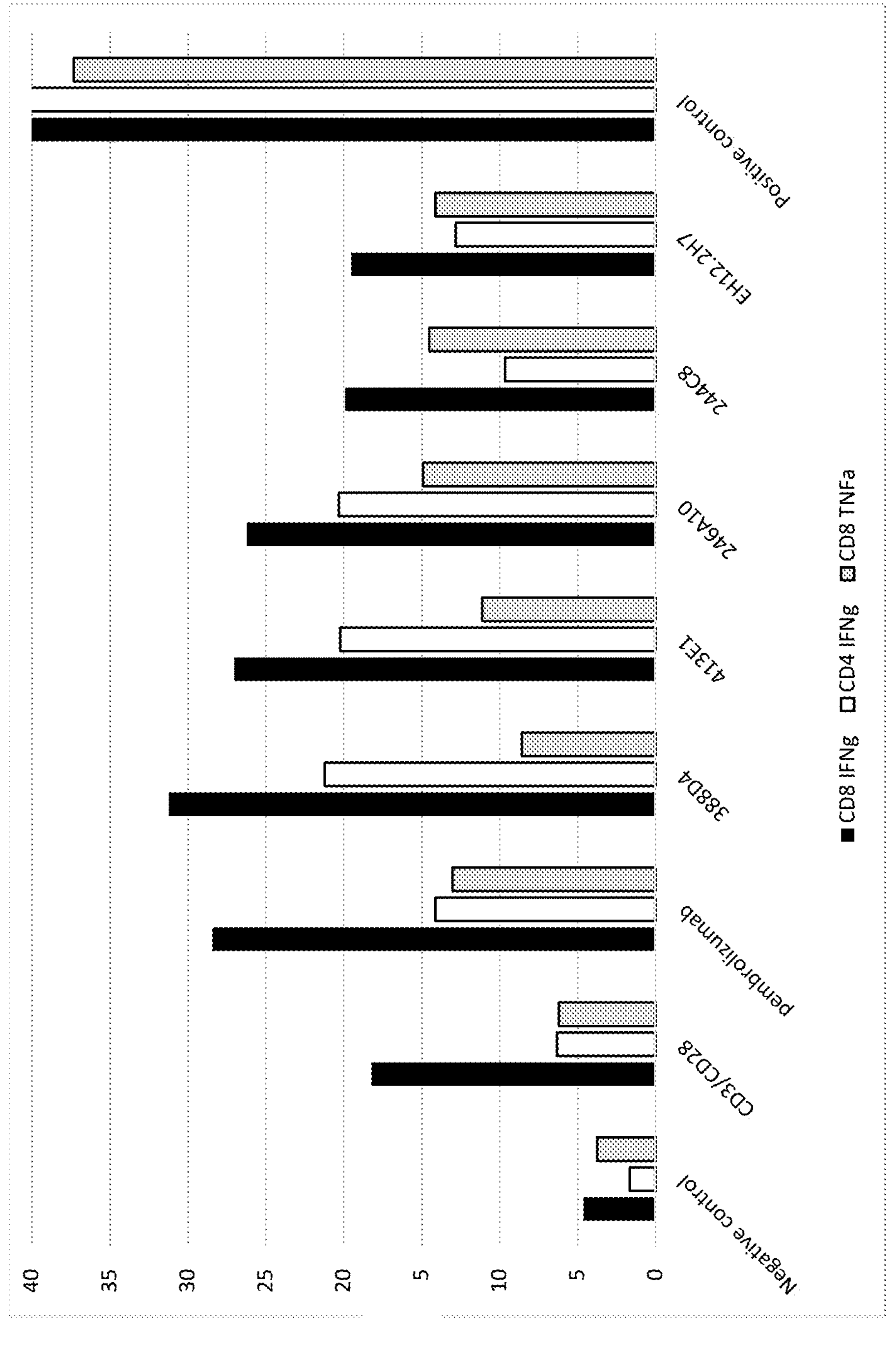
FIG. 5 is a bar graph summarizing the results of differential T cell activation in response to PD-1 blockade. These results indicate that antibodies 388D4, 413E1, 246A10 and 244C8 elicited similar secretion levels or enhanced secretion levels of IFNγ and TNFα as compared to antibody EH12.2H7 or pembrolizumab, under conditions of suboptimal activation (achieved by the treatment with anti-CD3 and anti-CD28), which may mimic activation conditions that occur in vivo.

In a first type of cell-based activation assay, commercially-sourced human PBMCs (peripheral blood mononuclear cells) (Research Blood Components, Allston, MA) were analyzed by flow cytometry to test for differential T cell activation in response to PD-1 blockade by different anti-PD-1 antibodies in vitro. CD4 and CD8 were used as T cell markers. The relative extent of T cell activation was inferred from measuring production of the effector cytokines, interferon gamma (IFNγ) and tumor necrosis factor-alpha (TNFα). The experiments were conducted essentially as follows. Approximately 500,000 to 750,000 PBMCs were incubated for three days in the presence of 1 μg/mL anti-CD3 (clone HIT3a), 50 ng/mL anti-CD28 (clone CD28.2) and 20 μg/mL anti-PD-1 antibody or isotype control. At the end of the 3-day incubation period, cells were treated with Brefeldin A for 6 hours and then subjected to extracellular staining for CD4, CD8, CD69, CD25, PD-L1, or other extracellular markers conjugated to fluorophores. Cells were then fixed, permeabilized, and stained for intracellular markers including IFNγ (antibody clone 4S.B3). Data were collected by flow cytometry using a FACSCALIBUR™ flow cytometer (Becton Dickinson, Franklin Lakes, NJ), and analyzed using FLOWJO™ software (FlowJo, LLC, Ashland, OR). The antibodies tested were pembrolizumab, clone EH12.2H7 (BioLegend), and anti-PD-1 antibodies 388D4, 413E1, 246A10 and 244C8 of the present invention. Under conditions of suboptimal activation (achieved by the treatment with anti-CD3 and anti-CD28), which may mimic activation conditions that occur in vivo, antibodies 388D4, 413E1, 246A10 and 244C8 in these tests elicited similar secretion levels, or enhanced secretion levels of IFNγ and TNFα, as compared to EH12.2H7 or pembrolizumab (Table 4). The data in Table 4 are compared graphically in FIG. 5.

TABLE 4

Summary of differential T cell activation in response to PD-1 blockade by different anti-PD-1 antibodies

| | CD8 IFNγ % positive | CD4 IFNγ % positive | CD8 TNFα % positive |
|---|---|---|---|
| Negative control | 4.6 | 1.64 | 3.73 |
| CD3/CD28 | 18.2 | 6.31 | 6.19 |
| pembrolizumab | 28.4 | 14.1 | 13 |
| 388D4 | 31.2 | 21.2 | 8.56 |
| 413E1 | 27 | 20.2 | 11.1 |
| 246A10 | 26.2 | 20.3 | 14.9 |
| 244C8 | 19.9 | 9.64 | 14.5 |
| EH12.2H7 | 19.5 | 12.8 | 14.1 |

TABLE 4-continued

| Summary of differential T cell activation in response to PD-1 blockade by different anti-PD-1 antibodies | | | |
|---|---|---|---|
| | CD8 IFNγ % positive | CD4 IFNγ % positive | CD8 TNFα % positive |
| Positive control | 73.7 | 61.5 | 37.3 |

Figure 6:
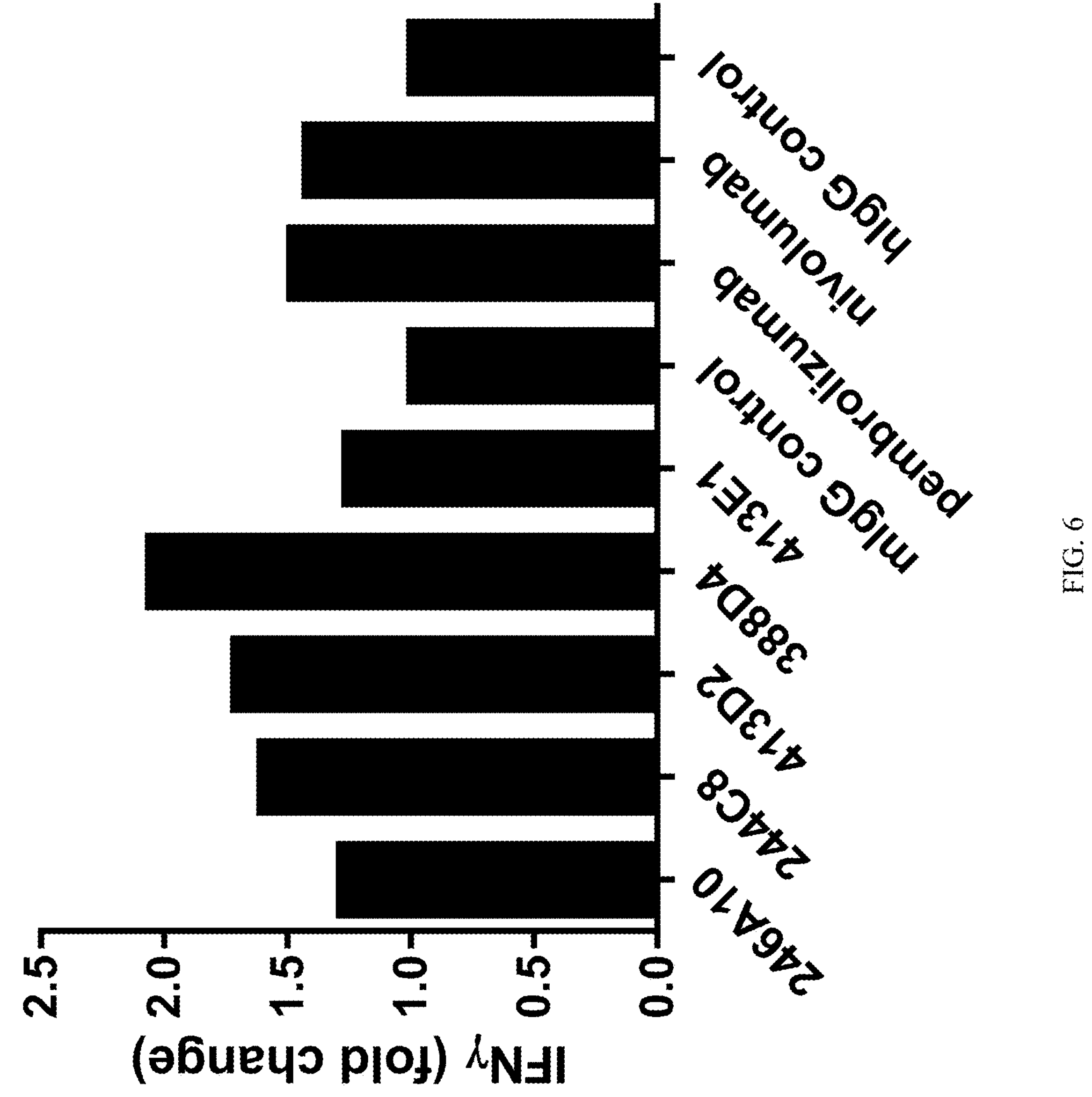
FIG. 6 is a bar graph summarizing the results of antigen recall assays using cytomegalovirus in human PBMC. These results indicate that anti-PD-1 antibodies 246A10, 244C8, 413D2, 388D4, and 413E1 induce increased levels of IFNγ compared to antibody isotype controls.
Figure 9A:
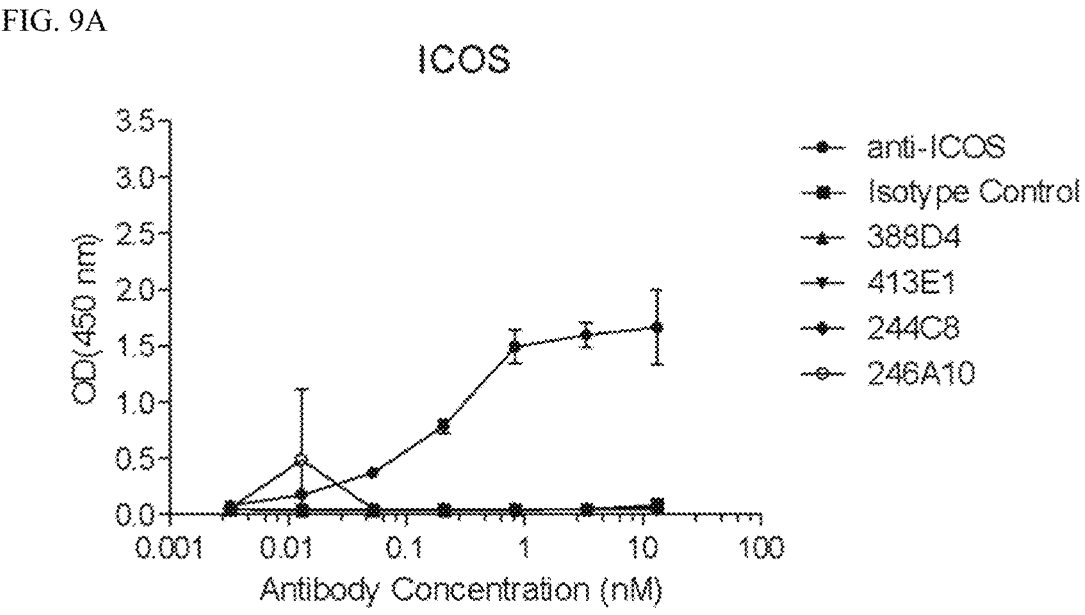
FIGS. 9A-9D show selectivity of anti-PD-1 antibodies for the PD-1 extracellular domain over other immunomodulatory cell surface proteins such as ICOS (inducible T-cell costimulator) (FIG. 9A), CD28 (FIG. 9C), or CTLA4 (FIG. 9D). Binding of anti-PD-1 antibodies to PD-1 is shown in FIG. 9B (EH12.2H7 is an anti-PD-1 antibody commercially available as a laboratory reagent). Anti-PD-1 antibodies 388D4 (100388_D4VH3_100389_D4VK5 in Table 3), 413E1 (100413_E1VH9_100414_E1VK5 in Table 3), 244C8, and 246A10 were tested.
Figure 9B:
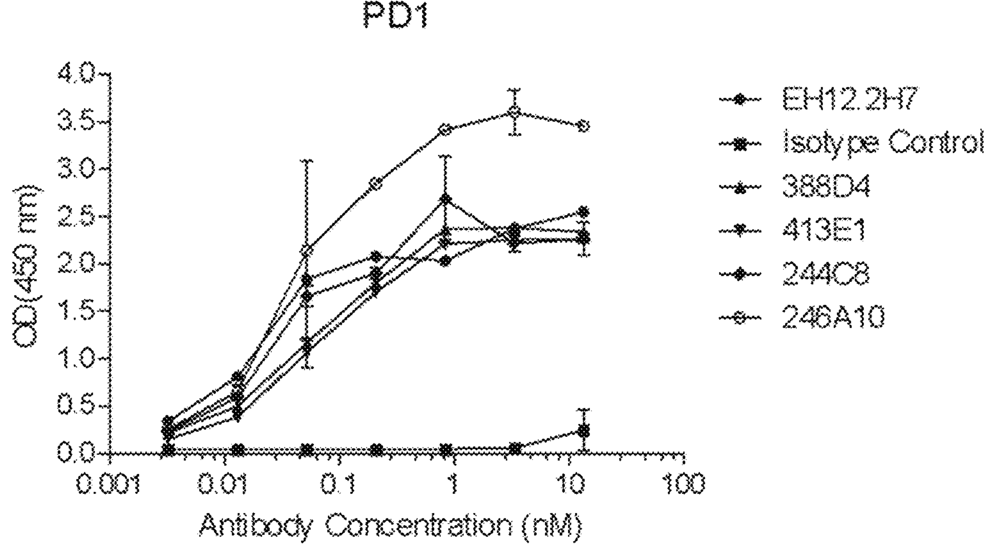
Figure 9C:
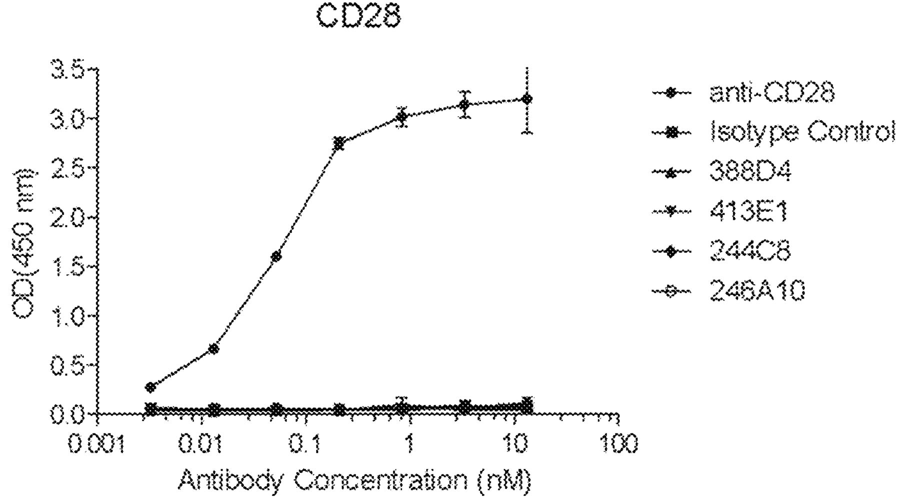
Figure 9D:
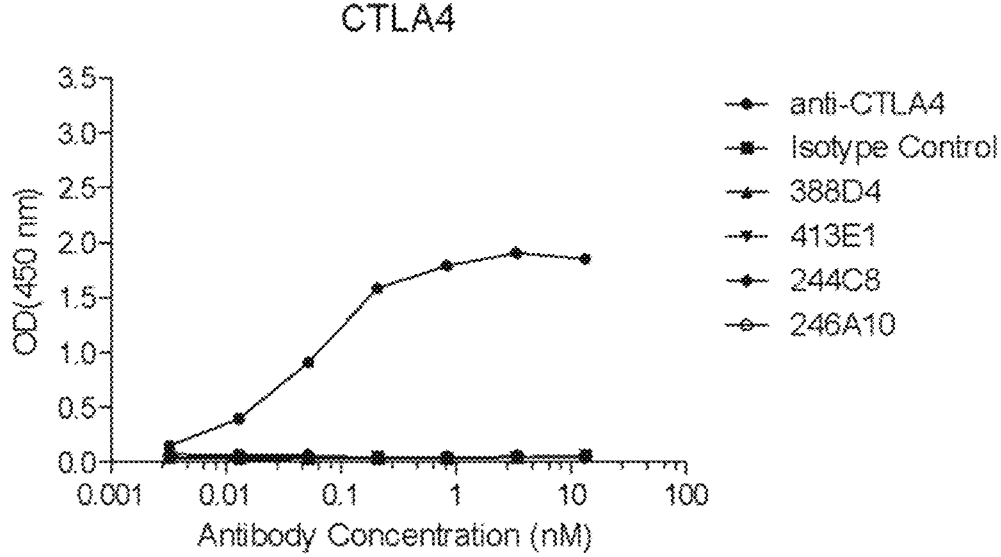
Figure 11A:
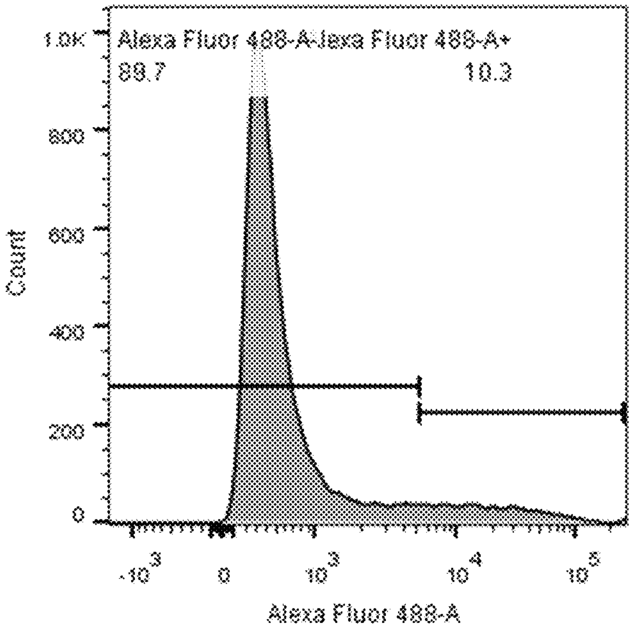
FIGS. 11A-11D are flow cytometry histogram plots showing that antibody 388D4 blocks binding of soluble PD-L1 to HEK293 cells expressing PD-1, while antibody 244C8 does not. HEK293 cells expressing PD-1 were incubated with 10 μg/ml of an isotype antibody (negative control), commercially available antibody EH12.2H7 (positive control) antibody 388D4, or antibody 244C8. Cells were washed and stained with soluble PD-L1-Ig protein fluorescently labeled with Alexa-488. Cells were washed again, and PD-L1 binding (by displacing previously bound antibody) was assessed by conventional fluorescence activated cell sorting (FACS) analysis.
Figure 11B:
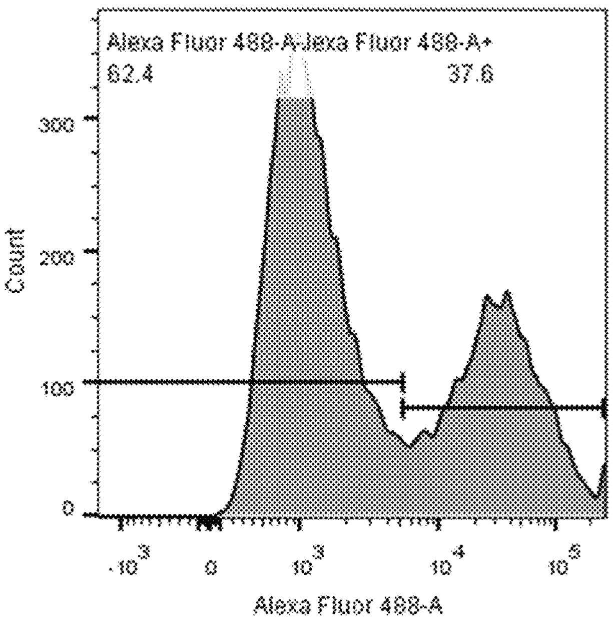
Figure 11C:
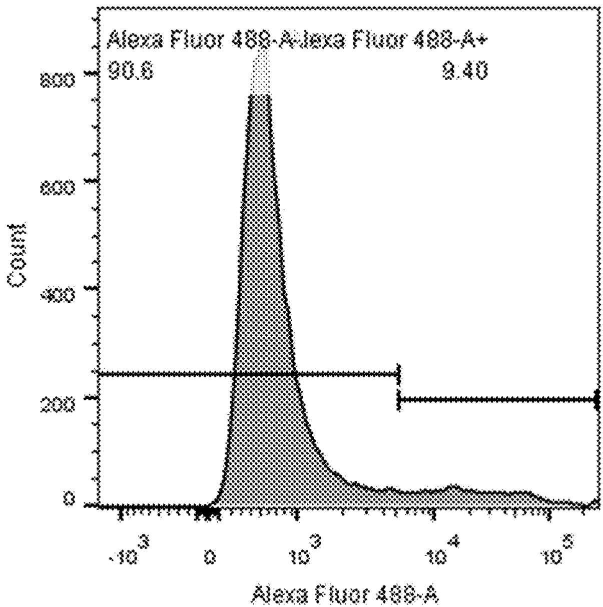
Figure 11D:
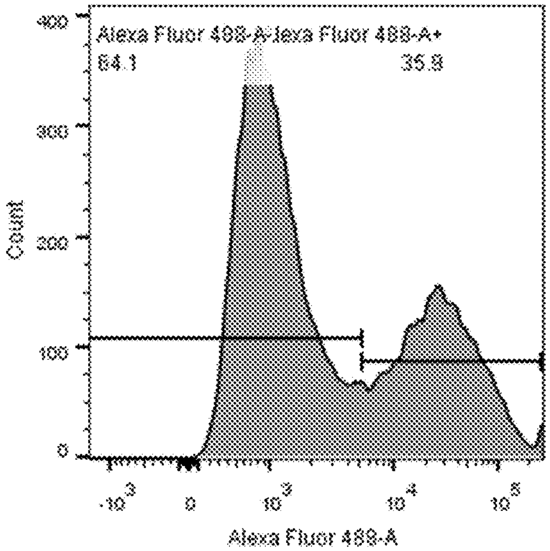

In a second set of experiments, human PBMCs were tested for reactivity in antigen recall assays using CMV (cytomegalovirus) (IMMUNOSPOT®, Shaker Heights, OH). PBMCs were purified from whole blood of healthy donors (Research Blood Components, Allston, MA). The PBMCs were incubated with ready-to-use peptide antigen solutions (Astarte Biologics, Bothell, WA) without or with anti-PD-1 antibodies. Two commercial stage anti-PD-1 antibodies, pembrolizumab and nivolumab, were used as benchmarks for this experiment. Compared to antibody isotype control(s), anti-PD-1 antibodies induce increased levels of IFNγ, a key effector cytokine in T cell antigen recall biology (FIG. 6).

In a third set of experiments, anti-PD-1 antibodies were used with PBMCs in MLR (mixed lymphocyte reaction) assays. In these assays, secretion of IL-2 or IFNγ was the experimental cytokine readout (FIG. 7A). Activation markers such as CD25 were also evaluated (FIG. 7B). Results are summarized in FIGS. 7A and 7B. In this assay, clone 388D4 appears to induce cytokine release and CD25 upregulation similar to nivolumab. In multiple assays, clone 244C8 appears to induce increased levels of cytokine release (IFNγ) compared with 388D4 or nivolumab. T cells incubated with 244C8 also appear to exhibit a higher degree of activation as inferred from CD25 expression (FIG. 7B).

These data indicate that some of the anti-PD-1 antibodies of the present invention, e.g., 388D4, induce increased cytokine release in a manner similar to pembrolizumab and nivolumab, while other antibodies, e.g., 244C8, elicit physiological responses that are measurably different from the responses elicited by pembrolizumab and nivolumab.

E. Peptide-Based Epitope Mapping

Synthetic overlapping peptides based on the human PD-1 sequence (15-mers) (Sigma-Aldrich PEPscreen, Saint Louis, MO) were used in epitope mapping experiments. The peptides used are listed in Table 5 below.

TABLE 5

Human PD-1 peptide sequences used for epitope mapping

| Peptide Name | N-term mod | Sequence | C-term Mod | SEQ ID NO: |
|---|---|---|---|---|
| PD101 | [H] | MQIPQAPWPVVWAVL | [OH] | 54 |
| PD102 | [H] | APWPVVWAVLQLGWR | [OH] | 55 |
| PD103 | [H] | VWAVLQLGWRPGWFL | [OH] | 56 |
| PD104 | [H] | QLGWRPGWFLDSPDR | [OH] | 57 |
| PD105 | [H] | PGWFLDSPDRPWNPP | [OH] | 58 |
| PD106 | [H] | DSPDRPWNPPTFSPA | [OH] | 59 |
| PD107 | [H] | PWNPPTFSPALLVVT | [OH] | 60 |
| PD108 | [H] | TFSPALLVVTEGDNA | [OH] | 61 |
| PD109 | [H] | LLVVTEGDNATFTCS | [OH] | 62 |
| PD110 | [H] | EGDNATFTCSFSNTS | [OH] | 63 |
| PD111 | [H] | TFTCSFSNTSESFVL | [OH] | 64 |
| PD112 | [H] | FSNTSESFVLNWYRM | [OH] | 65 |
| PD113 | [H] | ESFVLNWYRMSPSNQ | [OH] | 66 |
| PD114 | [H] | NWYRMSPSNQTDKLA | [OH] | 67 |
| PD115 | [H] | SPSNQTDKLAAFPED | [OH] | 68 |
| PD116 | [H] | TDKLAAFPEDRSQPG | [OH] | 69 |
| PD117 | [H] | AFPEDRSQPGQDCRF | [OH] | 70 |
| PD118 | [H] | RSQPGQDCRFRVTQL | [OH] | 71 |
| PD119 | [H] | QDCRFRVTQLPNGRD | [OH] | 72 |
| PD120 | [H] | RVTQLPNGRDFHMSV | [OH] | 73 |
| PD121 | [H] | PNGRDFHMSVVRARR | [OH] | 74 |
| PD122 | [H] | FHMSVVRARRNDSGT | [OH] | 75 |
| PD123 | [H] | VRARRNDSGTYLCGA | [OH] | 76 |
| PD124 | [H] | NDSGTYLCGAISLAP | [OH] | 77 |
| PD125 | [H] | YLCGAISLAPKAQIK | [OH] | 78 |
| PD126 | [H] | ISLAPKAQIKESLRA | [OH] | 79 |
| PD127 | [H] | KAQIKESLRAELRVT | [OH] | 80 |
| PD128 | [H] | ESLRAELRVTERRAE | [OH] | 81 |
| PD129 | [H] | ELRVTERRAEVPTAH | [OH] | 82 |
| PD130 | [H] | ERRAEVPTAHPSPSP | [OH] | 83 |
| PD131 | [H] | VPTAHPSPSPRPAGQF | [OH] | 84 |

Each peptide was incubated with each antibody for one hour, to allow peptide-antibody complex formation. Then each of these antibody-peptide mixtures was used in a conventional ELISA, in which human PD-1 was immobilized on 96-well plates. ELISA plates were coated with 100 ng/well of PD-1-His Tag (Sino Biological, North Wales, PA; #10377-H08H-50) in carbonate buffer, pH 9.6. After washing, plates were blocked with 4% milk PBS, 0.05% Tween-PBS (blocking buffer). After blocking and washing of the plates, the peptide-antibody mixtures were incubated with the immobilized human PD-1. After washing, the plates were developed by incubation for 1 hour with goat HRP-conjugated anti-mouse IgG (Jackson ImmunoResearch, West Grove, PA; #115-035-071) and addition of 100 μl of TMB solution (ThermoScientific, Waltham, MA; #PI-34022). Optical densities were measured at the appropriate wavelength, using an ELISA microplate reader. This enabled quantitative assessment of which peptides complexed with the antibody and then inhibited antibody binding to human PD-1. FIG. 8 summarizes the binding results of five antibody clones (246A10, 244C8, 388D4, 413D2, and 413E1).

F. Biophysical Characterization of Anti-PD-1 Antibodies

Biophysical characteristics of certain anti-PD-1 antibodies were analyzed by biolayer interferometry (BLI), using the ForteBio Octet Red system (Pall Corporation, Menlo Park, CA). The antibodies were immobilized on BLI biosensors and then incubated with the soluble extracellular domain of human PD-1. Using standard biophysics methods, apparent on-rates and off-rates were then inferred for PD-1 with anti-PD-1 antibodies. These values were used to generate apparent affinity values ($K_D$ values), which are listed in Table 6.

TABLE 6

| IgG | $K_D$ (nM) | $K_{on}$ (1/Ms) | $K_{dis}$ (1/s) | $R_{max}$ | Full $X^2$ | Full $R^2$ |
|---|---|---|---|---|---|---|
| 246A10 | 76.4 | $1.61 \times 10^5$ | $1.23 \times 10^{-2}$ | 0.10 | 0.01 | 0.99 |
| 244C8 | 15.1 | $2.13 \times 10^5$ | $3.22 \times 10^{-3}$ | 0.12 | 0.01 | 1.00 |
| 413D2 | 8.20 | $2.75 \times 10^5$ | $2.26 \times 10^{-3}$ | 0.15 | 0.02 | 0.99 |
| 393C5 | 2.44 | $4.75 \times 10^5$ | $1.16 \times 10^{-3}$ | 0.15 | 0.01 | 1.00 |
| 388D4 | 2.69 | $3.71 \times 10^5$ | $9.99 \times 10^{-4}$ | 0.16 | 0.01 | 1.00 |
| 413E1 | 58.9 | $5.07 \times 10^5$ | $2.99 \times 10^{-2}$ | 0.12 | 0.01 | 0.99 |

G. Selectivity of Anti-PD-1 Antibodies

To assess selectivity of the anti-PD-1 antibodies, ELISA was used to generate dose response curves for binding of the anti-PD-1 antibodies to several immunomodulatory cell surface proteins. Recombinant soluble extracellular domains (ECDs) of ICOS (inducible T-cell costimulator), PD-1, CD28 or CTLA4 (R&D Systems, Minneapolis, MN) were coated onto ELISA assay plates. Binding of each anti-PD-1 antibody and each control antibody to each target protein was then assessed over a range of antibody concentrations (FIGS. 9A-9D).

These experiments demonstrated that anti-PD-1 antibodies 388D4, 413E1, 244C8 and 246A10 bind to the PD-1 ECD with high specificity, showing no binding to three structurally related Ig-superfamily protein members

Example 3. Humanization of Anti-PD-1 Antibodies

Humanization of selected anti-PD-1 antibodies was performed in order to reduce the apparent immunogenicity of the mouse-based antibodies. Using antibody engineering information well known in the art, and conventional bioinformatics tools, amino acid sequences of certain murine anti-PD-1 antibodies of the invention were analyzed and compared against known human antibody sequences. Based on these analyses and comparisons, certain human sequences were chosen for conventional murine CDR grafting, and inclusion of suitable back mutations. In tests for binding to human PD-1, these humanized antibodies were evaluated with respect to criteria such as affinity, avidity, binding kinetics, and biochemical behavior such as aggregation as well as expression levels. The HCVR and LCVR amino acid sequences of certain humanized antibodies displaying desirable characteristics (e.g., binding to PD-1) are shown in Tables 7 and 8, respectively. FIGS. 10A and 10B show amino acid sequence alignments of the humanized heavy or light chain variable region sequences with the indicated murine heavy (100388_D4_VH3 or 100244_C8_VH3) or light chain (100389_D4_VK5 or 100245_C8_Vk5m1) variable region sequences.

TABLE 7

Humanized heavy chain variable region sequences

| HCVR designation | Amino Acid Sequence | SEQ ID NO: |
|---|---|---|
| 100244_C8_HC1 | QVQLVQSGAEVKKPGASVKVSCKASGYTFT SYWMHWVRQAPGQGLEWMGMIDPSNSETSL NQKFQGRVTMTVDKSTNTVYMELSSLRSED TAVYYCARSRGNYAYEMDYWGQGTLVTVSS | 85 |
| 100244_C8_HC2 | EVQLVQSGAEVKKPGASVKVSCKASGYTFT SYWMHWVRQAPGQGLEWMGMIDPSNSETSL NQKFQGRVTLNVDKSTNTAYMELSSLRSED TAVYYCARSRGNYAYEMDYWGQGTLVTVSS | 86 |
| 100244_C8_HC3 | EVQLVQSGTEVTKPGASVKVSCKASGYTFT SYWMHWVRQAPGQGLEWLGMIDPSNSETTL NQKFQGRVTMTVDKSTNTVYMELTSLRSED TAVYYCARSRGNYAYEMDYWGQGTLVTVSS | 87 |
| 100388_D4_HC1 | EVQLVQSGAEVKKPGASVKVSCKASGYTFT DYEMHWVRQAPGQGLEWMGIIDPGTGGTAY NQKFQGRVTMTADKSTSTVYMELSSLRSED TAVYYCTSEKFGSNYYFDYWGQGTLVTVSS | 88 |
| 100388_D4_HC2 | EVQLVQSGAEVKKPGASVKVSCKASGYTFT DYEMHWVRQAPGQGLEWMGIIDPGTGGTAY NQKFQGRVTMTADKSTNTVYMELSSLRSED TAVYYCTSEKFGSNYYFDYWGQGTLVTVSS | 89 |
| 100388_D4_HC3 | EVQLVQSGAEVKKPGASVKVSCKASGYTFT DYEMHWVRQAPGQRLEWMGVIDPGTGGT AYNQKFQGRVTITADKSASTAYMELSSLRS EDTAVYYCTSEKFGSNYYFDYWGQGTLVT VSS | 90 |

TABLE 8

Humanized light chain variable region sequences

| LCVR designation | Amino Acid Sequence | SEQ ID NO: |
|---|---|---|
| 100245_C8_LC1 | EIVLTQSPATLSLSPGERATLSCRASSSVS SNYLYWYQQKPGQAPRLLIYSTSNRATGIP ARFSGSGSGTDYTLTISSLEPEDFAVYYCH QWSSYPPTFGQGTKLEIK | 91 |
| 100245_C8_LC2 | DIVLTQSPATLSLSPGERATLSCRASSSVS SNYLYWYQQKPGQAPRLLIYSTSNLATGIP ARFSGSGSGTDYTLTISSLEPEDFAVYFCH QWSSYPPTFGQGTKLEIK | 92 |
| 100245_C8_LC3 | DIVLTQSPGTLSLSPGEKVTLSCRASSSVS SNYLYWYQQKPGQAPRLVIYSTSNLATGIP DRFSGSGSGTDYTLTISRLEPEDFAVYFCH QWSSYPPTFGQGTKVEIK | 93 |
| 100389_D4_LC1 | DVVMTQSPLSLPVTLGQPASISCRSSQTIV HSDGNTYLEWYQQRPGQSPRLLIYKVSNRF SGVPDRFSGSGSGTDFTLKISRVEAEDVGV YYCFQGSHVPLTFGQGTKLEIK | 94 |
| 100389_D4_LC2 | DIVMTQSPLSLPVTLGQPASISCRSSQTIV HSDGNTYLEWYQQRPGQSPKLLIYKVSNRF SGVPDRFSGSGSGTDFTLKISRVEAEDVGV YYCFQGSHVPLTFGQGTKLEIK | 95 |
| 100389_D4_LC3 | DIVMTQTPLSSPVTLGQPASISCRSSQTIV HSDGNTYLEWYQQRPGQPPRLLIYKVSNRF SGVPDRFSGSGAGTDFTLKISRVEAEDVGV YYCFQGSHVPLTFGQGTKLEIK | 96 |

TABLE 9

| HCVR and LCVR pairings for humanized antibodies | | |
|---|---|---|
| Humanized Antibody Designation | Heavy Chain Variable Region | Light Chain Variable Region |
| 244C8-1 | 100244_C8_HC1 (SEQ ID NO: 85) | 100245_C8_LC1 (SEQ ID NO: 91) |
| 244C8-2 | 100244_C8_HC1 (SEQ ID NO: 85) | 100245_C8_LC3 (SEQ ID NO: 93) |
| 244C8-3 | 100244_C8_HC2 (SEQ ID NO: 86) | 100245_C8_LC1 (SEQ ID NO: 91) |
| 388D4-1 | 100388_D4_HC3 (SEQ ID NO: 90) | 100389_D4_LC1 (SEQ ID NO: 94) |
| 388D4-2 | 100388_D4_HC3 (SEQ ID NO: 90) | 100389_D4_LC3 (SEQ ID NO: 96) |
| 388D4-3 | 100388_D4_HC1 (SEQ ID NO: 88) | 100389_D4_LC3 (SEQ ID NO: 96) |

Example 4. Antibody-Ligand Competition for Binding to PD-1

A. Competitive Binding Assays

It was found that while some of the anti-PD-1 antibodies disclosed herein competitively inhibit binding of PD-1 ligands, others do not. For example, in surface plasmon resonance-based competitive binding assays and flow cytometry-based competitive binding assays, it was found that antibody 388D4 competitively inhibits binding of PD-L1 to PD-1, but does not inhibit binding of PD-L2. In contrast, it was found that antibody 244C8 does not competitively inhibit binding of PD-L1 or PD-L2.

Competitive Binding Analysis was performed on humanized IgG4 antibodies 244C8-2 and 388D4-2, using ForteBio Biolayer Interferometry (BLI). Humanized IgG antibody was immobilized to AHC biosensors by loading 3 μg/mL IgG to a target level of 1.0 nm over a 160 second load time. A single concentration (100 nM) of active PD-1, plus an appropriate negative control to correct for drift, was bound the immobilized IgG. A pH of 7.4 was used for association and dissociation. The bound PD-1 was then exposed to seven concentrations of PD-L1 (9, 3, 1, 0.333, 0.111, 0.037, and 0 μM) or PD-L2 (2000, 666.7, 222.2, 74.1, 24.7, 8.2, and 0 nM). The association/dissociation of PD-L1 and PD-L2 to the mAb/PD-1 complex immobilized on biosensor tips was evaluated.

Materials used in these assays were as follows: PD1 (His Tag): ABCAM, Cat #ab174035, Lot #GR199119-1, 100 mg; PD-L1 (His Tag): Sino Biological, Cat #10084-H08H, Lot #LC098E0901, 200 mg; PD-L2 (His Tag): Sino Biological, Cat #10292-H08H, Lot #LC07DE3022, 100 mg; PD1-Fc: R&D Systems, Cat #1086-PD, Lot #FVQ0413051, 50 mg; Anti-Human IgG-Fc Capture (AHC) Biosensors: ForteBio, Cat #18-5060, Lot #1501211; 1× Kinetic Buffer: 20 mM Phosphate, 150 mM NaCl, 0.02% Tween-20, 0.05% Sodium Azide, 0.1 mg/ml BSA, pH 7.4; Test Samples: Humanized $IgG_4$—244C8-2 (3.04 mg/mL), Humanized $IgG_4$—388D4-2 (2.89 mg/mL).

The flow cytometry assays were conducted essentially as follows. HEK293 cells expressing PD-1 were incubated with 10 μg/ml of an isotype antibody (negative control), commercially available antibody EH12.2H7 (positive control), antibody 388D4, or antibody 244C8. Cells were washed and stained with soluble PD-L1-Ig protein fluorescently labeled with Alexa-488. Cells were washed again, and PD-L1 binding (by displacing previously bound antibody) was assessed by fluorescence activated cell sorting (FACS) analysis. Representative results are shown in FIGS. 11A-11D.

Example 5. Human Cell Based Assays

A. Human Cells

Human tumor tissue procurement and tumor dissociation were as follows. Fresh tumor samples from NSCLC patients undergoing surgical resection of tumors were obtained from the Cooperative Human Tissue Network, National Cancer Institute. Analysis was performed using single-cell suspensions of tumor cells from these tumor samples.

Solid tumor biopsy samples were mechanically disrupted into single-cell suspensions using a gentleMACS Dissociator (Miltenyi Biotec) with enzymes A, H and R. The single-cell suspensions were then prepared for cell counting and initial FACS analysis.

B. FACS Analysis

For FACS analysis, anti-CD45-PerCP-Cy5.5 (clone 2D1), anti-CD4-PE-Cy7 (SK3), anti-CD8-FITC (SK1), anti-BTLA-Biotin (MIH26), anti-CTLA-4-PE (14D3), and anti-LAG-3-APC (3DS223H) were purchased from eBioscience. Anti-CD25-BV605 (2A3), anti-PD-1-BV605 (EH121), and Streptavidin-BV711 were purchased from BD Bioscience. Anti-CD45RABV421 (HI100), anti-CCR7 AlexaFluor647 (G043H7), and anti-Tim-3-BV421 (F38-2E2) were purchased from Biolegend. Heterogeneous cell suspensions prepared from dissociated primary tumors (as described above) were washed, resuspended in PBS, and blocked with a commercial Fc blocking reagent (BD Biosciences). Viable cells were identified by lack of dead cell staining positivity, and by negativity for EpCAM expression. CD45-positive cells were gated for CD4 or CD8 expression, and then the cells were assessed for expression of PD-1, TIM3, LAG3 or TIGIT. These FACS data are shown below, in Table 10, with results expressed as percentage of positive cells.

TABLE 10

| Results of FACS analysis | | | | | | | | | | |
|---|---|---|---|---|---|---|---|---|---|---|
| Tumor | % EpCAM- CD45+ | % CD3+ | % $CD4^+$ $PD1^+$ | % $CD8^+$ $PD1^+$ | % $CD4^+$ $TIM3^+$ | % $CD8^+$ $TIM3^+$ | % $CD4^+$ $LAG3^+$ | % $CD8^+$ $LAG3^+$ | % $CD4^+$ $TIGIT^+$ | % $CD8^+$ $TIGIT^+$ |
| WD-36444 | 25.7 | 14 | 55 | 75 | 5.5 | 13 | <1 | <1 | 6 | 6.3 |
| WD-36571 | 10.3 | 6.3 | 47 | 64 | 1.8 | <1% | 0 | 0 | 12.6 | 21 |
| WD-36686 | 21.6 | 17 | 55 | 84 | 6 | 16 | 0 | 0 | 20 | 15 |

TABLE 10-continued

Results of FACS analysis

| Tumor | % EpCAM- CD45+ | % CD3+ | % CD4$^+$ PD1$^+$ | % CD8$^+$ PD1$^+$ | % CD4$^+$ TIM3$^+$ | % CD8$^+$ TIM3$^+$ | % CD4$^+$ LAG3$^+$ | % CD8$^+$ LAG3$^+$ | % CD4$^+$ TIGIT$^+$ | % CD8$^+$ TIGIT$^+$ |
|---|---|---|---|---|---|---|---|---|---|---|
| WD-36790 | 16.8 | 10.4 | 38 | 68 | 1 | 5.2 | <1 | <1 | 33 | 47 |
| WD-36904 | 12.8 | 7 | 63 | 72 | 9.5 | 24.5 | <1 | <1 | 41 | 25.6 |
| M115801A2 | 3.4 | 2.9 | 79 | 84 | 22 | 16 | 1.4 | 1.6 | 56 | 35 |
| WD-36923 | 1.6 | 0.9 | 53 | 51 | 27 | | | | 24.5 | |
| WD-36988 | 8.9 | 7 | 58 | 93 | 22 | 62 | 0 | 0 | 25 | 52 |
| M4150952 | 5.4 | 3 | 78 | 79 | 26 | 15 | 0 | 0 | 32 | 23 |

The T cell surface marker expression data in Table 10 provide a comparison of the immunomodulatory receptor profiles of tumor infiltrating lymphocytes (TILS) from various human NSCLC tumor biopsy samples. Such data provided a useful biological context for the assays performed using the tumor samples.

C. Stimulation of Tumor Infiltrating Lymphocytes (TILs)

To establish polyclonal stimulation of TILs among the dissociated tumor cells, a 96-well assay plate was coated with 0.5 μg/mL anti-CD3 (OKT3) in coupling buffer, overnight at 4° C. The antibody coating solution was removed, and the plate was washed. Tumor suspensions were resuspended to a density of approximately $1.5\times10^6$ cells per mL. Then 200 μL of this was added to each experimental well, together with 2 μg/mL anti-CD28 (clone 28.2, eBioscience). At specific time points, supernatants were used for ELISA analysis or cells were used for FACS analysis or single cell analysis on microwell array devices.

D. Enzyme-Linked Immunosorbent Assay

Supernatants from cultured tumor digests containing tumor cells, stromal cells and immune cells were collected at fixed time points after experimental treatment, and cytokine production was assessed by ELISA. To begin the ELISA, 96-well plates were coated with capture antibody, blocked with assay diluent buffer, and washed, prior to incubation with serial dilutions of supernatants from the cultured tumor-derived cells. The samples were incubated for one hour, and then the ELISA plates were washed. The detection antibody-HRP, in assay diluent, was then added, the assay plate was washed, and substrate solution was added to the wells in the assay plate. After the enzyme reaction was stopped, colorimetric density at 450 nm was measured in a conventional plate reader. Measurements of IFNγ secretion, normalized to internal standards included on each plate, was used as the experimental readout for T cell effector function.

E. TIL Function Increased by PD-1 Blockade

Figure 12:
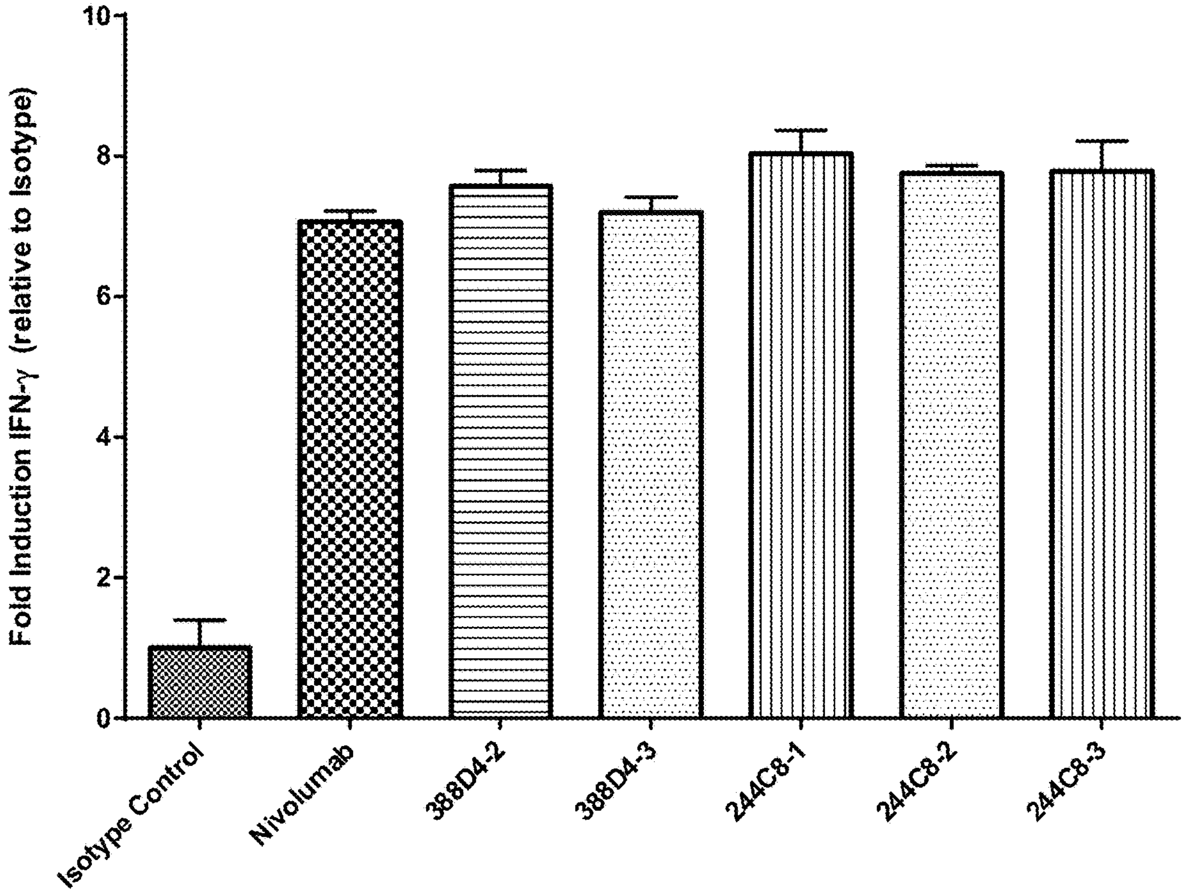
FIG. 12 is a histogram showing restoration of T cell function by PD-1 blockade with nivolumab or different humanized forms of antibodies 388D4 and 244C8, i.e., 388D4-2, 388D4-3, 244C8-1, 244C8-2, and 244C8-3. A population of $3\times10^5$ dissociated and suspended human cells from a non-small cell lung cancer (NSCLC) biopsy, which included 17% lymphocytes (activated as described above) was incubated for 24 hours with anti-PD-1 antibodies at a concentration of 20 μg/mL. IFNγ was measured by ELISA, and the data are expressed in terms of fold-activation relative to treatment with the isotype control antibody. Each of the anti-PD-1 antibodies restored T cell function, increasing IFNγ secretion approximately 7-fold to 7.5 fold, relative to the isotype control.

FIG. 12 summarizes results from an experiment showing restoration of T cell function by PD-1 blockade with nivolumab or different humanized forms of antibodies 388D4 and 244C8, i.e., 388D4-2, 388D4-3, 244C8-1, 244C8-2, and 244C8-3. A population of $3\times10^5$ cells, which included 17% lymphocytes (activated as described above) was incubated for 24 hours with anti-PD-1 antibodies at a concentration of 20 μg/mL. IFNγ was measured by ELISA, and the data were expressed in terms of fold-activation relative to treatment with the isotype control antibody. As shown in FIG. 12, each of the anti-PD-1 antibodies restored T cell function, increasing IFNγ secretion approximately 7- to 8-fold, relative to the isotype control. The data illustrated in FIG. 12 are presented in Table 11 below.

TABLE 11

Restoration of T cell function by PD-1 blockade

| | Fold Induction IFN-γ | Standard Deviation |
|---|---|---|
| Isotype Control | 1.00 | 0.39 |
| nivolumab | 7.07 | 0.15 |
| 388D4-2 | 7.58 | 0.23 |
| 388D4-3 | 7.20 | 0.23 |
| 244C8-1 | 8.04 | 0.33 |
| 244C8-2 | 7.76 | 0.11 |
| 244C8-3 | 7.79 | 0.42 |

Figure 13:
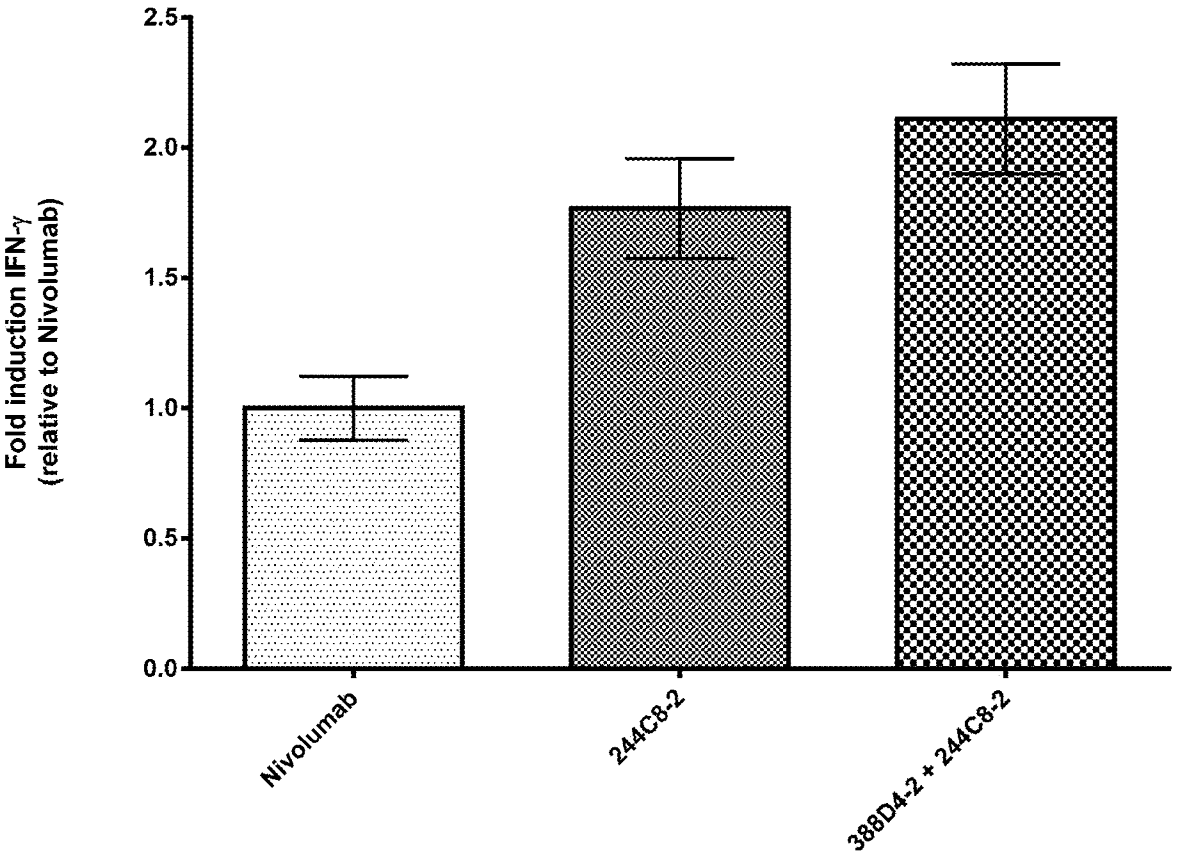
FIG. 13 is a histogram summarizing results from an experiment to measure the increase in T cell effector function, as indicated by IFNγ secretion, in response to treatment with antibody 244C8-2 alone versus treatment with 244C8-2 plus 388D4-2, with results normalized relative to the response to treatment with nivolumab. A population of $3\times10^5$ cells, which included 7.5% lymphocytes sub-optimally activated as described above, was incubated for 24 hours with anti-PD-1 antibodies at a total antibody concentration of 20 μg/mL.

FIG. 13 summarizes results from an experiment to measure the increase in T cell effector function, as indicated by IFNγ secretion, in response to treatment with antibody 244C8-2 alone versus treatment with 244C8-2 plus 388D4-2, with results normalized relative to the response to treatment with nivolumab. A population of $3\times10^5$ cells, which included 7.5% lymphocytes sub-optimally activated as described above, was incubated for 24 hours with anti-PD-1 antibodies at a total antibody concentration of 20 μg/mL. As shown in FIG. 13, treatment with 244C8-2 alone increased IFNγ 1.77-fold (±0.19 sd), while treatment with 244C8-2 in combination with 388D4-2 increased IFNγ secretion 2.11-fold (±0.21 sd). These unexpected results obtained in response to treatment with the combination of a competitive inhibitory antibody and a non-competitive inhibitory antibody indicate that combining these two different mechanisms of action to inhibit PD-1 produces an enhanced response, despite the fact that both antibodies are directed against the same target. The data illustrated in FIG. 13 are presented in Table 12 below.

TABLE 12

Increase in IFN-γ induction by combination of anti-PD-1 antibodies

| | Fold Induction IFN-γ | Standard Deviation |
|---|---|---|
| Nivolumab | 1.00 | 0.12 |
| 244C8-2 | 1.77 | 0.19 |
| 388D4-2 + 244C8-2 | 2.11 | 0.21 |

Figure 14:
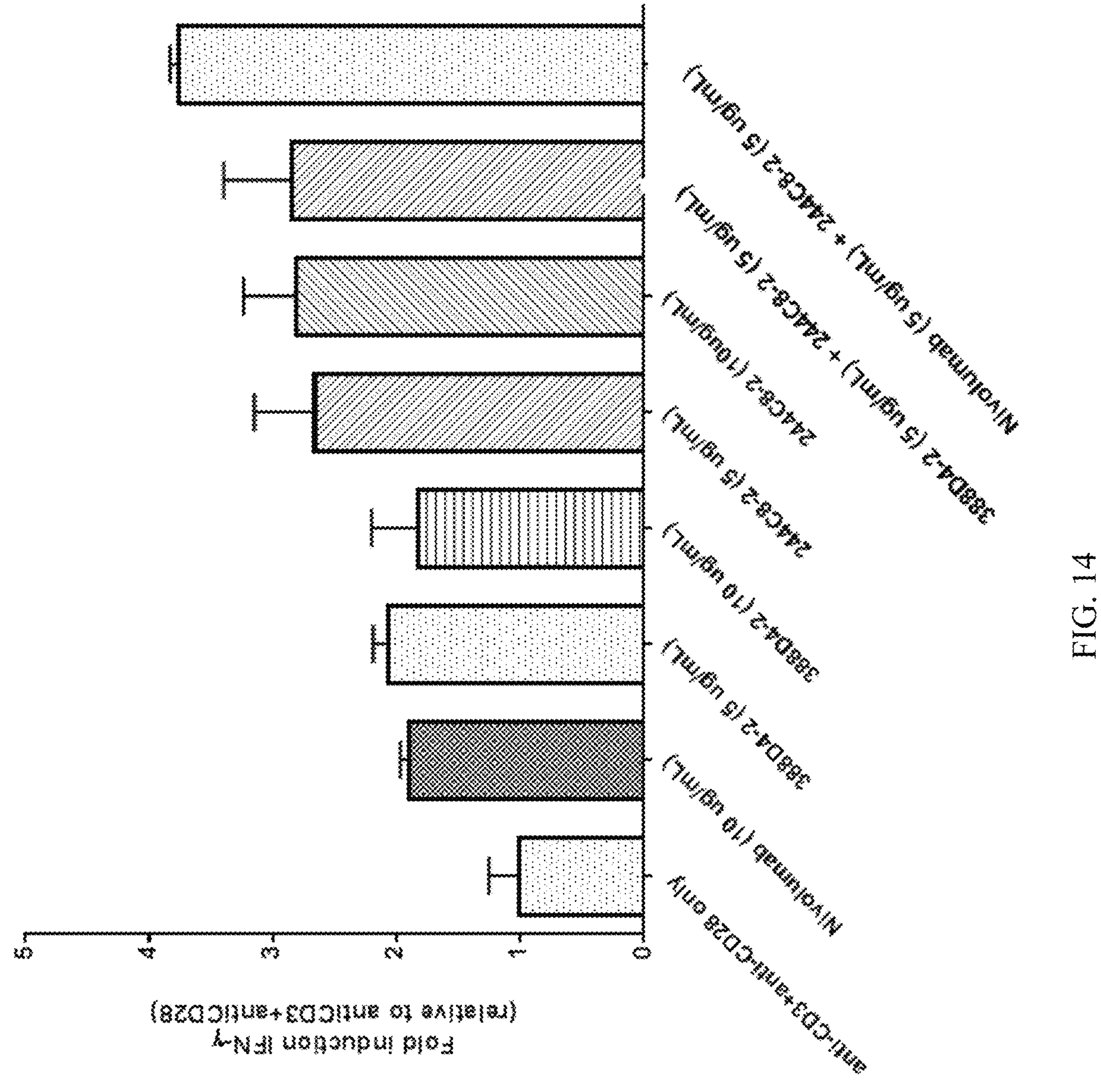
FIG. 14 is a histogram summarizing results from an experiment showing that treatment with the combination of nivolumab and antibody 244C8-2 resulted in greater restoration of T cell effector function than treatment with nivolumab alone, antibody 244C8-2 alone, or antibody 388D4-2 alone. In each treatment, a population of $3\times10^5$ cells, which included 9% lymphocytes (sub-optimally activated as described above) was incubated for 24 hours with anti-PD-1 antibodies at a total concentration of 20 μg/mL. Following PD-1 blockade, cells and supernatants were collected for ELISA measurement of IFNγ. Data are expressed in terms of fold-induction of IFNγ secretion, relative to treatment with the isotype control antibody.
Figure 15A:
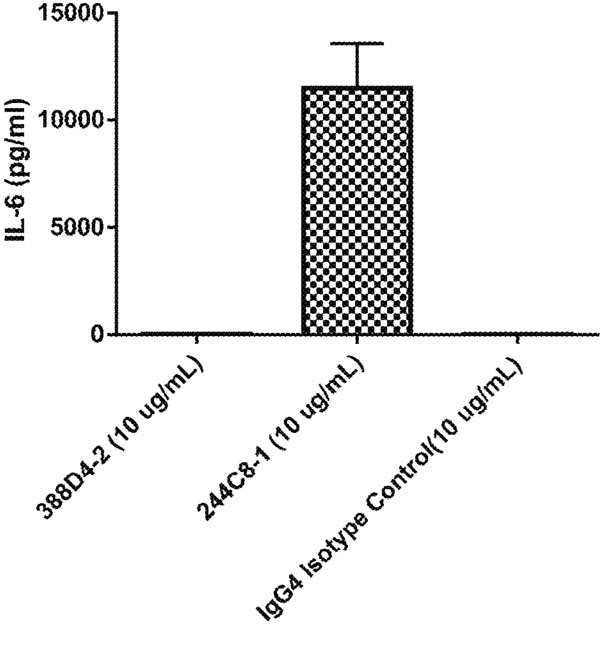
FIGS. 15A-15F are histograms summarizing the results of a mixed lymphocyte reaction (MLR) assay performed on human PBMCs treated with anti-PD-1 antibodies. The MLR assay was performed using commercially available monocyte-derived dendritic cells as stimulator cells and purified CD4+ T lymphocytes as responder cells from a different healthy blood donor. Supernatants were collected 2.5 days after beginning the assay. Treatment with antibody 244C8-1 (100244_C8_HC1+100245_C8_LC1) resulted in increased secretion of cytokines IL-6, IL-12, IL-18, TNF-α, GM-CSF, and IL-1β, in comparison with antibody 388D4-2 (100388_D4_HC3+100389_D4_LC3) or an IgG4 isotype control.
Figure 15B:
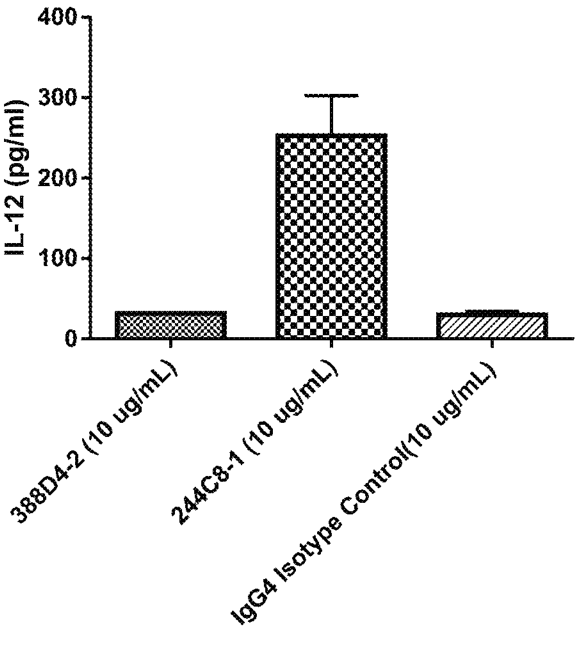
Figures 15C, 15D:
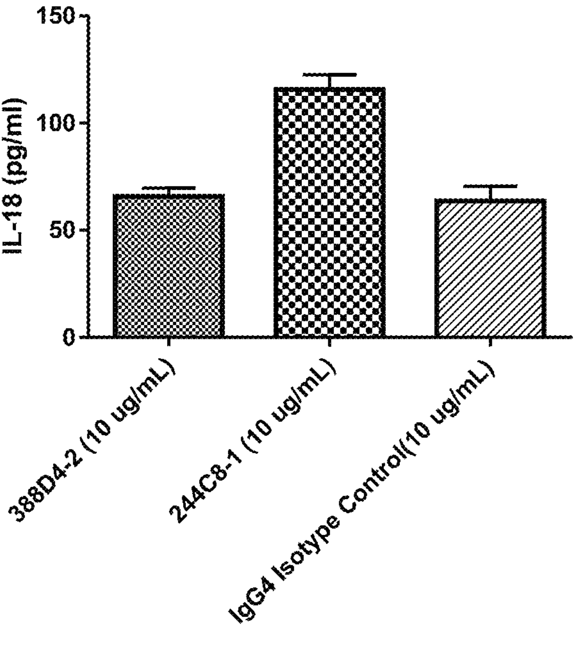
Figure 15E:
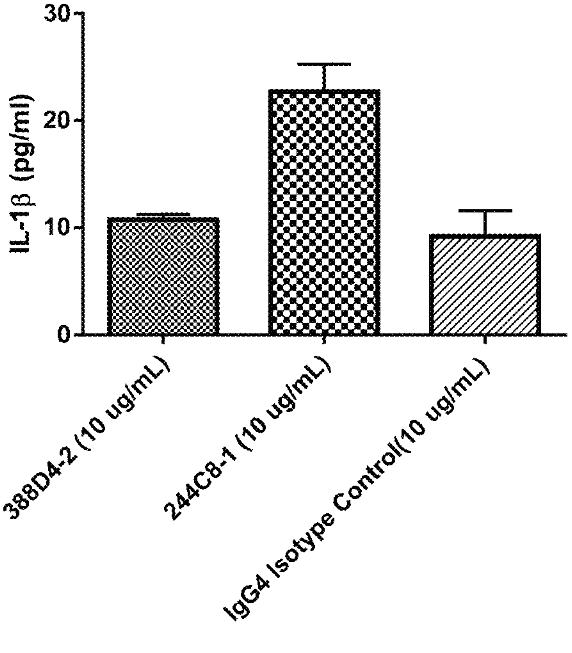
Figure 15F:
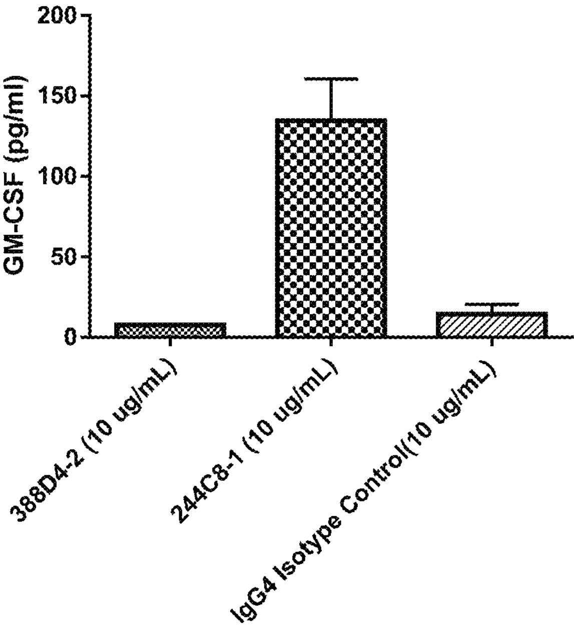
Figure 16A:
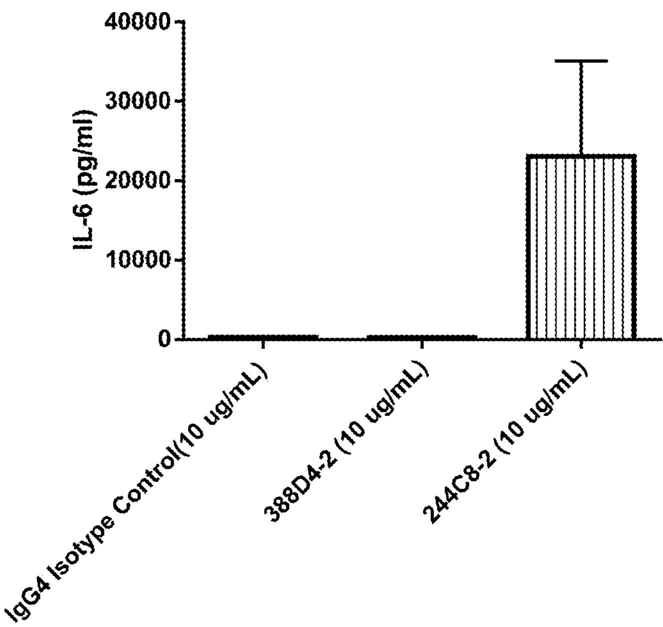
FIGS. 16A-16F are histograms summarizing the results of an experiment showing alteration of tumor infiltrating lymphocyte (TIL) function by PD-1 blockade with anti-PD-1 antibodies 388D4-2 and 244C8-2. A population of $3\times10^5$ dissociated and suspended human cells from a non-small cell lung cancer (NSCLC) biopsy, which included 7% stimulated, tumor-infiltrating lymphocytes was incubated for 24 hours with anti-CD3 and anti-CD28 antibodies along with an anti-PD-1 antibody or IgG4 isotype control at a concentration of 10 μg/mL. Treatment with antibody 244C8-2 (100244_C8_HC1+100245_C8_LC3) resulted in increased secretion of cytokines IL-6, IL-12, IL-18, TNF-α, GM-CSF, and IL-1β, in comparison with antibody 388D4-2 (100388_D4_HC3+100389_D4_LC3) or the IgG4 isotype control.
Figure 16B:
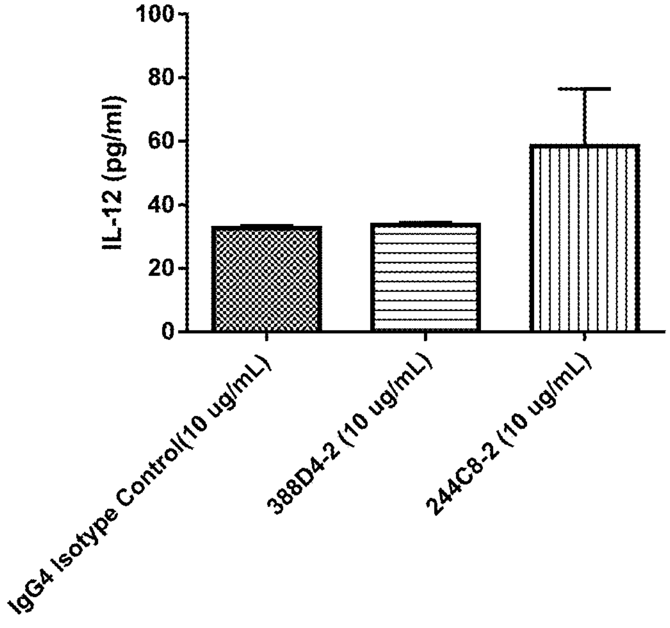
Figure 16C:
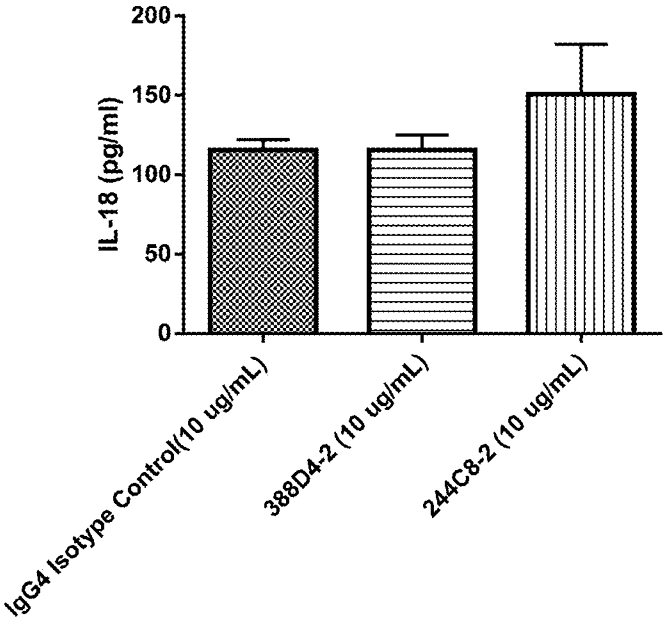
Figure 16D:
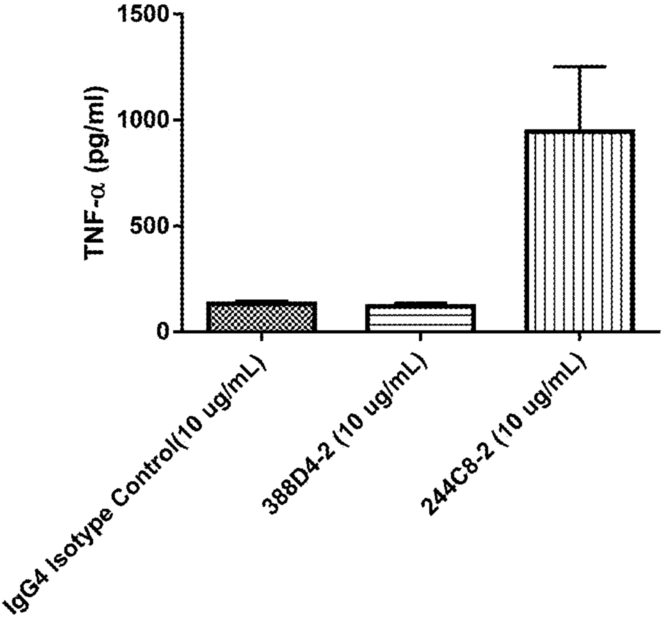
Figure 16E:
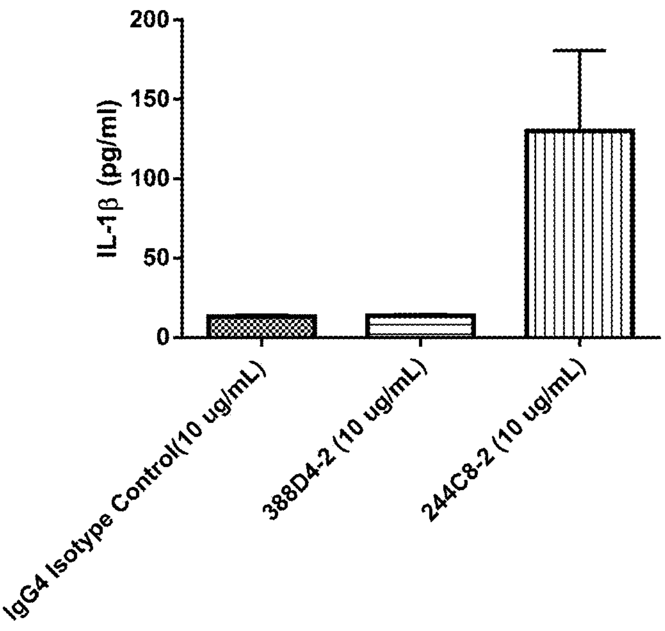
Figure 16F:
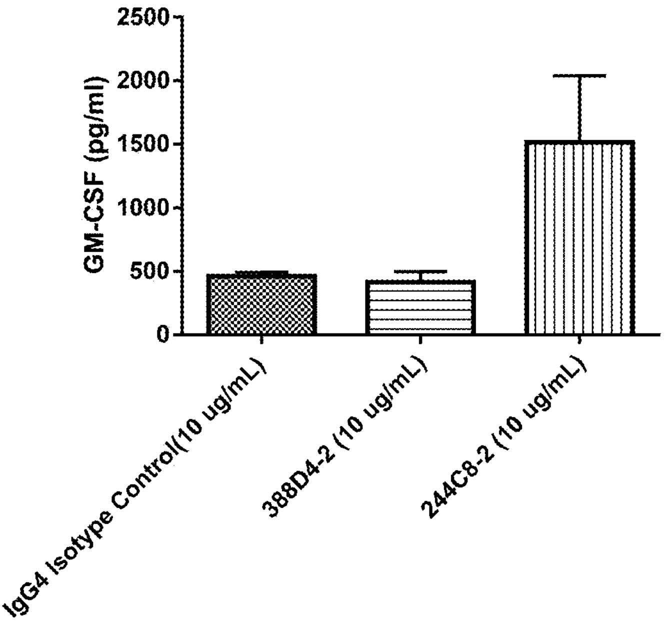

FIG. 14 shows results from an experiment similar to the experiment yielding the results presented in FIG. 12, except that different humanized forms of antibodies 388D4 and 244C8 were tested, and nivolumab was tested in combination with 244C8. In each treatment, a population of $3\times10^5$ cells, which included 9% lymphocytes (sub-optimally activated as described above) was incubated for 24 hours with anti-PD-1 antibodies at a total concentration of 20 μg/mL. Following PD-1 blockade, cells and supernatants were collected for FACS analysis, analysis by microengraving in a microwell array device (Varadarajan, supra), or ELISA detection of cytokines. FIG. 14 shows IFNγ secretion, as measured by ELISA, with data expressed in terms of fold-induction of IFNγ secretion, relative to treatment with the isotype control antibody. The data used to create FIG. 14 are shown in Table 13 below.

TABLE 13

Increase in IFN-γ induction by combination of anti-PD-1 antibodies

| | Fold Induction IFN-γ | Standard Deviation |
|---|---|---|
| anti-CD3 + anti-CD28 only | 1.00 | 0.25 |
| Nivolumab (10 ug/mL) | 1.89 | 0.07 |
| 388D4-2 (5 ug/mL) | 2.06 | 0.12 |
| 388D4-2 (10 ug/mL) | 1.82 | 0.38 |
| 244C8-2 (5 ug/mL) | 2.66 | 0.49 |
| 244C8-2 (10 ug/mL) | 2.81 | 0.42 |
| 388D4-2 (5 ug/mL) + 244C8-2 (5 ug/mL) | 2.85 | 0.55 |
| Nivolumab (5 ug/mL) + 244C8-2 (5 ug/mL) | 3.76 | 0.08 |

The data summarized in FIG. 14 show significantly increased response to treatment of TILS from NSCLC biopsies when treated with the combination of nivolumab, which is a competitive inhibitory anti-PD-1 antibody, and 244C8-2, which is a non-competitive inhibitory anti-PD-1 antibody. Individual antibody treatment with each of two different anti-PD-1 antibodies that compete with PD-L1 for binding to PD-L1, i.e., nivolumab and 388D4-2, increased T cell effector function approximately 2-fold. Individual antibody treatment with an anti-PD-1 antibody that does not compete with PD-L1 for binding to PD-L1, i.e., 244C8-2, increased T cell effector function between 2.5-fold and 3-fold. Treatment with nivolumab plus 244C8-2 increased T cell effector function between 3.5-fold and 4-fold.

When experiments such as these are performed on human patient tumor biopsy samples, the magnitude of increase in T cell effector function observed in response to the same antibody treatment can vary from experiment to experiment as a function of patient-to-patient variation. In spite of such patient-to-patient variation, these results indicate that the addition of a non-competitive inhibitory anti-PD-1 antibody treatment to a competitive inhibitory anti-PD-1 antibody treatment can yield a greater increase in effector function of TILs, as compared to treatment with the competitive inhibitory anti-PD-1 antibody alone.

F. Antibody 244C8 and Cytokine Secretion in MLR Assays

Increased secretion of various cytokines was observed in response to antibody 244C8 in mixed lymphocyte reaction (MLR) assays. FIGS. 15A-15F summarize the results of an MLR assay performed on human PBMCs treated with anti-PD-1 antibodies. The MLR assay was performed using commercially available monocyte-derived dendritic cells as stimulator cells and purified CD4+T lymphocytes as responder cells from a different healthy blood donor. Supernatants were collected at 2.5 days after beginning the assay. Cytokine secretion was measured in a multiplex capture sandwich immunoassay using MagPlex® microspheres (Luminex, Austin, TX) and ProCartaPlex® Human TH1/TH2 Chemokine Panel (Luminex), according to the vendor's instructions. Fluorescence of the various labels was detected using a MagPix® fluorescence detection system (Luminex). The data in FIGS. 15A-15F indicate that treatment with antibody 244C8-1 resulted in increased secretion of cytokines IL-6, IL-12, IL-18, TNF-α, GM-CSF, and IL-1β, in comparison with antibody 388D4-2 or the IgG4 isotype control (Biolegend). Similar results (data not shown) were observed with cells from two other blood donors, at two time points.

G. Antibody 244C8 and Cytokine Secretion by TILs

Increased secretion of various cytokines by TILs was observed in response to antibody 244C8. FIGS. 16A-16F show alteration of tumor infiltrating lymphocyte (TIL) function by PD-1 blockade with antibodies 388D4-2, and 244C8-2. In this experiment, a population of $3\times10^5$ dissociated and suspended human cells from a non-small cell lung cancer (NSCLC) biopsy, which included 7% lymphocytes that had been activated as described in Example 5C (above) was incubated for 24 hours with an anti-PD-1 antibody or IgG4 isotype control, at a concentration of 10 μg/mL. Cytokine secretion was measured in a multiplex capture sandwich immunoassay using MagPlex® microspheres (Luminex) and ProCartaPlex® Human TH1/TH2 Chemokine Panel (Luminex), according to the vendor's instructions. Fluorescence of the various labels was detected using a MagPix® fluorescence detection system (Luminex). These data indicate that treatment with antibody 244C8-2 resulted in increased secretion of cytokines IL-6, IL-12, IL-18, TNF-α, GM-CSF, and IL-1β, in comparison with antibody 388D4-2 or the IgG4 isotype control (Biolegend). Similar results (not shown) were obtained by employing this protocol with three other human tumor samples.

Example 6. Animal Models

A. Patient-Derived Xenografts in Humanized Mice

Figure 17A:
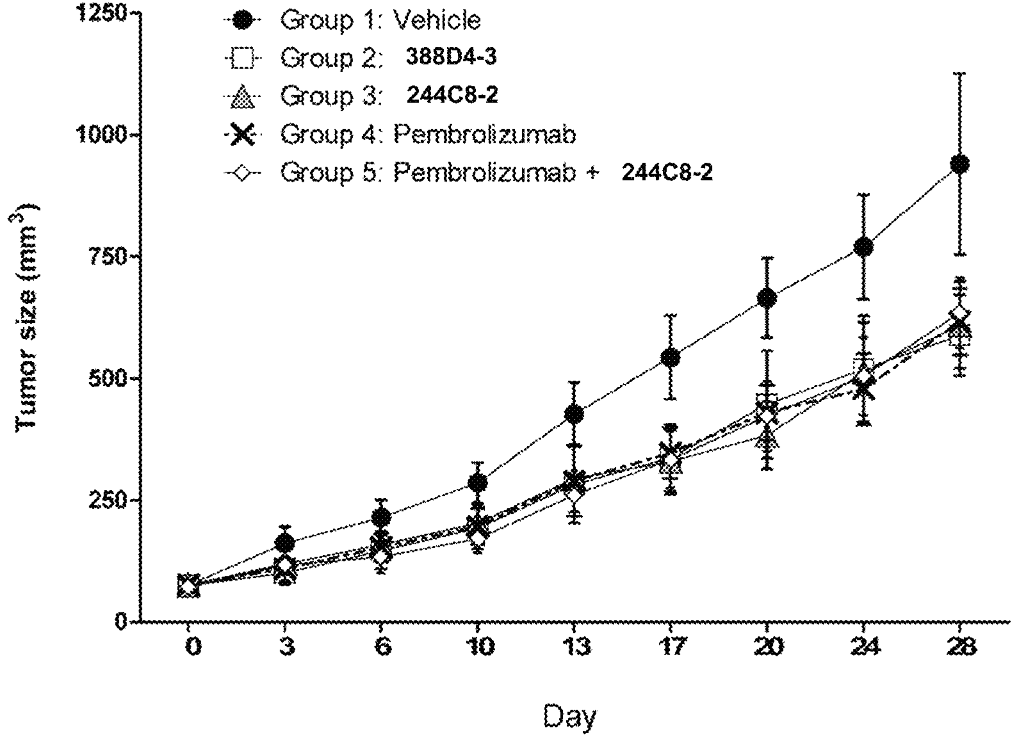
FIGS. 17A-17C show the results from an in vivo efficacy experiment involving patient-derived xenograft (PDX) lung tumor growth in humanized mice treated with vehicle control, antibody 388D4-3, antibody 244C8-2, pembrolizumab, or a combination of antibody 244C8-2 and pembrolizumab. Animals received a total of six intra-peritoneal doses of antibody at five-day intervals (Q5D×6) 5 mg/kg. In the treatment groups that received 388D4-3, 244C8-2 or pembrolizumab, the first dose of the antibody was given as a 10 mg/kg dose, followed by the additional doses at the 5 mg/kg dose. The combination treatment group received a dose of each 5 mg/kg of pembrolizumab and 5 mg/kg of 244C8-2 at each dosing time point. Tumor volumes were measured twice weekly (Day 3, 6, 10, 13, 17, 20, 24 and 28) using a digital caliper to determine length and width of the tumors. All animals were sacrificed at day 28 after dosing initiation. Error bars represent the 95% confidence interval (n=10). All treatment groups showed significant tumor growth inhibition compared to the vehicle control group.

Antibodies 244C8 and 388D4 displayed anti-tumor activity in patient-derived xenograft (PDX) tumor growth in humanized mice. FIG. 17A shows results from an in vivo efficacy experiment involving a human lung tumor PDX-derived from a metastatic stage IV non-small cell lung cancer (NSCLC) patient (lung tumor LG1306; Jackson Labs) implanted in mice engineered to have a human immune system (hu-CD34 NSG™ mice; Jackson Labs). The five treatment groups were: vehicle control, antibody 388D4-3, antibody 244C8-2, pembrolizumab, or a combination of antibody 244C8-2 and pembrolizumab. Mice that had been engrafted with human CD34+ cells and had >25% human CD45+ cells in the peripheral blood at twelve weeks post-engraftment were implanted subcutaneously on the right flank with tumor fragments from PDX model LG1306. Mice were randomized into five treatment groups (n=10), based on tumor volume, when volume reached 60-120 $mm^3$. Animals received a total of six intra-peritoneal 5 mg/kg doses at five-day intervals (Q5D×6). All doses were delivered in PBS as vehicle. In the treatment groups that received 388D4-3, 244C8-2, or pembrolizumab, the first dose of the antibody was given as a 10 mg/kg dose, followed by the additional doses at the 5 mg/kg dose. The combination treatment group (244C8-2+pembrolizumab) received a dose each of 5 mg/kg pembrolizumab and 5 mg/kg of 244C8-2 at each dosing time point. Tumor volumes were measured twice weekly (Day 3, 6, 10, 13, 17, 20, 24 and 28) using a digital caliper to determine length and width of the tumors. Error bars represent the 95% confidence interval.

All treatment groups showed significant tumor growth inhibition compared to the vehicle control group. In this experiment, no significant difference in tumor growth inhibition was observed among treatment with antibody 388D4-

Figure 17B:
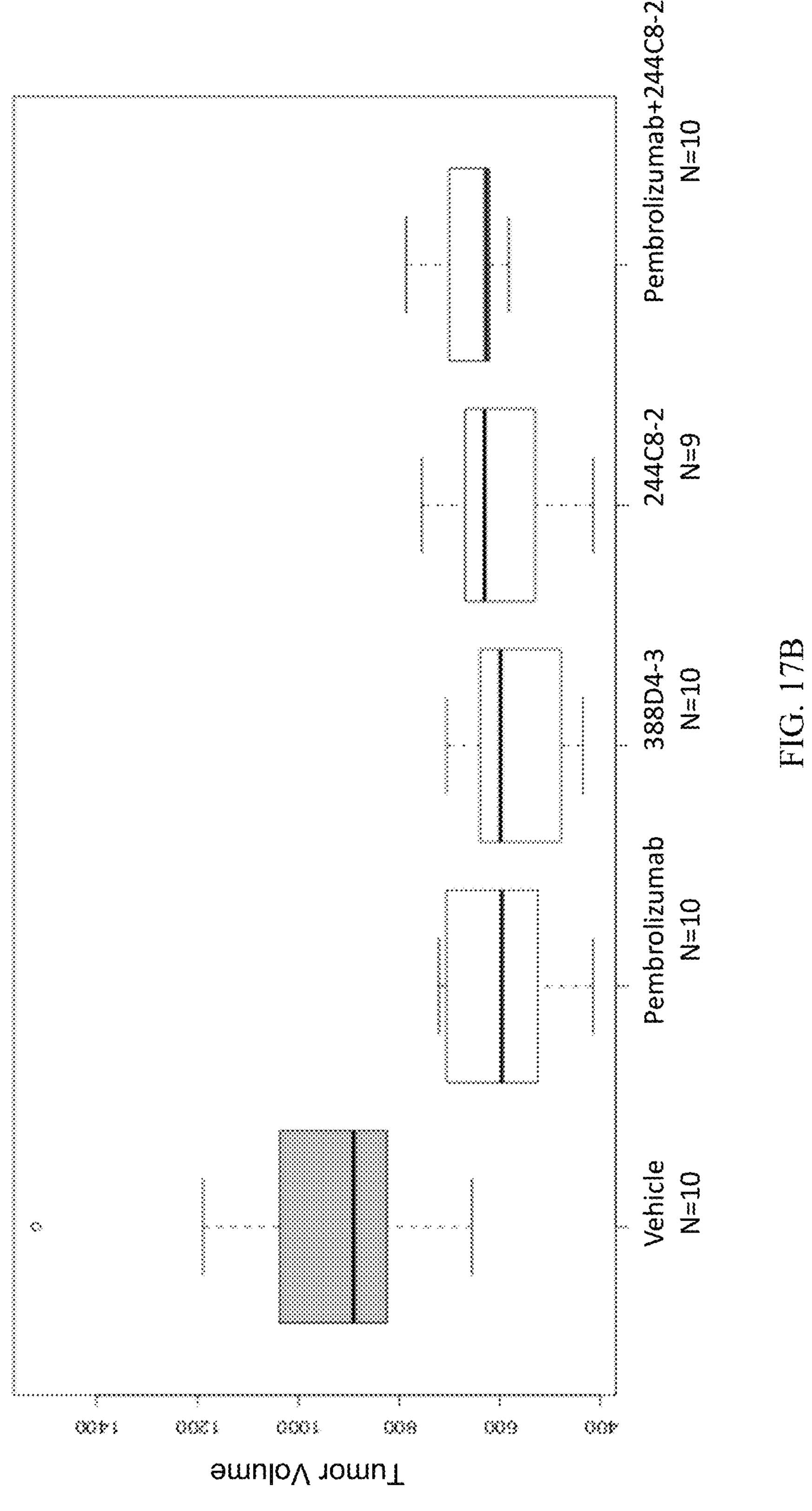
Figure 17C:
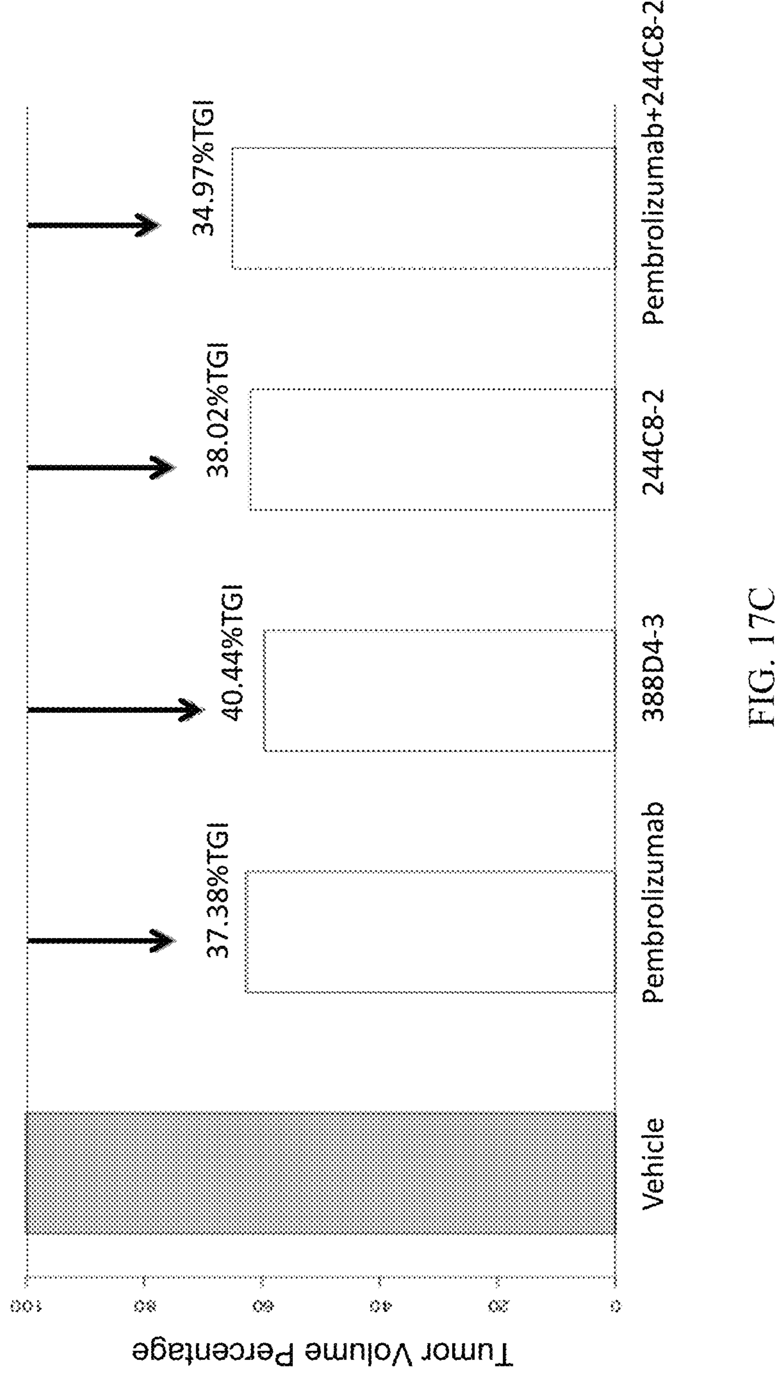

3, antibody 244C8-2, pembrolizumab, or the combination of antibody 244C8-2 with pembrolizumab. As shown in FIG. 17B, at day 28 (end of study), the tumor volume for each of the treatment groups was significantly smaller than the vehicle group. The Student T-test p values between each treatment group and the vehicle group were: pembrolizumab=0.00167; 388D4=0.00105; 244C8=0.00277; and pembrolizumab and 244C8 in combination=0.00275. FIG. 17C shows percentage tumor volume of each treatment group relative to vehicle on day 28. The calculated percent tumor growth inhibition (% TGI) for each treatment is shown above each bar in FIG. 17C. Percent tumor growth inhibition was calculated according to the following formula:

$$\%TGI\ on\ Day\ X=(1-(T_{DayX}-T_{Day\text{-}1})/(C_{DayX}-C_{Day\text{-}1}))*100$$

where:
T=the average tumor volume for a treatment group; and
C=the average tumor volume for the control group.

In this experiment, it was surprisingly discovered that in the combination treatment, a combined antibody dose totaling 10 mg/kg was well tolerated by the animals, for the duration of the study.

INCORPORATION BY REFERENCE

The relevant teachings of all patents, published applications, and references cited herein are incorporated by reference in their entirety.

EQUIVALENTS

While this invention has been particularly shown and described with references to examples of embodiments thereof, it will be understood by those skilled in the art that various changes in form and details may be made therein without departing from the scope of the invention encompassed by the appended claims.

What is claimed is:

1. An isolated antibody that binds to programmed cell death protein 1 (PD-1), comprising a heavy chain variable region (HCVR) having complementarity determining regions (CDRs) 1-3 of SEQ ID NO: 25, and a light chain variable region (LCVR) having CDRs 1-3 of SEQ ID NO: 45.

2. The antibody according to claim 1, wherein the antibody comprises a HCVR having the sequence set forth in SEQ ID NO: 25 and a LCVR having the sequence set forth in SEQ ID NO: 45.

3. The antibody according to claim 1, comprising a humanized or human framework region.

4. The antibody according to claim 1, wherein the antibody binds to a sequence in PD-1 selected from the group consisting of SEQ ID NO: 74, SEQ ID NO: 75, SEQ ID NO: 76, SEQ ID NO: 77, SEQ ID NO: 78, SEQ ID NO: 79, SEQ ID NO: 80 and SEQ ID NO: 81, or a combination thereof.

5. The antibody according to claim 1, wherein the antibody is monoclonal.

6. The antibody according to claim 1, wherein the antibody is a PD-1 antagonist.

7. An isolated nucleic acid comprising a nucleotide sequence encoding the antibody of claim 1.

8. An expression vector comprising the nucleic acid of claim 7.

9. A host cell transformed with an expression vector of claim 8.

10. A method of producing an antibody, the method comprising:

a) growing the host cell of claim 9 under conditions such that the host cell expresses the antibody; and b) isolating the antibody.

11. A method of treating a cancer in a mammal in need thereof, comprising administering an effective amount of the antibody according to claim 6 to the mammal.

12. A method of diagnosing a PD-1-mediated adaptive immune resistance in a patient who has cancer, comprising:

contacting a tumor microenvironment in the patient with the antibody according to claim 1 labeled with a detectable moiety; and detecting expression of PD-1 on CD8+ T cells within the tumor microenvironment.

13. The method of claim 12, further comprising detecting expression of PD-L1 in the tumor microenvironment.

14. A method for increasing T cell effector function, comprising contacting a T cell with the antibody of claim 6.

* * * * *